(12) United States Patent
Gomis et al.

(10) Patent No.: US 10,793,642 B2
(45) Date of Patent: *Oct. 6, 2020

(54) BINDING MEMBERS FOR HUMAN C-MAF

(71) Applicant: INBIOMOTION S.L., Barcelona (ES)

(72) Inventors: Roger Gomis, Barcelona (ES); Juan Carlos Tercero, Madrid (ES)

(73) Assignee: INBIOMOTION S.L., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/534,893

(22) PCT Filed: Dec. 11, 2015

(86) PCT No.: PCT/IB2015/059562
§ 371 (c)(1),
(2) Date: Jun. 9, 2017

(87) PCT Pub. No.: WO2016/092524
PCT Pub. Date: Jun. 16, 2016

(65) Prior Publication Data
US 2017/0369589 A1  Dec. 28, 2017

Related U.S. Application Data

(60) Provisional application No. 62/090,599, filed on Dec. 11, 2014.

(51) Int. Cl.
C07K 16/32 (2006.01)

(52) U.S. Cl.
CPC ......... C07K 16/32 (2013.01); *C07K 2317/34* (2013.01); *C07K 2317/92* (2013.01)

(58) Field of Classification Search
CPC .................................................... C07K 16/32
USPC ..................................................... 424/133.1
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,424,200 A | 1/1984 | Crockford et al. | |
| 4,479,930 A | 10/1984 | Hnatowich | |
| 5,093,246 A | 3/1992 | Cech et al. | |
| 5,185,243 A | 2/1993 | Ullman et al. | |
| 5,814,468 A | 9/1998 | Siiman et al. | |
| 5,958,671 A | 9/1999 | Glimcher et al. | |
| 6,090,367 A | 7/2000 | Khalil | |
| 6,274,338 B1 * | 8/2001 | Glimcher | C07K 14/82 435/320.1 |
| 6,740,522 B2 | 5/2004 | Anderson et al. | |
| 6,998,253 B1 | 2/2006 | Presta et al. | |
| 7,097,834 B1 | 8/2006 | Boyle | |
| 7,364,736 B2 | 4/2008 | Boyle et al. | |
| 7,411,050 B2 | 8/2008 | Anderson | |
| 8,785,150 B2 | 7/2014 | Taylor et al. | |
| 9,127,302 B2 | 9/2015 | Verrant et al. | |
| 9,134,237 B2 | 9/2015 | Connelly et al. | |
| 9,702,878 B2 | 7/2017 | Gomis et al. | |
| 10,006,091 B2 | 6/2018 | Gomis et al. | |
| 10,047,398 B2 | 8/2018 | Gomis et al. | |
| 10,114,022 B2 | 10/2018 | Gomis et al. | |
| 10,119,171 B2 | 11/2018 | Gomis et al. | |
| 2007/0010469 A1 | 1/2007 | Chan et al. | |
| 2009/0048117 A1 | 2/2009 | Glimcher et al. | |
| 2014/0057796 A1 | 2/2014 | Gomis et al. | |
| 2014/0105918 A1 | 4/2014 | Gomis et al. | |
| 2014/0162887 A1 | 6/2014 | Martin et al. | |
| 2014/0314792 A1 | 10/2014 | Gomis et al. | |
| 2015/0152506 A1 | 6/2015 | Gomis et al. | |
| 2015/0362495 A1 | 12/2015 | Gomis et al. | |
| 2016/0032399 A1 | 2/2016 | Gomis et al. | |
| 2016/0032400 A1 | 2/2016 | Gomis et al. | |
| 2016/0040247 A1 | 2/2016 | Gomis et al. | |
| 2017/0002357 A1 | 1/2017 | Gomis et al. | |
| 2017/0101683 A1 | 4/2017 | Gomis et al. | |
| 2017/0121777 A1 | 5/2017 | Gomis et al. | |
| 2017/0370935 A1 | 12/2017 | Gomis et al. | |
| 2019/0119757 A1 | 4/2019 | Gomis et al. | |
| 2019/0169693 A1 | 6/2019 | Gomis et al. | |
| 2019/0242898 A1 | 8/2019 | Gomis et al. | |
| 2019/0256922 A1 | 8/2019 | Gomis et al. | |
| 2019/0269707 A1 | 9/2019 | Gregory et al. | |
| 2019/0309299 A1 | 10/2019 | Gomis et al. | |

FOREIGN PATENT DOCUMENTS

| | | |
|---|---|---|
| EP | 0120694 A2 | 10/1984 |
| EP | 0125023 A1 | 11/1984 |
| EP | 0184187 A2 | 6/1986 |
| EP | 0239400 A2 | 9/1987 |
| EP | 2412825 A1 | 2/2012 |
| WO | WO-9109967 A1 | 7/1991 |

(Continued)

OTHER PUBLICATIONS

KabatMan—Simple Interface to the Kabat Sequence Database, http://www.bioinf.org.uk/abs/simkab.html., Data accessed Apr. 11, 2017, last accessed Apr. 11, 2019, 4 pages.

Afinitor.com, "AFINITOR (everolimus) tablets," accessed at http://www.afinitor.com/index.jsp?usertrack.filter_applied=true &Novald=4029462064338207963; accessed on Oct. 16, 2014, 5 pages.

Al-Lazikani, B., et al., "Standard Conformations for the Canonical Structures of Immunoglobulins," Journal of Molecular Biology 273(4):927-948, Academic Press Limited, United States (Nov. 1997).

Altschul, S.F., et al., "Basic Local Alignment Search Tool," Journal of Molecular Biology 215(3):403-410, Elsevier, England (Oct. 1990).

Amit, A.G., et al., "Three-Dimensional Structure of an Antigen-Antibody Complex at 2.8 A Resolution," Science 233(4765):747-753, American Association for the Advancement of Science, United States (1986).

(Continued)

*Primary Examiner* — Sean E Aeder
(74) *Attorney, Agent, or Firm* — Sterne, Kessler, Goldstein & Fox P.L.L.C.

(57) ABSTRACT

The disclosure relates to binding members, especially antibody molecules, which bind to human Maf. The binding members are useful for the determination of the expression level of Maf.

22 Claims, 11 Drawing Sheets

Specification includes a Sequence Listing.

(56) References Cited

FOREIGN PATENT DOCUMENTS

| | | |
|---|---|---|
| WO | WO-9201047 A1 | 1/1992 |
| WO | WO-9311161 A1 | 6/1993 |
| WO | WO-9413804 A1 | 6/1994 |
| WO | WO-0034784 A1 | 6/2000 |
| WO | WO-0055126 A2 | 9/2000 |
| WO | WO-0149288 A1 | 7/2001 |
| WO | WO-0175171 A2 | 10/2001 |
| WO | WO-03020278 A1 | 3/2003 |
| WO | WO-03020721 A1 | 3/2003 |
| WO | WO-03068819 A1 | 8/2003 |
| WO | WO-2004000843 A1 | 12/2003 |
| WO | WO-2004006955 A1 | 1/2004 |
| WO | WO-2005046731 A1 | 5/2005 |
| WO | WO-2007045996 A1 | 4/2007 |
| WO | WO-2008086800 A2 | 7/2008 |
| WO | WO-2008098351 A1 | 8/2008 |
| WO | WO-2008133766 A1 | 11/2008 |
| WO | WO-2008142164 A2 | 11/2008 |
| WO | WO-2010003773 A1 | 1/2010 |
| WO | WO-2011039734 A2 | 4/2011 |
| WO | WO-2012045905 A2 | 4/2012 |
| WO | WO 2013/153458 A2 * | 10/2013 |
| WO | WO-2013182912 A2 | 12/2013 |
| WO | WO-2014057357 A2 | 4/2014 |
| WO | WO-2014140896 A2 | 9/2014 |
| WO | WO-2014140933 A2 | 9/2014 |
| WO | WO-2014184679 A2 | 11/2014 |
| WO | WO-2015052583 A2 | 4/2015 |
| WO | WO-2016092524 A1 | 6/2016 |
| WO | WO-2017203468 A1 | 11/2017 |
| WO | WO-2019102380 A1 | 5/2019 |

OTHER PUBLICATIONS

Andersen, D.C. and Krummen, L., "Recombinant Protein Expression for Therapeutic Applications," Current Opinion in Biotechnology 13(2):117-123, Elsevier, England (Apr. 2002).

Barbas, C.F. 3rd., et al., "In vitro evolution of a neutralizing human antibody to human immunodeficiency virus type 1 to enhance affinity and broaden strain cross-reactivity," Proceedings of the National Academy of Sciences 91(9):3809-3813, National Academy of Sciences, United States (1994).

Baselga, J., et al., "Everolimus in Postmenopausal Hormone-Receptor-Positive Advanced Breast Cancer," The New England Journal of Medicine 366(6):520-529, Massachusetts Medical Society, United States (2012).

Biolegend, "Purified anti-c-MAF Antibody, 2D9A29," Biolegend catalog, May 15, 2013, XP055251712, accessed at http://www.biolegend.com/pop_pdf.php?id=8549, accessed on Feb. 19, 2016, 1 page.

Bird, R.E., et al., "Single-chain Antigen-binding Proteins," Science 242(4877):423-426, Association for the Advancement of Science, United States (Oct. 1988).

Caton, A.J., et al., "Identical D Region Sequences Expressed by Murine Monoclonal Antibodies Specific for a Human Tumor-associated Antigen," Journal of Immunology 144(5):1965-1968, American Association of Immunologists, United States (Mar. 1990).

Chadd, H.E. and Chamow, S.M., "Therapeutic Antibody Expression Technology," Current Opinion in Biotechnology 12(2):188-194, Elsevier, England (Apr. 2001).

Choi, M., et al., "Genetic Diagnosis by Whole Exome Capture and Massively Parallel DNA Sequencing," Proceedings of the National Academy of Sciences of USA 106(45):19096-19101, National Academy of Sciences, United States (2009).

Chothia, C. and Lesk, A.M., "Canonical Structures for the Hypervariable Regions of Immunoglobulins," Journal of Molecular Biology 196(4):901-917, Elsevier Science, United States (Aug. 1987).

Chothia, C., et al., "Conformations of Immunoglobulin Hypervariable Regions," Nature 342(6252):877-883, Nature Publishing Group, England (Dec. 1989).

Chothia, C., et al., "The Predicted Structure of Immunoglobulin D1.3 and Its Comparison With the Crystal Structure," Science 233(4765):755-758, American Association for the Advancement of Science, United States (Aug. 1986).

Chothia, C., et al., "Structural Repertoire of the Human VH Segments," Journal of Molecular Biology 227(3):799-817, Academic Press, England (1992).

Dannhardt, G. and Kiefer, W., "Cyclooxygenase Inhibitors—Current Status and Future Prospects," European Journal of Medicinal Chemistry 36(2):109-126,Editions Scientifiques et Medicales Elsevier SAS, France (2001).

Demarest, J.F., et al., "Update on Aplaviroc: An HIV Entry Inhibitor Targeting CCR5," Retrovirology 2(Suppl 1):S13, BioMed Central, England (2005).

Ettenberg, S.A., et al., "BHQ880, A Novel Anti-DKK1 Neutralizing Antibody, Inhibits Tumor-Induced Osteolytic Bone Disease," Proceedings of the American Association for Cancer Research 49:947, Abstract 3987, 3 pages, American Association for Cancer Research, United States (2008).

Eychene, A., et al., "A New*MAF*ia in Cancer," Nature Reviews Cancer 8(9):683-693, Nature Publishing Group, England (2008).

GenBank Database, "*Homo sapiens* v-maf avian musculoaponeurotic fibrosarcoma oncogene homolog (MAF), RefSeqGene on chromosome 16," NCBI Reference Sequence Accession No. NG_016440, accessed at http://www.ncbi.nlm.nih.gov/nuccore/NG_016440, accessed on Apr. 3, 2015, 5 pages.

GenBank Database, "*Homo sapiens* v-maf avian musculoaponeurotic fibrosarcoma oncogene homolog (MAF), transcript variant 1, mRNA," NCBI Reference Sequence Accession No. NM_005360, accessed at http://www.ncbi.nlm.nih.gov/nuccore/NM_005360.4, accessed on Apr. 3, 2015, 5 pages.

GenBank Database, "*Homo sapiens* v-maf avian musculoaponeurotic fibrosarcoma oncogene homolog (MAF), transcript variant 2, mRNA," NCBI Reference Sequence Accession No. NM_001031804, accessed at http://www.ncbi.nlm.nih.gov/nuccore/NM_001031804.2, accessed on Apr. 3, 2015, 6 pages.

Guex, N. and Peitsch, M.C., "Swiss-Model and the Swiss-PdbViewer: An Environment for Comparative Protein Modeling," Electrophoresis 18(15):2714-2723, Wiley-VCH, Germany (Dec. 1997).

Whitelegg, N.R.J., et al., "WAM: An improved algorithm for modelling antibodies on the WEB," Protein Engineering 13(2):819-824, Oxford Journal, United Kingdom (2000).

Holliger, P. and Bohlen, H., "Engineering Antibodies for the Clinic," Cancer Metastasis Reviews 18(4):411-419, Kluwer Academic, Netherlands (1999).

Holliger, P, and Hudson, P.J., "Engineered Antibody Fragments and the Rise of Single Domains," Nature Biotechnology 23(9):1126-1136, Nature America Publishing, United States (2005).

Holliger, P. and Winter, G., "Engineering Bispecific Antibodies," Current Opinion in Biotechnology 4(4):446-449, Current Biology, England (Aug. 1993).

Holliger, P., et al., "Diabodies: Small Bivalent and Bispecific Antibody Fragments," Proceedings of the National Academy of Sciences USA 90(14):6444-6448, National Academy of Sciences, United States (Jul. 1993).

Holt, L.J., et al., "Domain Antibodies: Proteins for Therapy," Trends in Biotechnology 21(11):484-490, Elsevier Science Publishers, England (2003).

http://www.us.zometa.com/index.jsp?usertrack.filter_applied=true &Novald=2935376934467633633; last accessed Apr. 3, 2015, 2 pages.

Hu, S., et al., "Minibody: A Novel Engineered Anti-carcinoembryonic Antigen Antibody Fragment (Single-Chain Fv-CH3) which Exhibits Rapid, High-level Targeting of Xenografts," Cancer Research 56(13):3055-3061, American Association for Cancer Research, United States (Jul. 1996).

Hunter, W.M. and Greenwood, F.C., "Preparation of Iodine-131 Labelled Human Growth Hormone of High Specific Activity," Nature 194:495-496, Nature Publishing Group, England (May 1962).

Huston, J.S., et al., "Protein Engineering of Antibody Binding Sites: Recovery of Specific Activity in an Anti-digoxin Single-chain Fv Analogue Produced in *Escherichia coli*," Proceedings of the National

(56) References Cited

OTHER PUBLICATIONS

Academy of Sciences USA 85(16):5879-5883, National Academy of Sciences, United States (Aug. 1988).

International Preliminary Report on Patentability, including the Written Opinion of the International Searching Authority, for International Application No. PCT/IB2015/059562, dated Jun. 22, 2017, 6 pages.

International Search Report and Written Opinion for International Application No. PCT/IB2015/059562, European Patent Office, Rijswijk, dated Mar. 1, 2016, 12 pages.

Kabat, E.A., et al., "Sequences of Proteins of Immunological Interest," 5th Edition, U.S. Department of Public Health and Human Services, Public Health Service, National Institutes of Health, Bethesda (1991), 3 pages.

Kohler, G. and Milstein, C., "Continuous Cultures of Fused Cells Secreting Antibody of Predefined Specificity," Nature 256(5517):495-497, Macmillan Journals Ltd., England (Aug. 1975).

Koide, A., et al., "The Fibronectin Type III Domain as a Scaffold for Novel Binding Proteins," Journal of Molecular Biology 284(4):1141-1151, Academic Press, United States (Dec. 1998).

Habashy, H.O., "RERG (Ras-like, oestrogen-regulated, growth-inhibitor) expression in breast cancer: a marker of ER—positive luminal-like subtype," Breast Cancer Research and Treatment 128(2):315-326, Springer Publishing, United States (2011).

Kuritzkes, D.R., "HIV-1 Entry Inhibitors: An Overview," Current Opinion in HIV and AIDS 4(2):82-87, Lippincott Williams & Wilkins, United States (2009).

Larrick, J.W., et al., "Producing Proteins in Transgenic Plants and Animals," Current Opinion in Biotechnology 12(4):411-418, Elsevier, England (Aug. 2001).

Ledermann, J.A., et al., "A Phase-I Study of Repeated Therapy With Radiolabelled Antibody to Carcinoembryonic Antigen Using Intermittent or Continuous Administration of Cyclosporin A to Suppress the Immune Response," International Journal of Cancer 47(5):659-664, Wiley-Liss, United States (Mar. 1991).

Marks, J.D., et al., "By-Passing Immunization: Building High Affinity Human Antibodies by Chain Shuffling," Biotechnology 10(7):779-783, Nature Publishing Company, United States (Jul. 1992).

Martin, A.C., "Accessing the Kabat Antibody Sequence Database by Computer," Proteins: Structure, Function, and Genetics, 25(1):130-133, Wiley-Liss, United States (May 1996).

McCafferty, J., et al., "Phage Antibodies: Filamentous Phage Displaying Antibody Variable Domains," Nature 348(6301):552-554, Nature Publishing Group, London (Dec. 1990).

Mendez, M.J., et al., "Functional Transplant of Megabase Human Immunoglobulin Loci Recapitulates Human Antibody Response in Mice," Nature Genetics 15(2):146-156, Nature Pub. Co., United States (1997).

NG, P.C. and Kirkness, E.F., "Whole Genome Sequencing," Methods in Molecular Biology 628:215-226, Springer Science+Business Media, LLC, Netherlands (2010).

Nygren, P.A. and Uhlen, M., "Scaffolds for Engineering Novel Binding Sites in Proteins," Current Opinion in Structural Biology 7(4):463-469, Elsevier Science, England (Aug. 1997).

Pageau, S.C., "Denosumab," Monoclonal Antibodies 1(3):210-215, Landes Bioscience, United States (2009).

Paik, S., et al., "A Multigene Assay to Predict Recurrence of Tamoxifen-Treated, Node-Negative Breast Cancer," The New England Journal of Medicine 351(27):2817-2826, Massachusetts Medical Society, United States (2004).

Pearson, W.R. and Lipman, D.J., "Improved Tools for Biological Sequence Comparison," Proceedings of the National Academy of Sciences of the United States of America 85(8):2444-2448, National Academy of Sciences, United States (1988).

Pluckthun, A., "Antibody Engineering: Advances From the Use of Escherichia coli Expression Systems," BioTechnology 9(6):545-551, Nature Pub. Co., United States (Jun. 1991).

Qui, X.Q., et al., "Small Antibody Mimetics Comprising Two Complementarity-determining Regions and a Framework Region for Tumor Targeting," Nature Biotechnology 25(8):921-929, Nature America Publishing, United States (Aug. 2007).

Reiter, Y., et al., "Engineering Antibody Fv Fragments for Cancer Detection and Therapy: Disulfide-Stabilized Fv Fragments," Nature Biotechnology 14(10):1239-1245, Nature America Publishing, United States (Oct. 1996).

Ghoussaini, M., "Genome-wide association analysis identifies three new breast cancer susceptibility loci," Nature Genetics 44:312-318, Nature Publishing Group, United States (2012).

Rojo, F., et al., "Nuclear PARP-1 Protein Overexpression is Associated with Poor Overall Survival in Early Breast Cancer," Annals of Oncology 23(5):1156-1164, Oxford University Press, England (Sep. 2011).

Rossi, J.J., et al., "Practical Ribozymes. Making Ribozymes Work in Cells," Current Biology 4(5):469-471, Cell Press, England (May 1994).

Rotstein, D.M., et al., "Spiropiperidine CCR5 Antagonists," Bioorganic and Medicinal Chemistry Letters 19(18):5401-5406, Elsevier Ltd., England (2009).

Schier, R., et al., "Isolation of Picomolar Affinity anti-c-erbb-2 Single-chain Fv by Molecular Evolution of the Complementarity Determining Regions in the Center of the Antibody Binding Site," Journal of Molecular Biology 263(4):551-567, Elsevier, England (1996).

Segal, D.M., et al., "The Three-dimensional Structure of a Phosphorylcholine-binding Mouse Immunoglobulin Fab and the Nature of the Antigen Binding Site," Proceedings of the National Academy of Sciences of the United States of America 71(11):4298-4302, National Academy of Sciences, United States (Nov. 1974).

Sen, B. and Johnson, F.M., "Regulation of SRC Family Kinases in Human Cancers," Journal of Signal Transduction 2011(865819):1-14, Hindawi Publishing Corporation, United States (Apr. 2011).

Sharon, J., "Structural Characterization of Idiotopes by Using Antibody Variants Generated by Site-directed Mutagenesis," Journal of Immunology 144(12):4863-4869, American Association of Immunologists, United States (Jun. 1990).

Sharon, J., "Structural Correlates of High Antibody Affinity: Three Engineered Amino Acid Substitutions Can Increase the Affinity of an Anti-p-azophenylarsonate Antibody 200-fold," Proceedings of the National Academy of Sciences of the United States of America 87(12):4814-4817, National Academy of Sciences, United States (Jun. 1990).

Smith, T.F. and Waterman, M.S., "Identification of Common Molecular Subsequences," Journal of Molecular Biology 147(1):195-197, Elsevier, England (Mar. 1981).

Swennenhuis, J.F., et al., "Construction of Repeat-Free Fluorescencein situHybridization Probes," Nucleic Acids Research 40(3):e20:1-8, Oxford University Press, England (Feb. 2012).

Tarragona, M., et al., "Identification of NOG as a Specific Breast Cancer Bone Metastasis-supporting Gene," The Journal of Biological Chemistry 287(25):21346-21355, American Society for Biochemistry and Molecular Biology, United States (Jun. 2012).

Thery, C., et al., "Isolation and Characterization of Exosomes from Cell Culture Supernatants and Biological Fluids," Current Protocols in Cell Biology Chapter 3:3.22.1-3.22.29, Oxford University Press, England (2006).

Velasco-Velazquez, M., et al., "CCR5 Antagonist Blocks Metastasis of Basal Breast Cancer Cells," Cancer Research 72(15):3839-3850, American Association for Cancer Research, United States (Aug. 2012).

Ward, E.S., et al., "Binding Activities of a Repertoire of Single Immunoglobulin Variable Domains Secreted from Escherichia coli," Nature 341(6242):544-546, Nature Publishing Group, England (Oct. 1989).

Wess, "BioCentury: The Bernstein Report on BioBusiness," 12(43), A1-A7 (2004).

Zhang, X.H-F., et al., "Latent Bone Metastasis in Breast Cancer Tied to Src-Dependent Survival Signals," Cancer Cell 16(1):67-78, Cell Press, United States (2009).

Zhou, H., et al., "Updates of mTOR Inhibitors," Anticancer Agents in Medicinal Chemistry 10(7):571-581, Bentham Science Publishers, Netherlands (2010).

(56) References Cited

OTHER PUBLICATIONS

Kurschner, C., et al., "The *maf* Proto-oncogene Stimulates Transcription from Multiple Sites in a Promoter That Directs Purkinje Neuron Specific Gene Expression," Mol Cell Biol 15(1):246-254, American Society for Microbiology, United States (1995).

Lewis, M., et al., "Expression of progesterone metabolizing enzyme genes (AKRICI, AKRIC2, AKRIC3, SRD5A1, SRD5A2) is altered in human breast carcinoma," BMC Cancer 4:27-39, BioMed Central, Great Britain (2004).

Byrns, M.C., et al., "Type 5 17β-Hydroxysteroid Dehydrogenase/ Prostaglandin F synthase (AKR1C3): Role in Breast Cancer and Inhibition by Nonsteroidal Antiinflamatory Drug Analogs," Chem Biol Interact. 178(1-3): 221-227, Elsevier, Netherlands (2009).

Koch, M., et al., "CD36-mediated activation of endothelial cell apoptosis by an N-terminal recombinant fragment of thrombospondin-2 inhibits breast cancer growth and metastasis in vivo," Breast Cancer Res Treat 128:337-346, Springer Science, United States (2011).

Cao, S., et al., "The protooncogene c-Maf is an essential transcription factor for IL-10 gene expression in macrophages," J Immunol 174:3484-3492, American Association of Immunologists, United States (2005).

Peng, S., et al., "c-Maf increases apoptosis in peripheral CD8 cells by transactivating Caspase 6," Immunology 127:267-278, Blackwell Publishing, United States (2009).

Hideshima, T., et al., "Understanding multiple myeloma pathogenesis in the bone marrow to identify new therapeutic targets," Nature Reviews Cancer 7:585-598, Nature Publishing Group, United States (2007).

Kataoka, K., et al., "Multiple mechanisms and functions of Maf Transcripction factors in the regulation of Tissue-specific genes," J Biochem 141(6):775-781, Oxford University Press, United Kingdom (2007).

Somasiri, A., et al., "Overexpression of the Anti-adhesin Podocalyxin is an Independent Predictor of Breast Cancer Progression," Cancer Res 64:5068-5073, American Association for Cancer Research, United States (2004).

Co-pending, U.S. Appl. No, 15/984,629, inventors Gomis, R., et al., filed May 21, 2018 (Not Published).

Co-pending, U.S. Appl. No, 15/944,510, inventors Gomis, R., et al., filed Apr. 3, 2018 (Not Published).

Co-pending, U.S. Appl. No, 15/944,499, inventors Gomis, R., et al., filed Apr. 3, 2018 (Not Published).

Co-pending, U.S. Appl. No, 16/303,945, inventors Gomis, R., et al., filed Nov. 21, 2018 (Not Published).

Co-pending, U.S. Appl. No. 16/142,168, inventors Gomis, R., et al., filed Sep. 26, 2018 (Not Published).

Co-pending, U.S. Appl. No. 16/134,449, inventors Gomis, R., et al., filed Sep. 18, 2018 (Not Published).

Co-pending, U.S. Appl. No. 16/028,530, inventors Gomis, R., et al., filed Jul. 6, 2018 (Not Published).

Co-pending, U.S. Appl. No. 15/955,790, inventors Gomis, R., et al., filed Apr. 18, 2018 (Not Published).

Haan, K., et al., "The Protein Engineers," Bernstein Report on BioBusiness, Tools and techniques 12(5):A1-A6, Biocentury, United States (2004).

Kataoka, K., et al., "MafA is a Glucose-regulated and Pancreatic B-Cell-specific Transcriptional Activator for the Insulin Gene*," Journal of Biological Chemistry 277(51):49903-49910, American Society for Biochemistry and Molecular Biology, United States (2002).

Santa Cruz Biotechnology, Inc., "Product Catalog, c-Maf(M-153):sc-7866," retrieved from: http://datasheets.scbt.com/sc-7866.pdf, retrieved Oct. 24, 2019, 1 page.

\* cited by examiner

① Red. Transactivation domain
② Green: Extended domain
③ Light green: Basic domain
④ Orange: Leucine Zipper
⑤ Brown: Glycine and Hystidine rich domains

Figure 2.

Sequence alignments

```
NP_001038136.1    1    MASELAMSGSDLPTSPLAMEYVNDFDLMKFEVKKEPVETDRIISQCGRLI    50
NP_571919.1       1    MASELALSSSDLPTSPLAMEYVNDFDLMKFEVKKEPLEPDRSITQCSRLI    50
XP_003201520.1    1    MASELAMSSSDLPTSPLAMEYVNDFDLMKFEVKKEPVEPDRSISQCSRLI    50
NP_005351.2       1    MASELAMSNSDLPTSPLAMEYVNDFDLMKFEVKKEPVETDRIISQCGRLI    50
XP_511123.2       1    MASELAMSNSDLPTSPLAMEYVNDFDLMKFEVKKEPVETDRIISQCGRLI    50
NP_001099107.1    1    MASELAMSNSDLPTSPLAMEYVNDFDLMKFEVKKEPVETDRIISQCGRLI    50
NP_062191.1       1    MASELAMNNSDLPTSPLAMEYVNDFDLMKFEVKKEPVETDRIISQCGRLI    50
NP_001020748.2    1    MASELAMNNSDLPTSPLAMEYVNDFDLMKFEVKKEPVETDRIISQCGRLI    50

NP_001038136.1    51   AGGSLSSTPMSTPCSSVPPSPSFSAPSPGSGTDQKTHLEDYYWMTGYPQQ    100
NP_571919.1       51   AGGSLSSTPMSTPCSSVPPSPSFSAPSPGSGNEQKGHLEDFYWMTGYQQQ    100
XP_003201520.1    51   AGGSLSSTPMSTPCSSVPPSPSFSAPSPGSGSEQKAHLEDFYWMTGYQQQ    100
NP_005351.2       51   AGGSLSSTPMSTPCSSVPPSPSFSAPSPGSGSEQKAHLEDYYWMTGYPQQ    100
XP_511123.2       51   AGGSLSSTPMSTPCSSVPPSPSFSAPSPGSGSEQKAHLEDYYWMTGYPQQ    100
NP_001099107.1    51   AGGSLSSTPMSTPCSSVPPSPSFSAPSPGSGSEQKAHLEDYYWMTGYPQQ    100
NP_062191.1       51   AGGSLSSTPMSTPCSSVPPSPSFSAPSPASGSEQKAHLEDYYWMTGYPQQ    100
NP_001020748.2    51   AGGSLSSTPMSTPCSSVPPSPSFSAPSPGSGSEQKAHLEDYYWMTGYPQQ    100

NP_001038136.1    101   LNPEALGFSPEDAVEALINSSHHPLPGAFDGYARG-QQLAAAA--GGSV-    146
NP_571919.1       101   LNPEALGFSSEDAVEALINSTHQ-LQ-SYDGYARG-QQFSNTAGTGGAM-    146
XP_003201520.1    101   LNPEALGFSPEDAVEALISSSHQ-LQ-SFDGYARG-QQFGGAAGAGGAM-    146
NP_005351.2       101   LNPEALGFSPEDAVEALISNSHQ-LQGGFDGYARGAQQLAAAAGAGAGAS    149
XP_511123.2       101   LNPEALGFSPEDAVEALISNSHQ-LQGGFDGYARGAQQLAAAAGAGAGAS    149
NP_001099107.1    101   LNPEALGFSPEDAVEALISNSHQ-LQGGFDGYARGAQQLASAAGAGAGAS    149
NP_062191.1       101   LNPEALGFSPEDAVEALISNSHQ-LQGGFDGYARGAQQLAAAAGAGAGAS    149
NP_001020748.2    101   LNPEALGFSPEDAVEALISNSHQ-LQGGFDGYARGAQQLAAAAGAGAGAS    149

NP_001038136.1    147   ---PAEEMGSAAAVVSAVIAAAAAQGGA-PHYHHHHHHPHHGGGGGGGH    192
NP_571919.1       147   ---AGEEMGSAAAVVSAVIAAAAAQNGA-PHHHHHHHHH------GHHQQ    186
XP_003201520.1    147   ---AGEEMGSAAAVVSAVIAAAAAQNGA-PHHHHHHHHHH---PAGHHHH    189
NP_005351.2       150   LGGSGEEMGPAAAVVSAVIAAAAAQSGAGPHY--HHHHHH---AAGHHHH    194
XP_511123.2       150   LGGSGEEMGPAAAVVSAVIAAAAAQSGAGPHY--HHHHHH---AAGHHHH    194
NP_001099107.1    150   LGGSGEEMGPAAAVVSAVIAAAAAQSGAAPHYHHHHHHHH---AAGHHHH    196
NP_062191.1       150   LGGSGEEMGPAAAVVSAVIAAAAAQSGGAPHY--HHHHHH---ATGHHHH    194
NP_001020748.2    150   LGGSGEEMGPAAAVVSAVIAAAAAQSGAAPHY--HHHHHH---AAGHHHH    194
```

```
Protein Acc.        Gene    Organism
NP_005351.2  MAF    H.sapiens
XP_511123.2  MAF    P.troglodytes
NP_001099107.1      MAF     B.taurus
NP_001020748.2      Maf     M.musculus
NP_062191.1  Maf    R.norvegicus
NP_001038136.1      MAF     G.gallus
XP_003201520.1      LOC100537332      D.rerio
NP_571919.1  maf    D.rerio
```

INB-1-11-8 (H1) Heavy Chain (SEQ ID NO: 16)
5'3' Frame 1
METGLRWLLLVAVLKGVQCQSLEESGGRLVTPGTPLTLTCTASGFSLNNYPMTWVRQAPG
KGLDYIGVINNSGETAYATWAKRRFTISRTSTTLYLKIASPTIEDTATYFCARGGPVSSD
MWGPGTLVIVSSGQPKAPSVFPLAPCCGDTPSSTVTLGCLVKGYLPEPVTVTWNSGTLTN
GVRTFPSVRQSSGLYSLSSVVSVTSSSQPVTCNVAHPATNTKVDKTVAPSTCSKPTCPPP
ELLGGPSVFIFPPKPKDTLMISRTPEVTCVVVDVSQDDPEVQFTWYINNEQVRTARPPLR
EQQFNSTIRVVSTLPIAHQDWLRGKEFKCKVHNKALPAPIEKTISKARGQPLEPKVYTMG
PPREELSSRSVSLTCMINGFYPSDISVEWEKNGKAEDNYKTTPAVLDSDGSYFLYSKLSV
PTSEWQRGDVFTCSVMHEALHNHYTQKSISRSPGK Legend:
GQPKAP: Start of constant region
GCG...AGC Variant

INB-1-11-8 (L4) Light chain (SEQ ID NO: 20)
5'3' Frame 1
MDTRAPTQLLGLLLLWLPGATFAQVLTQTASPVSAVVGGTVTINCQSSQSVYRGDWLAWY
QQRPGQPPKLLIYGASTLASGVPSRFKGSGSGTHFTLTISDLDCDDAATYYCAGGFSGHI
YDFGGGTEVVVKGDPVAPTVLIFPPAADQVATGTVTIVCVANKYFPDVTVTWEVDGTTQT
TGIENSKTPQNSADCTYNLSSTLTLTSTQYNSHKEYTCKVTQGTTSVVQSFNRGDC Legend:
DPVAPT: Start of constant region
GCTGCTGATCAG : Variant

Figure 8.

| Variable | MAF IHC negative (n=284) | | MAF IHC Postive (n=39) | | Total (n=323) | | p-value |
|---|---|---|---|---|---|---|---|
| Bone Mx | 277 | | 39 | | 316 | | |
| Non Bone Mx | 273 | (98.6%) | 19 | (48.7%) | 292 | (92.4%) | <.001 C |
| Bone Mx | 4 | (1.4%) | 20 | (51.3%) | 24 | (7.6%) | |
| Age | 275 | | 36 | | 311 | | |
| Mean | 57.1 | | 60.9 | | 57.6 | | 0.055 K |
| Median | 57.0 | | 63.5 | | 58.0 | | |
| Grade | 282 | | 39 | | 321 | | |
| 1 | 43 | (15.2%) | 4 | (10.3%) | 47 | (14.6%) | 0.448 C |
| 2 | 137 | (48.6%) | 23 | (59.0%) | 160 | (49.8%) | |
| 3 | 102 | (36.2%) | 12 | (30.8%) | 114 | (35.5%) | |
| pT | 282 | | 39 | | 321 | | |
| 1 | 172 | (61.0%) | 16 | (41.0%) | 188 | (58.6%) | <.001 C |
| 2 | 91 | (32.3%) | 13 | (33.3%) | 104 | (32.4%) | |
| 3 | 19 | (6.7%) | 10 | (25.6%) | 29 | (9.0%) | |
| pN | 282 | | 39 | | 321 | | |
| 0 | 169 | (59.9%) | 18 | (46.2%) | 187 | (58.3%) | |
| 1 | 79 | (28.0%) | 8 | (20.5%) | 87 | (27.1%) | 0.002 C |
| 2 | 24 | (8.5%) | 7 | (17.9%) | 31 | (9.7%) | |
| 3 | 10 | (3.5%) | 6 | (15.4%) | 16 | (5.0%) | |
| St Gallen | 284 | | 39 | | 323 | | |
| Luminal A | 148 | (52.1%) | 19 | (48.7%) | 167 | (51.7%) | |
| Luminal B HER2- | 32 | (11.3%) | 6 | (15.4%) | 38 | (11.8%) | 0.831 C |
| Luminal B HER2+ | 43 | (15.1%) | 4 | (10.3%) | 47 | (14.6%) | |
| HER2 | 16 | (5.6%) | 3 | (7.7%) | 19 | (5.9%) | |
| TN | 45 | (15.8%) | 7 | (17.9%) | 52 | (16.1%) | |
| Last event | 277 | | 39 | | 316 | | |
| Free of disease | 238 | (85.9%) | 19 | (48.7%) | 257 | (81.3%) | <.001 C |
| Alive with disease | 14 | (5.1%) | 8 | (20.5%) | 22 | (7.0%) | |
| Dead | 25 | (9.0%) | 12 | (30.8%) | 37 | (11.7%) | |
| Relapse | 277 | | 39 | | 316 | | |
| No | 235 | (84.8%) | 17 | (43.6%) | 252 | (79.7%) | <.001 C |
| Yes | 42 | (15.2%) | 22 | (56.4%) | 64 | (20.3%) | |
| Family History | | | | | | | |
| n | 109 | | 26 | | 135 | | 0.803 C |
| No | 90 | (82.6%) | 22 | (84.6%) | 112 | (83.0%) | |
| Yes | 19 | (17.4%) | 4 | (15.4%) | 23 | (17.0%) | |

K = Kruskal-Wallis; C=Chi-square test

Figure 10.

```
                        SEQUENCE LISTING

<160> NUMBER OF SEQ ID NOS: 47

<210> SEQ ID NO 1
<211> LENGTH: 6878
<212> TYPE: DNA
<213> ORGANISM: Homo sapiens

<400> SEQUENCE: 1
agaggcttta aaatctttt tcatcttcta gctgtagctc gggctgcttg tcggcttggc      60
ctccccctcc cccctttgct ctctgcctcg tctttcccca ggacttcgct attttgcttt    120
tttaaaaaaa ggcaagaaag aactaaactc ccccctccct ctcctccagt cgggctgcac    180
ctctgccttg cactttgcac agaggtagag agcgcgcgag ggagagagag gaaagaaaaa    240
aaataataaa gagagccaag cagaagagga ggcgagaagc atgaagtgtt aactccccg    300 tgccaaggcc cgcgccgccc ggacagacgc ccgccgcgcc tccagccccg agcggacgcc    360
gcgcgcgccc tgcctgcagc ccgggccggc gaggcgagcc cttccttatg caaagcgcgc    420
agcggagcgg cgagcgggg acgccgcgca ccgggccggg ctcctccagc ttcgccgccg    480
cagccaccac cgccgccacc gcagctcgcg gaggatcttc ccgagcctga agccgccggc    540
tcggcgcgca aggaggcgag cgagcaagga ggggccgggg cgagcgaggg agcacattgg    600
cgtgagcagg ggggaggag ggcgggcgcg ggggcgcgg gcagggcggg ggggtgtgtg     660
tgtgagcgcg ctcggaggtt tcgggccagc caccgccgcg caagctagaa gcgcccagc    720 ccggcaagct ggctcacccg ctggccaccc agcacagccc gctggcccct ctcctgcagc    780
ccatctggcg gagcggcggc ggcggcggcg gcggcggcag gagaatggca tcagaactgg    840
caatgagcaa ctccgacctg cccaccagtc ccctggccat ggaatatgtt aatgacttcg    900
atctgatgaa gtttgaagtg aaaaaggaac cggtggagac cgaccgcatc atcagccagt    960
gcggccgtct catcgccggg ggctcgctgt cctccacccc catgagcacg ccgtgcagct   1020
cggtgccccc ttcccccagc ttctcggcgc ccagcccggg ctcgggcagc gagcagaagg   1080
cgcacctgga agactactac tggatgaccg gctaccgca gcagctgaac cccgaggcgc   1140
tgggcttcag ccccgaggac gcggtcgagg cgctcatcag caacagccac cagctccagg   1200
gcggcttcga tggctacgcg cgcggggcgc agcagctggc cgcggcggcc ggggccggtg   1260
ccggcgcctc cttgggcggc agcggcgagg agatgggccc cgccgccgcc gtggtgtccg   1320
ccgtgatcgc cgcggccgcc gcgcagagcg gcgcgggccc gcactaccac caccaccacc   1380
accacgccgc cggccaccac caccacccga cggccggcgc gcccggcgcc gcgggcagcg   1440
cggccgcctc ggccggtggc gctggggcg cgggcggcgg tggcccggcc agcgctgggg   1500
gcggcggcgg cggcggcggc ggcggaggcg gcggggcgc ggcgggggcg gggcgcgccc   1560
tgcacccgca ccacgccgcc ggcggcctgc acttcgacga ccgcttctcc gacgagcagc   1620
```

```
tggtgaccat gtctgtgcgc gagctgaacc ggcagctgcg cggggtcagc aaggaggagg    1680
tgatccggct gaagcagaag aggcggaccc tgaaaaaccg cggctatgcc cagtcctgcc    1740
gcttcaagag ggtgcagcag agacacgtcc tggagtcgga agaaccag ctgctgcagc     1800 aagtcgacca cctcaagcag gagatctcca ggctggtgcg cgagagggac gcgtacaagg    1860
agaaatacga gaagttggtg agcagcggct tccgagaaaa cggctcgagc agcgacaacc    1920
cgtcctctcc cgagttttc atgtgagtct gacacgcgat tccagctagc caccctgata    1980
agtgctccgc gggggtccgg ctcgggtgtg ggcttgctag ttctagagcc atgctcgcca    2040
ccacctcacc accccaccc ccaccgagtt tggcccccctt ggcccccctac acacacacaa    2100 acccgcacgc acacaccaca cacacacaca cacacacaca cacacccac accctgctcg    2160 agtttgtggt ggtggtggct gttttaaact ggggagggaa tgggtgtctg gctcatggat    2220
tgccaatctg aaattctcca taacttgcta gcttgttttt tttttttttt tacacccccc    2280
cgccccaccc ccggacttgc acaatgttca atgatctcag cagagttctt catgtgaaac    2340
gttgatcacc tttgaagcct gcatcattca catatttttt cttcttcttc cccttcagtt    2400
catgaactgg tgttcatttt ctgtgtgtgt gtgtgttta ttttgtttgg attttttttt    2460 ttaatttac ttttagagct tgctgtgttg cccacctttt ttccaacctc caccctcact    2520
ccttctcaac ccatctcttc cgagatgaaa gaaaaaaaaa agcaaagttt ttttttcttc    2580
tcctgagttc ttcatgtgag attgagcttg caaaggaaaa aaaaatgtga atgttatag    2640 acttgcagcg tgccgagttc catcgggttt ttttttagc attgttatgc taaaatagag    2700
aaaaaaatcc tcatgaacct tccacaatca agcctgcatc aaccttctgg gtgtgacttg    2760
tgagttttgg ccttgtgatg ccaaatctga gagtttagtc tgccattaaa aaaactcatt    2820
ctcatctcat gcattattat gcttgctact ttgtcttagc aacaatgaac tataactgtt    2880
tcaaagactt tatggaaaag agacattata ttaataaaaa aaaaagcct gcatgctgga    2940 catgtatggt ataattattt ttttccttttt ttttcctttt ggcttggaaa tggacgttcg    3000
aagacttata gcatggcatt catacttttg ttttattgcc tcatgacttt tttgagttta    3060
gaacaaaaca gtgcaaccgt agagccttct tcccatgaaa ttttgcatct gctccaaaac    3120
tgctttgagt tactcagaac ttcaacctcc caatgcactg aaggcattcc ttgtcaaaga    3180
taccagaatg ggttacacat ttaacctggc aaacattgaa gaactcttaa tgttttcttt    3240
ttaataagaa tgacgcccca ctttggggac taaaattgtg ctattgccga gaagcagtct    3300
aaaatttatt ttttaaaaag agaaactgcc ccattatttt tggtttgttt tatttttatt    3360 ttatatttttt tggcttttgg tcattgtcaa atgtggaatg ctctgggttt ctagtatata    3420
atttaattct agttttttata atctgttagc ccagttaaaa tgtatgctac agataaagga    3480
atgttataga taaatttgaa agagttaggt ctgtttagct gtagattttt taaacgattg    3540
atgcactaaa ttgttactta ttgtgatgtt aaggggggta gagtttgcaa ggggactgtt    3600 taaaaaagt agcttataca gcatgtgctt gcaacttaaa tataagttgg gtatgtgtag    3660
tctttgctat accactgact gtattgaaaa ccaaagtatt aagagggaa acgcccctgt    3720 ttatatctgt aggggtattt tacattcaaa aatgtatgtt ttttttttcttt ttcaaaatta    3780 aagtatttgg gactgaattg cactaagata taacctgcaa gcatataata caaaaaaaaa    3840
ttgcaaaact gtttagaacg ctaataaaat ttatgcagtt ataaaaatgg cattactgca    3900
cagttttaag atgatgcaga tttttttaca gttgtattgt ggtgcagaac tggatttttct    3960 gtaacttaaa aaaaaatcca cagttttaaa ggcaataatc agtaaatgtt attttcaggg    4020
```

```
actgacatcc tgtctttaaa aagaaatgaa aagtaaatct taccacaata aatataaaaa    4080
aatcttgtca gttactttc ttttacatat tttgctgtgc aaaattgttt tatatcttga     4140
gttactaact aaccacgcgt gttgttccta tgtgcttttc tttcattttc aattctggtt    4200
atatcaagaa aagaataatc tacaataata acggcatttt tttttgatt ctgtactcag     4260 tttcttagtg tacagtttaa ctgggcccaa caacctcgtt aaaagtgtaa aatgcatcct    4320
tttctccagt ggaaggattc ctggaggaat agggagacag taattcaggg tgaaattata    4380
ggctgttttt tgaagtgagg aggctggccc catatactga ttagcaatat ttaatataga    4440
tgtaaattat gacctcattt ttttctcccc aaagttttca gttttcaaat gagttgagcc    4500
ataattgccc ttggtaggaa aaacaaaaca aaacagtgga actaggcttc ctgagcatgg    4560
ccctacactt ctgatcagga gcaaagccat ccatagacag aggagccgga caaatatggc    4620
gcatcagagg tggcttgcgc acatatgcat tgaacggtaa agagaaacag cgcttgcctt    4680
ttcactaaag ttgactattt ttccttcttc tcttacacac cgagattttc ttgttagcaa    4740
ggcctgacaa gatttaacat aaacatgaca aatcatagtt gtttgttttg ttttgctttt    4800
ctctttaaca ctgaagatca tttgtcttaa ataggaaaaa gaaatccac tccttacttc     4860 catatttcca agtacatatc tggtttaaac tatgttatca aatcatattt caccgtgaat    4920
attcagtgga gaacttctct acctggatga gctagtaatg atttcagatc atgctatccc    4980
cagaaataaa agcaaaaaat aatacctgtg tggaatatag gctgtgcttt gatttactgg    5040
tatttacccc aaaataggct gtgtatgggg gctgacttaa agatcccttg gaaagactca    5100
aaactacctt cactagtagg actcctaagc gctgacctat ttttaaatga cacaaattca    5160
tgaaactaat gttacaaatt catgcagttt gcactcttag tcatcttccc ctagcacacc    5220
aatagaatgt tagacaaagc cagcactgtt ttgaaaatac agccaaacac gatgactttt    5280
gttttgtttt ctgccgttct taaaagaaaa aagataata ttgcaactct gactgaaaga     5340
cttattttta agaaaacagg ttgtgtttgg tgctgctaag ttctggccag tttatcatct    5400
ggccttcctg cctattttt acaaaacacg aagacagtgt gtaacctcga cattttgacc     5460
ttcctttatg tgctagttta gacaggctcc tgaatccaca cttaattttg cttaacaaaa    5520
gtcttaatag taaacctccc ctcatgagct tgaagtcaag tgttcttgac ttcagatatt    5580
tctttccttt tttttttttt ttcctcatca caactaagag atacacaaac tctgaagaag    5640
cagaaatgga gagaatgctt ttaacaaaaa agcatctgat gaaagatttt aggcaaacat    5700
tctcaaaata agagtgatat tctggatgta gttattgcag ttatctcatg acaaatgagg    5760
cctggattgg aaggaaaata tagttgtgta gaattaagca ttttgatagg aatctacaag    5820
gtagttgaat ataataagca ggtttgggcc cccaaacttt agaaaatcaa atgcaaaggt    5880
gctggcaaaa atgaggtttg agtggctggc tgtaagagaa ggttaactcc tagtaaaagg    5940
catttttaga aataacaatt actgaaaact ttgaagtata gtgggagtag caaacaaata    6000
catgtttttt ttttcttaca aagaactcct aaatcctgag taagtgccat tcattacaat    6060
aagtctctaa atttaaaaaa aaaaaaatca tatgaggaaa tctagctttc cccttttacgc   6120 tgcgtttgat ctttgtctaa atagtgttaa aattcctttc attccaatta cagaactgag    6180
cccactcgca agttggagcc atcagtggga tacgccacat tttggaagcc ccagcatcgt    6240
gtacttacca gtgtgttcac aaaatgaaat ttgtgtgaga gctgtacatt aaaaaaaatc    6300
atcattatta ttattatttg cagtcatgga gaaccaccta cccctgactt ctgtttagtc    6360
```

-continued

| | |
|---|---|
| tcctttttaa ataaaaatta ctgtgttaga gaagaaggct attaaatgta gtagttaact | 6420 |
| atgcctcttg tctgggggtt tcatagagac cggtaggaaa gcgcactcct gcttttcgat | 6480 |
| ttatggtgtg tgcaagtaaa caggtgcatt gctttcaacc tgccatacta gttttaaaaa | 6540 |
| ttcactgaaa ttacaaagat acatatatat gcatatatat aatggaaagt ttcccggaat | 6600 |
| gcaacaatta gcattttaaa atcatatata ggcatgcaca ttctaaatag tactttttca | 6660 |
| tgcttcattg tttctctggc agataatttt actaagaaga aaaatagata ttcgactccc | 6720 |
| cttccctaaa caaatccacg ggcagaggct ccagcggagc cgagccccct ggttttctcg | 6780 |
| taggccctag acggtgttgc atttatcagt gatgtcaaac gtgctcattt gtcagacata | 6840 |
| gctgtaaatg aaacaatgt gtggcaaaat acaaagtt | 6878 |

<210> SEQ ID NO 2
<211> LENGTH: 2656
<212> TYPE: DNA
<213> ORGANISM: Homo sapiens

<400> SEQUENCE: 2

| | |
|---|---|
| gaggctttaa aatcttttttt catcttctag ctgtagctcg ggctgcttgt cggcttggcc | 60 |
| tcccctccc ccctttgctc tctgcctcgt cttccccag gacttcgcta ttttgctttt | 120 |
| ttaaaaaag gcaagaaaga actaaactcc cccctccctc tcctccagtc gggctgcacc | 180 |
| tctgccttgc actttgcaca gaggtagaga gcgcgcgagg gagagagagg aaagaaaaaa | 240 |
| aataataaag agagccaagc agaagaggag gcgagaagca tgaagtgtta actccccgt | 300 |
| gccaaggccc gcgccgcccg gacagacgcc cgccgcgcct ccagccccga gcggacgccg | 360 |
| cgcgcgccct gcctgcagcc cgggccggcg aggcgagccc ttccttatgc aaagcgcgca | 420 |
| gcggagcggc gagcggggga cgccgcgcac cgggccgggc tcctccagct tcgccgccgc | 480 |
| agccaccacc gccgccaccg cagctcgcgg aggatcttcc cgagcctgaa gccgccggct | 540 |
| cggcgcgcaa ggaggcgagc gagcaaggag gggccggggc gagcgaggga gcacattggc | 600 |
| gtgagcaggg gggagggagg gcgggcgcgg ggggcgcggg cagggcgggg gggtgtgtgt | 660 |
| gtgagcgcgc tcggaggttt cgggccagcc accgccgcgc aagctagaag cgccccagcc | 720 |
| cggcaagctg gctcacccgc tggccaccca gcacagcccg ctggccccctc tcctgcagcc | 780 |
| catctggcgg agcggcggcg gcggcggcgg cggcggcagg agaatggcat cagaactggc | 840 |
| aatgagcaac tccgacctgc ccaccagtcc cctggccatg gaatatgtta atgacttcga | 900 |
| tctgatgaag tttgaagtga aaaaggaacc ggtggagacc gaccgcatca tcagccagtg | 960 |
| cggccgtctc atcgccgggg gctcgctgtc ctccaccccc atgagcacgc cgtgcagctc | 1020 |
| ggtgcccccct tcccccagct tctcggcgcc cagcccgggc tcgggcagcg agcagaaggc | 1080 |
| gcacctggaa gactactact ggatgaccgg ctacccgcag cagctgaacc ccgaggcgct | 1140 |
| gggcttcagc cccgaggacg cggtcgaggc gctcatcagc aacagccacc agctccaggg | 1200 |
| cggcttcgat ggctacgcgc gcggggcgca gcagctggcc gcggcggccg ggccggtgc | 1260 |
| cggcgcctcc ttgggcggca gcgcgagga gatgggcccc gccgccgccg tggtgtccgc | 1320 |
| cgtgatcgcc gcggccgccg cgcagagcgg cgcgggcccg cactaccacc accaccacca | 1380 |
| ccacgccgcc ggccaccacc acaccccgac ggccggcgcg cccggccgcg cgggcagcgc | 1440 |
| ggccgcctcg gccggtggcg ctggggcgc gggcggcggt ggcccggcca gcgctggggg | 1500 |
| cggcggcggc ggcggcggcg gcggaggcgg cggggggcgcg gcggggggcgg gggggcgccct | 1560 |
| gcacccgcac cacgccgccg gcggcctgca cttcgacgac gcgcttctccg acgagcagct | 1620 |

```
ggtgaccatg tctgtgcgcg agctgaaccg gcagctgcgc ggggtcagca aggaggaggt    1680
gatccggctg aagcagaaga ggcggaccct gaaaaaccgc ggctatgccc agtcctgccg    1740
cttcaagagg gtgcagcaga gacacgtcct ggagtcggag aagaaccagc tgctgcagca    1800
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttttca taactgagcc cactcgcaag ttggagccat cagtgggata    1980
cgccacattt tggaagcccc agcatcgtgt acttaccagt gtgttcacaa aatgaaattt    2040
gtgtgagagc tgtacattaa aaaaaatcat cattattatt attatttgca gtcatggaga    2100
accacctacc cctgacttct gtttagtctc ctttttaaat aaaaattact gtgttagaga    2160
agaaggctat taaatgtagt agttaactat gcctcttgtc tgggggtttc atagagaccg    2220
gtaggaaagc gcactcctgc ttttcgattt atggtgtgtg caagtaaaca ggtgcattgc    2280
tttcaacctg ccatactagt tttaaaaatt cactgaaatt acaaagatac atatatatgc    2340
atatatataa tggaaagttt cccggaatgc aacaattagc attttaaaat catatatagg    2400
catgcacatt ctaaatagta cttttttcatg cttcattgtt tctctggcag ataattttac    2460
taagaagaaa aatagatatt cgactcccct tccctaaaca aatccacggg cagaggctcc    2520
agcggagccg agcccctgg ttttctcgta ggccctagac ggtgttgcat ttatcagtga    2580
tgtcaaacgt gctcatttgt cagacatagc tgtaaatgaa acaatgtgt ggcaaaatac    2640 aaagttaaaa aaaaaa                                                   2656

<210> SEQ ID NO 3
<211> LENGTH: 6887
<212> TYPE: DNA
<213> ORGANISM: Homo sapiens

<400> SEQUENCE: 3
gaggctttaa aatctttttt catcttctag ctgtagctcg ggctgcttgt cggcttggcc      60
tccccctccc cccttttgctc tctgcctcgt cttttccccag gacttcgcta ttttgctttt     120
ttaaaaaaag gcaagaaaga actaaactcc ccctcccctc tcctccagtc gggctgcacc     180
tctgccttgc actttgcaca gaggtagaga gcgcgcgagg gagagagagg aaagaaaaaa     240
aataataaag agagccaagc agaagaggag gcgagaagca tgaagtgtta actccccgt      300 gccaaggccc gcgccgcccg gacagacgcc cgccgcgcct ccagccccga gcggacgccg     360
cgcgcgccct gcctgcagcc cgggccggcg aggcgagccc ttccttatgc aaagcgcgca     420
gcggagcggc gagcggggga cgccgcgcac cgggccgggc tcctccagct tcgccgccgc     480
agccaccacc gccgccaccg cagctcgcgg aggatcttcc cgagcctgaa gccgccggct     540
cggcgcgcaa ggaggcgagc gagcaaggag gggccggggc gagcgaggga gcacattggc     600
gtgagcaggg gggagggagg gcgggcgcgg ggggcgcggg cagggcgggg gggtgtgtgt     660
gtgagcgcgc tcggaggttt cgggccagcc accgccgcgc aagctagaag cgccccagcc     720
cggcaagctg gctcacccgc tggccaccca gcacagcccg ctggcccctc tcctgcagcc     780
catctggcgg agcggcggcg gcggcggcgg cggcggcagg agaatggcat cagaactggc     840
aatgagcaac tccgacctgc ccaccagtcc cctggccatg gaatatgtta atgacttcga     900
tctgatgaag tttgaagtga aaaggaacc ggtggagacc gaccgcatca tcagccagtg     960
cggccgtctc atcgccgggg gctcgctgtc ctccaccccc atgagcacgc cgtgcagctc    1020
```

```
ggtgcccect tecccagct tctcggcgcc cagcccgggc tcgggcagcg agcagaaggc    1080
gcacctggaa gactactact ggatgaccgg ctacccgcag cagctgaacc ccgaggcgct    1140
gggcttcagc cccgaggacg cggtcgaggc gctcatcagc aacagccacc agctccaggg    1200
cggcttcgat ggctacgcgc gcggggcgca gcagctggcc gcggcggccg gggcggtgc    1260
cggcgcctcc ttgggcggca gcggcgagga gatgggcccc gccgccgccg tggtgtccgc    1320
cgtgatcgcc gcggccgccg cgcagagcgg cgcgggcccg cactaccacc accaccacca    1380
ccacgccgcc ggccaccacc accccgac ggccggcgcg cccggcgccg cgggcagcgc     1440
ggccgcctcg gccggtggcg ctgggggcgc gggcggcggt ggcccggcca gcgctggggg    1500
cggcggcggc ggcggcggcg gcgaggcgg cggggcgcg gcggggcgg ggggcgccct      1560
gcacccgcac cacgccgccg gcggcctgca cttcgacgac cgcttctccg acgagcagct    1620
ggtgaccatg tctgtgcgcg agctgaaccg gcagctgcgc ggggtcagca aggaggaggt    1680
gatccggctg aagcagaaga ggcggaccct gaaaaaccgc ggctatgccc agtcctgccg    1740
cttcaagagg gtgcagcaga gacacgtcct ggagtcggaa aagaaccagc tgctgcagca    1800
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttca tgtgagtctg acacgcgatt ccagctagcc accctgataa    1980
gtgctccgcg ggggtccggc tcgggtgtgg gcttgctagt tctagagcca tgctcgccac    2040
cacctcacca cccccacccc caccgagttt ggccccttg gcccctaca cacacaaa      2100
cccgcacgca cacaccacac acacacacac acacacacac acaccccaca ccctgctcga    2160
gtttgtggtg gtggtggctg tttaaactg gggagggaat gggtgtctgg ctcatggatt    2220
gccaatctga aattctccat aacttgctag cttgttttt tttttttttt acacccccc     2280
gccccacccc cggacttgca caatgttcaa tgatctcagc agagttcttc atgtgaaacg    2340
ttgatcacct ttgaagcctg catcattcac atatttttc ttcttcttcc ccttcagttc    2400
atgaactggt gttcatttc tgtgtgtgtg tgtgttat tttgtttgga ttttttttt       2460
taatttact tttagagctt gctgtgttgc ccaccttttt tccaacctcc accctcactc    2520
cttctcaacc catctcttcc gagatgaaag aaaaaaaaa gcaaagtttt tttttcttct    2580
cctgagttct tcatgtgaga ttgagcttgc aaaggaaaaa aaaatgtgaa atgttataga    2640
cttgcagcgt gccgagttcc atcgggtttt tttttagca ttgttatgct aaaatagaga    2700
aaaaaatcct catgaacctt ccacaatcaa gcctgcatca accttctggg tgtgacttgt    2760
gagttttggc cttgtgatgc caaatctgag agtttagtct gccattaaaa aaactcattc    2820
tcatctcatg cattattatg cttgctactt tgtcttagca acaatgaact ataactgttt    2880
caaagacttt atggaaaaga gacattatat taataaaaaa aaaagcctg catgctggac     2940
atgtatggta taattatttt ttccttttt tttcctttg gcttggaaat ggacgttcga    3000
agacttatag catggcattc atactttgt tttattgcct catgactttt ttgagtttag    3060
aacaaaacag tgcaaccgta gagccttctt cccatgaaat tttgcatctg ctccaaaact    3120
gctttgagtt actcagaact tcaacctccc aatgcactga aggcattcct tgtcaaagat    3180
accagaatgg gttacacatt taacctggca aacattgaag aactcttaat gttttctttt    3240
taataagaat gacgccccac tttgggggact aaaattgtgc tattgccgag aagcagtcta    3300
aaatttattt tttaaaaaga gaaactgccc cattattttt ggttttgttt atttttattt    3360
tatatttttt ggcttttggt cattgtcaaa tgtggaatgc tctgggtttc tagtatataa    3420
```

```
tttaattcta gttttataa tctgttagcc cagttaaaat gtatgctaca gataaaggaa    3480
tgttatagat aaatttgaaa gagttaggtc tgtttagctg tagatttttt aaacgattga    3540
tgcactaaat tgtttactat tgtgatgtta agggggtag agtttgcaag gggactgttt     3600
aaaaaaagta gcttatacag catgtgcttg caacttaaat ataagttggg tatgtgtagt    3660
ctttgctata ccactgactg tattgaaaac caaagtatta agaggggaaa cgcccctgtt    3720
tatatctgta ggggtatttt acattcaaaa atgtatgttt ttttttcttt tcaaaattaa    3780
agtatttggg actgaattgc actaagatat aacctgcaag catataatac aaaaaaaaat   3840
tgcaaaactg tttagaacgc taataaaatt tatgcagtta taaaaatggc attactgcac    3900
agttttaaga tgatgcagat tttttacag ttgtattgtg gtgcagaact ggattttctg     3960
taacttaaaa aaaatccac agttttaaag gcaataatca gtaaatgtta ttttcaggga     4020
ctgacatcct gtctttaaaa agaaatgaaa agtaaatctt accacaataa atataaaaaa    4080
atcttgtcag ttacttttct tttacatatt tgctgtgca aaattgtttt atatcttgag     4140
ttactaacta accacgcgtg ttgttcctat gtgcttttct ttcattttca attctggtta    4200
tatcaagaaa agaataatct acaataataa acggcatttt tttttgattc tgtactcagt    4260
ttcttagtgt acagtttaac tgggcccaac aacctcgtta aaagtgtaaa atgcatcctt    4320
ttctccagtg aaggattcc tggaggaata gggagacagt aattcagggt gaaattatag     4380 gctgttttt gaagtgagga ggctggcccc atatactgat tagcaatatt taatatagat     4440
gtaaattatg acctcatttt tttctcccca aagttttcag ttttcaaatg agttgagcca    4500
taattgccct tggtaggaaa acaaaacaa aacagtggaa ctaggcttcc tgagcatggc     4560
cctacacttc tgatcaggag caaagccatc catagacaga ggagccggac aaatatggcg    4620
catcagaggt ggcttgcgca catatgcatt gaacggtaaa gagaaacagc gcttgccttt    4680
tcactaaagt tgactatttt tccttcttct cttacacacc gagatttct tgttagcaag     4740 gcctgacaag atttaacata aacatgacaa atcatagttg tttgttttgt tttgcttttc    4800
tctttaacac tgaagatcat ttgtcttaaa taggaaaaag aaaatccact ccttacttcc    4860
atatttccaa gtacatatct ggtttaaact atgttatcaa atcatatttc accgtgaata    4920
ttcagtggag aacttctcta cctggatgag ctagtaatga tttcagatca tgctatcccc    4980
agaaataaaa gcaaaaata atacctgtgt ggaatatagg ctgtgctttg atttactggt    5040 atttaccccca aaataggctg tgtatggggg ctgacttaaa gatcccttgg aaagactcaa    5100
aactaccttc actagtagga ctcctaagcg ctgacctatt tttaaatgac acaaattcat    5160
gaaactaatg ttacaaattc atgcagtttg cactcttagt catcttcccc tagcacacca    5220
atagaatgtt agacaaagcc agcactgttt tgaaaataca gccaaacacg atgacttttg    5280
ttttgttttc tgccgttctt aaaagaaaaa aagataatat tgcaactctg actgaaagac    5340
ttatttttaa gaaaacaggt tgtgtttggt gctgctaagt tctggccagt ttatcatctg    5400
gccttcctgc ctatttttta caaaacacga agacagtgtg taacctcgac attttgacct    5460
tcctttatgt gctagtttag acaggctcct gaatccacac ttaattttgc ttaacaaaag    5520
tcttaatagt aaacctcccc tcatgagctt gaagtcaagt gttcttgact tcagatattt    5580 ctttccttt ttttttttt tcctcatcac aactaagaga tacacaaact ctgaagaagc      5640
agaaatggag agaatgcttt taacaaaaaa gcatctgatg aaagatttta ggcaaacatt    5700
ctcaaaataa gagtgatatt ctggatgtag ttattgcagt tatctcatga caaatgaggc    5760
```

```
ctggattgga aggaaaatat agttgtgtag aattaagcat tttgatagga atctacaagg   5820
tagttgaata taataagcag gtttgggccc ccaaacttta gaaaatcaaa tgcaaaggtg   5880
ctggcaaaaa tgaggtttga gtggctggct gtaagagaag gttaactcct agtaaaaggc   5940 attttagaa ataacaatta ctgaaaactt tgaagtatag tgggagtagc aaacaaatac    6000 atgtttttt tttcttacaa agaactccta aatcctgagt aagtgccatt cattacaata    6060
agtctctaaa tttaaaaaaa aaaaaatcat atgaggaaat ctagcttttc cctttacgct   6120
gcgtttgatc tttgtctaaa tagtgttaaa attcctttca ttccaattac agaactgagc   6180
ccactcgcaa gttggagcca tcagtgggat acgccacatt ttggaagccc cagcatcgtg   6240
tacttaccag tgtgttcaca aatgaaatt tgtgtgagag ctgtacatta aaaaaaatca    6300
tcattattat tattatttgc agtcatggag aaccacctac ccctgacttc tgtttagtct   6360 ccttttaaa taaaaattac tgtgttagag aagaaggcta ttaaatgtag tagttaacta   6420
tgcctcttgt ctgggggttt catagagacc ggtaggaaag cgcactcctg cttttcgatt   6480
tatggtgtgt gcaagtaaac aggtgcattg ctttcaacct gccatactag ttttaaaaat   6540
tcactgaaat tacaaagata catatatatg catatatata atggaaagtt tcccggaatg   6600
caacaattag cattttaaaa tcatatatag gcatgcacat tctaaatagt acttttcat    6660 gcttcattgt ttctctggca gataatttta ctaagaagaa aaatagatat tcgactcccc   6720
ttccctaaac aaatccacgg gcagaggctc cagcggagcc gagcccctg gttttctcgt    6780 aggccctaga cggtgttgca tttatcagtg atgtcaaacg tgctcatttg tcagacatag   6840
ctgtaaatga aacaatgtg tggcaaaata caaagttaaa aaaaaa                   6887
```

<210> SEQ ID NO 4
<211> LENGTH: 403
<212> TYPE: PRT
<213> ORGANISM: Homo sapiens

<400> SEQUENCE: 4

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
                20                  25                  30

Lys Lys Glu Pro Val Glu Thr Asp Arg Ile Ile Ser Gln Cys Gly Arg
            35                  40                  45

Leu Ile Ala Gly Gly Ser Leu Ser Ser Thr Pro Met Ser Thr Pro Cys
        50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
    130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala
        195                 200                 205

Ser Ala Gly Gly Ala Gly Ala Gly Gly Gly Pro Ala Ser Ala
    210                 215                 220

Gly Gly Gly Gly Gly Gly Gly Gly Gly Gly Gly Gly Ala Ala
225                 230                 235                 240

Gly Ala Gly Gly Ala Leu His Pro His Ala Ala Gly Gly Leu His
                245                 250                 255

Phe Asp Asp Arg Phe Ser Asp Glu Gln Leu Val Thr Met Ser Val Arg
        260                 265                 270

Glu Leu Asn Arg Gln Leu Arg Gly Val Ser Lys Glu Glu Val Ile Arg
    275                 280                 285

Leu Lys Gln Lys Arg Arg Thr Leu Lys Asn Arg Gly Tyr Ala Gln Ser
    290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
        340                 345                 350

Ser Ser Gly Phe Arg Glu Asn Gly Ser Ser Ser Asp Asn Pro Ser Ser
    355                 360                 365

Pro Glu Phe Phe Ile Thr Glu Pro Thr Arg Lys Leu Glu Pro Ser Val
370                 375                 380

Gly Tyr Ala Thr Phe Trp Lys Pro Gln His Arg Val Leu Thr Ser Val
385                 390                 395                 400

Phe Thr Lys

<210> SEQ ID NO 5
<211> LENGTH: 373
<212> TYPE: PRT
<213> ORGANISM: Homo sapiens

<400> SEQUENCE: 5

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
            20                  25                  30

Lys Lys Glu Pro Val Glu Thr Asp Arg Ile Ile Ser Gln Cys Gly Arg
        35                  40                  45

Leu Ile Ala Gly Gly Ser Leu Ser Ser Thr Pro Met Ser Thr Pro Cys
    50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Ala Gly Ala
    130                 135                 140

Gly Ala Gly Ala Ser Leu Gly Gly Ser Gly Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Gly Ser Ala Ala Ala
        195                 200                 205

Ser Ala Gly Gly Ala Gly Ala Gly Gly Gly Pro Ala Ser Ala
    210                 215                 220

Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Glu Val Ile Arg
                275                 280                 285

Leu Lys Gln Lys Arg Arg Thr Leu Lys Asn Arg Gly Tyr Ala Gln Ser
290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
        355                 360                 365

Pro Glu Phe Phe Met
    370

<210> SEQ ID NO 6
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 6
acggcucgag cagcgacaa                                                    19

<210> SEQ ID NO 7
<211> LENGTH: 19
<212> TYPE: RNA
<213> ORGANISM: Artificial Sequence
<220> FEATURE:
<223> OTHER INFORMATION: c-MAF specific siRNA

<400> SEQUENCE: 7
cuuaccagug uguucacaa                                                    19

<210> SEQ ID NO 8
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 8

-continued

| uggaagacua cuacuggaug | 20 |

<210> SEQ ID NO 9
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 9

| auuugcaguc auggagaacc | 20 |

<210> SEQ ID NO 10
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 10

| caaggagaaa uacgagaagu | 20 |

<210> SEQ ID NO 11
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 11

| acaaggagaa auacgagaag | 20 |

<210> SEQ ID NO 12
<211> LENGTH: 20
<212> TYPE: RNA
<213> ORGANISM: Artificial Sequence
<220> FEATURE:
<223> OTHER INFORMATION: c-MAF specific siRNA

<400> SEQUENCE: 12

| accuggaaga cuacuacugg | 20 |

<210> SEQ ID NO 13
<211> LENGTH: 13878
<212> TYPE: DNA
<213> ORGANISM: Homo sapiens

<400> SEQUENCE: 13

| aactatatat taaacacctc cggtctgaga ggccgtgttg ggtgtctttg tcaggtgaag | 60 |
| aaagagaaga aggctggtac accttcccag gaattctcac tgaagaaaac atctggattt | 120 |
| tttacatctc ttgtgcaaaa caaacaaaga tttcattaag tgatgtatat tgttttccaa | 180 |
| ggaagaaacc tgcagagaca aaaacaaata agcaaataat tgaaacaaaa atatgataaa | 240 |
| cccccaaatt cttccagtgc taatttactt gttatcatgg ttctctacaa aggcagagat | 300 |
| cactaattac aggttttttcc agaattcaca tttcacgtca agatcatcca atccaaacag | 360 |
| tgtacggaaa gcctagggcc ttcttcactt gccccctac cccacccctac acacacgccc | 420 |
| ccatctaaat gatacccttg gaaagaaacc tacacatctc atttgtctat attttgcttc | 480 |
| ctccctcgcc tcccggtaac caaatgtgag ttgttctcta actgcactgg agaatcagaa | 540 |
| tttattgtac atatgtttgt gttccactta ataaaaaaac ctatatttta agataaactt | 600 |
| tgttagtaat tcatgaggta agtgactatt tatgctaatc aggcagaaat atattctcaa | 660 |

```
gcataatgca ttacataaat ttgaatgtaa aatgttcaat tatgaagtaa atacaggtaa      720
tgcaaataat aaattacctc taataaaaat tataaaagat gtgccttgaa agagagagcg      780
gctttaactt acaactgtga attgcttaaa gagaaaagaa ttaataaatg ctgaattact      840
ctgatgatta tttagcacat aattcaccta ttcataacga ctcctagtaa tcagactgtt      900
gtttcacatc ctccaacatg aggcaagact gtttcctcag caattttgcc cttatcagat      960
tatctcgtct gattctatta attttcttcc atgaatctgc taacagtgat ttgtgattta     1020
cttaccctgc taactgaaga ctgttaaaag gatttatcta acactggacc taagaacagt     1080
gtacgcctta tcgttcagtt actctgaaga actctttctc aaatcaattt agttggtttc     1140
atagtgaaat ttagtggaca ctggttagtt ctgccccata aaatcagccc ctaaacaaag     1200
agtccagaca ccatacctga tgcatcccat tctattcaga ttatggatgt ctgattccaa     1260
catgatatat ttgagttgct ataactcaca atcggggaaa atatattcct ttaagctttt     1320 aatcttgta atttggacat gaacaggggt tttgtttttc atttttgcat gaagtcatta     1380
tgtatgtact gacgtgaaac tataattgtg tttctgatgt tactgtgtca caatattcta     1440
tgcgatgtaa cccatgtcct cctccccctc acaaatctcc tataaatatt cattgctttc     1500
aaaaacttta atactactgg tccgaattgg tcaataatga caaatgcatg gtttctaaat     1560
tactgtatat tgttctacag agattactag agtatatata gcaaggggat gttaagcagt     1620
aagaaaacac agttcacatt gtatttggat tagattggct tggatagaag tgaaacaaac     1680
aatgttagca agaagtcta aagacatgtg gcccactgta attgtacaga atcaaaaacc     1740
tgaatagtac tcattaaaat gagagagctc aattgttata aaagaaatgc tgctaacaga     1800
gaactgtaaa tgtttagaca cccctgtgaa tcactaaata ataatgtaaa aaggataaaa     1860
atgagaatta agttataagc ctgagagcat tactgctaca catctaaaaa aataattctg     1920
atcctctctt ttttttttcc aagagaaaat gggcgactat aaaagacctt gcaataagag     1980
aaataaaaat accatgtctt cacagcagtg tacataaata aaccataaaa atgtgcagat     2040
aataatatat ttagctgccc aaacatgggc atttaatttc tagaaatgat atataacaat     2100
gtaacaatta gatactcagc catgaatgtg tatggcacag tcttcatcat tagcaaactt     2160
tgtgtataaa atattattta ttatttatta taatactgct ttcagaggca atgatcatac     2220
cttacagctt ttaacacaaa tatgatgcaa aaggattaaa agtatatcat aaacaaacaa     2280
taaattcttt ctaaatacac ttaaattcat attttacatg aaaatataa acttcctaca     2340 tttgtgacta ctgacttta aaaagaccta gaaaactatt gttacgggca atgttaaatg     2400
acataatgct tatgtaatgg aaagtgtgga ttttcctcta aataaactat aatcccttaa     2460
cttcattact agggaaaata ttgttaaaga gaaggaaagc aagggaattc tgctaggttg     2520
cataaatatt gacataatct tcactctttc ttccccaaac tggtaataga catagtttat     2580
tccacccaac aaaatgctct tataagacca aaactaccct tattaacaac ttctctgcag     2640
tcacgatgaa aagaaacact acttgtctga aaaataccga cagcgctgcc ttttcagat     2700 tagggtgtgc ctacgaatct tttgggaagt cttccattaa ggattcctgg gtttgctgaa     2760
actgaagtct actaggatca gagaaattaa cacaggtcta atatggtgca aggaacgagt     2820
gagagacacc tgaggttata aatagcaaag catgctgcgg ggtggggaag accattctga     2880
agtgcaatgt tcaagacgct ggcttaatat atgactaagt gtcagaagtc aggttttctg     2940
agaattactt tccagataaa caactttata gcactgcact taatcttact tactagagac     3000
```

```
atctcattta tcactgaatt acaagtaact ttaatccctat tgatattgcc ataaagcccg    3060
ttgaaaatcc atcctggcac ttttaaaggg tttgggccc tgttacatgg ggatcctctt    3120
gcaaaggtct cagccagaaa ttacaccccg agggtgtctg tatccctgg cctctttgtc    3180 aacaatcaag gagaagagga ggggcaaaaa tgatctctgc atctgccagc actttcttcg    3240
gcccctttcc tatagggtcg ggttctccca cttcagtcaa actaactttg tgtgtctctt    3300
tcctcctccc acactgggta accagctgct tttcacttca tcgacaaaac tggacacgga    3360
tcaatttcaa ctgacctttg ccgaaaggtg gcgctgttga ggtaaaaacc aactcgctcc    3420
aacaatagtt tccactcttc gatccttttg caggcttttc agaattttt tttttttta    3480 atgcaccctc ctagcgtctc cccttctca taaagtaaaa taaatacgat taaaaacacc    3540
aaatgcattt cattaattga aggaatcaac agtcccaact tctaagcaga cgggctggtc    3600
ttccaaaggc tgggtcggtt tcaggagctt tctctccaaa taaatctctg cttcttcgac    3660
ttgcctatcg ctttaaaatc ttagaaacag agttagttgt tggtttcctt ctttttctt    3720 tttcttttt atttctttt tgcataaact tttagagaat caatctagaa atttgaacta    3780
cttattagca tttgcaactg ggggtggggg gagcagcctc ccccacccca cccccactc    3840 tgcgtttccg gactagttcc agaaaccgcg gtttaaaatt taacccttcg agggtagctg    3900
gtgagggctg gggtattgtt tttcccctt gctccctgcc acgatcaagt ccgaaataat    3960
taaaggaaac gtaaagtgc aaagggcgcg cctgaccctg ataaacagag gtcagatttc    4020
gtaaggggac gggtgagtgt gagtgtgtgt gtgtttgtgt gtgtgtgtgt aagagagaga    4080
gagagcgagc gcgcaatatg agtctcaaag gccaaactcc ggccagtcag gagccggaag    4140
gctgagcccg gctgacctga ctttgagctt ccccggagtt atctcgcata ggcgctcgct    4200
ctgtccaagg gcacgcgacg ccagcgggca gccgtctcc gtgaagaatg gcctctaaac    4260
aacttatttt acctcgttgt aaagagaggg ataaaatggg cttcccctct ccacggatgc    4320
ccagccttct gggcaggcgc atggccggc ggcgcccagc ccgcagcccc gatccggaca    4380
ccccactgca tccctccctt cccggtccct tccccgcacg ggcgcccgag agacggacaa    4440
agagttgggg ccaagtttga gcgccgggca cggccaggct cagggaagga aggtccccgg    4500
cagacacctg ggtaccagag ttggtgcgag gaggaaaagc tgggaggcga attcacaatc    4560 ctggggggtgg agggcaggca ggggagggga atcaggccaa tcccagccga gtgagccccc    4620
agcgagctgg ggctccggat gggaggcctg tctcgcgctc caaagaaaag caaaccgccc    4680
tcccaggtcc gcccggattg ccgaagcccc tctggaaaaa ctccttcccc tcttacacca    4740
aactttgcgc cgggcctcgt tccctcccgg gtaggcagcg gcgcaggaag ggttaagcca    4800
gcccgtccca gctgacagtc agctgattgg gccctgattg acagtccga aaagtttcct    4860 tgtttctata ctattatgct aatcgcggcc gctctcgccg cctcccattg gcccggagtg    4920
ccagtcaatt tctcatttgg acctgacgtc acgagtgcta taaaactcag caattgcttt    4980
aaactcttct tgctggatca gaggctttaa aatcttttt catcttctag ctgtagctcg    5040
ggctgcttgt cggcttggcc tccccctccc cccttgctc tctgcctcgt ctttccccag    5100
gacttcgcta ttttgctttt ttaaaaaaag gcaagaaaga actaaactcc cccctccctc    5160
tcctccagtc gggctgcacc tctgccttgc actttgcaca gaggtagaga gcgcgcgagg    5220
gagagagagg aaagaaaaaa aataataaag agagccaagc agaagaggag gcgagaagca    5280
tgaagtgtta actcccccgt gccaaggccc gcgccgcccg gacagacgcc cgccgcgcct    5340
ccagccccga gcggacgccg cgcgcgccct gcctgcagcc cgggccggcg aggcgagccc    5400
```

```
ttccttatgc aaagcgcgca gcggagcggc gagcggggga cgccgcgcac cgggccgggc    5460
tcctccagct tcgccgccgc agccaccacc gccgccaccg cagctcgcgg aggatcttcc    5520
cgagcctgaa gccgccggct cggcgcgcaa ggaggcgagc gagcaaggag gggccggggc    5580
gagcgaggga gcacattggc gtgagcaggg gggagggagg gcgggcgcgg ggggcgcggg    5640
cagggcgggg gggtgtgtgt gtgagcgcgc tcggaggttt cgggccagcc accgccgcgc    5700
aagctagaag cgcccagcc cggcaagctg gctcacccgc tggccaccca gcacagcccg    5760
ctggcccctc tcctgcagcc catctggcgg agcggcggcg gcggcggcgg cggcggcagg    5820
agaatggcat cagaactggc aatgagcaac tccgacctgc ccaccagtcc cctggccatg    5880
gaatatgtta atgacttcga tctgatgaag tttgaagtga aaaggaacc ggtggagacc      5940 gaccgcatca tcagccagtg cggccgtctc atcgccgggg gctcgctgtc ctccaccccc    6000
atgagcacgc cgtgcagctc ggtgccccct tcccccagct tctcggcgcc cagcccgggc    6060
tcgggcagcg agcagaaggc gcacctggaa gactactact ggatgaccgg ctacccgcag    6120
cagctgaacc ccgaggcgct gggcttcagc cccgaggacg cggtcgaggc gctcatcagc    6180
aacagccacc agctccaggg cggcttcgat ggctacgcgc gcggggcgca gcagctggcc    6240
gcggcggccg gggccggtgc cggcgcctcc ttgggcggca gcggcgagga gatgggcccc    6300
gccgccgccg tggtgtccgc cgtgatcgcc gcggccgccg cgcagagcgg cgcgggcccg    6360
cactaccacc accaccacca ccacgccgcc ggccaccacc accacccgac ggccggcgcg    6420 cccgcgccg cgggcagcgc ggccgcctcg gccggtggcg ctgggggcgc gggcggcggt    6480
ggcccggcca gcgctggggg cggcgcggc ggcggcggcg gcggaggcgg cggggcgcg      6540 gcgggggcgg ggggcgccct gcacccgcac cacgccgccg gcggcctgca cttcgacgac    6600
cgcttctccg acgagcagct ggtgaccatg tctgtgcgcg agctgaaccg gcagctgcgc    6660
ggggtcagca aggaggaggt gatccggctg aagcagaaga ggcggaccct gaaaaaccgc    6720
ggctatgccc agtcctgccg cttcaagagg gtgcagcaga gacacgtcct ggagtcggag    6780
aagaaccagc tgctgcagca gtcgaccac ctcaagcagg agatctccag gctggtgcgc    6840
gagagggacg cgtacaagga gaaatacgag aagttggtga gcagcggctt ccgagaaaac    6900
ggctcgagca gcgacaaccc gtcctctccc gagttttttca tgtgagtctg acacgcgatt    6960
ccagctagcc acccctgataa gtgctccgcg ggggtccggc tcgggtgtgg gcttgctagt    7020
tctagagcca tgctcgccac cacctccacca ccccaccccc caccgagttt ggcccccttg    7080
gccccctaca cacacacaaa cccgcacgca cacaccacac acacacacac acacacacac    7140 acacccaca ccctgctcga gtttgtggtg gtggtggctg ttttaaactg gggagggaat     7200
gggtgtctgg ctcatggatt gccaatctga aattctccat aacttgctag cttgtttttt    7260 ttttttttt acacccccc gcccacccc cggacttgca caatgttcaa tgatctcagc       7320
agagttcttc atgtgaaacg ttgatcacct ttgaagcctg catcattcac atatttttc     7380 ttcttcttcc ccttcagttc atgaactggt gttcattttc tgtgtgtgtg tgtgttttat    7440
tttgtttgga tttttttttt taattttact tttagagctt gctgtgttgc ccaccttttt    7500
tccaacctcc accctcactc cttctcaacc catctcttcc gagatgaaag aaaaaaaaa     7560 gcaaagtttt tttttcttct cctgagttct tcatgtgaga ttgagcttgc aaggaaaaa     7620 aaaatgtgaa atgttataga cttgcagcgt gccgagttcc atcgggtttt ttttttagca    7680
ttgttatgct aaaatagaga aaaaaatcct catgaacctt ccacaatcaa gcctgcatca    7740
```

-continued

```
accttctggg tgtgacttgt gagttttggc cttgtgatgc caaatctgag agtttagtct    7800
gccattaaaa aaactcattc tcatctcatg cattattatg cttgctactt tgtcttagca    7860
acaatgaact ataactgttt caaagacttt atggaaaaga gacattatat taataaaaaa    7920
aaaaagcctg catgctggac atgtatggta aattatttt ttcctttttt tttccttttg    7980
gcttggaaat ggacgttcga agacttatag catggcattc atacttttgt tttattgcct    8040
catgactttt ttgagtttag aacaaaacag tgcaaccgta gagccttctt cccatgaaat    8100
tttgcatctg ctccaaaact gctttgagtt actcagaact tcaacctccc aatgcactga    8160
aggcattcct tgtcaaagat accagaatgg gttacacatt taacctggca acattgaag    8220 aactcttaat gttttctttt taataagaat gacgccccac tttggggact aaaattgtgc    8280
tattgccgag aagcagtcta aaatttattt tttaaaaaga gaaactgccc cattattttt    8340
ggtttgtttt attttttattt tatatttttt ggcttttggt cattgtcaaa tgtggaatgc    8400
tctgggtttc tagtatataa tttaattcta gttttttataa tctgttagcc cagttaaaat    8460
gtatgctaca gataaaggaa tgttatagat aaatttgaaa gagttaggtc tgtttagctg    8520
tagatttttt aaacgattga tgcactaaat tgtttactat tgtgatgtta agggggtag    8580 agtttgcaag gggactgttt aaaaaaagta gcttatacag catgtgcttg caacttaaat    8640
ataagttggg tatgtgtagt ctttgctata ccactgactg tattgaaaac caaagtatta    8700 agagggaaa cgcccctgtt tatatctgta ggggtatttt acattcaaaa atgtatgttt    8760
tttttctttt tcaaaattaa agtatttggg actgaattgc actaagatat aacctgcaag    8820
catataatac aaaaaaaaat tgcaaaactg tttagaacgc taataaaatt tatgcagtta    8880
taaaaatggc attactgcac agttttaaga tgatgcagat ttttttacag ttgtattgtg    8940
gtgcagaact ggatttttctg taacttaaaa aaaaatccac agtttttaaag gcaataatca    9000 gtaaatgtta ttttcaggga ctgacatcct gtctttaaaa agaaatgaaa agtaaatctt    9060
accacaataa atataaaaaa atcttgtcag ttacttttct tttacatatt ttgctgtgca    9120
aaattgtttt atatcttgag ttactaacta accacgcgtg ttgttcctat gtgcttttct    9180 ttcatttttca attctggtta tatcaagaaa agaataatct acaataataa acggcatttt    9240
tttttgattc tgtactcagt ttcttagtgt acagtttaac tgggcccaac aacctcgtta    9300
aaagtgtaaa atgcatcctt ttctccagtg gaaggattcc tggaggaata gggagacagt    9360
aattcagggt gaaattatag gctgtttttt gaagtgagga ggctggcccc atatactgat    9420
tagcaatatt taatatagat gtaaattatg acctcatttt tttctcccca agttttcag    9480 ttttcaaatg agttgagcca taattgccct tggtaggaaa aacaaaacaa aacagtggaa    9540
ctaggcttcc tgagcatggc cctacacttc tgatcaggag caaagccatc catagacaga    9600
ggagccggac aaatatggcg catcagaggt ggcttgcgca catatgcatt gaacggtaaa    9660
gagaaacagc gcttgccttt tcactaaagt tgactatttt tccttcttct cttacacacc    9720 gagatttct tgttagcaag gcctgacaag atttaacata aacatgacaa atcatagttg    9780
tttgttttgt tttgcttttc tctttaacac tgaagatcat ttgtcttaaa taggaaaaag    9840
aaaatccact ccttacttcc atatttccaa gtacatatct ggtttaaact atgttatcaa    9900
atcatatttc accgtgaata ttcagtggag aacttctcta cctggatgag ctagtaatga    9960
tttcagatca tgctatcccc agaaataaaa gcaaaaaata ataccctgtgt ggaatatagg   10020 ctgtgctttg atttactggt atttacccca aaataggctg tgtatggggg ctgacttaaa   10080
gatcccttgg aaagactcaa aactaccttc actagtagga ctcctaagcg ctgacctatt   10140
```

```
tttaaatgac acaaattcat gaaactaatg ttacaaattc atgcagtttg cactcttagt   10200
catcttcccc tagcacacca atagaatgtt agacaaagcc agcactgttt tgaaaataca   10260
gccaaacacg atgactttg ttttgttttc tgccgttctt aaaagaaaaa aagataatat    10320
tgcaactctg actgaaagac ttattttaa gaaaacaggt tgtgtttggt gctgctaagt    10380
tctggccagt ttatcatctg gccttcctgc ctatttttta caaaacacga agacagtgtg   10440
taacctcgac attttgacct tcctttatgt gctagtttag acaggctcct gaatccacac   10500
ttaattttgc ttaacaaaag tcttaatagt aaacctcccc tcatgagctt gaagtcaagt   10560
gttcttgact tcagatattt cttcctttt ttttttttt tcctcatcac aactaagaga    10620
tacacaaact ctgaagaagc agaaatggag agaatgcttt taacaaaaaa gcatctgatg   10680
aaagatttta ggcaaacatt ctcaaaataa gagtgatatt ctggatgtag ttattgcagt   10740
tatctcatga caaatgaggc ctggattgga aggaaaatat agttgtgtag aattaagcat   10800
tttgatagga atctcaaagg tagttgaata taataagcag gtttgggccc ccaaacttta   10860
gaaaatcaaa tgcaaaggtg ctggcaaaaa tgaggtttga gtggctggct gtaagagaag   10920
gttaactcct agtaaaaggc atttttagaa ataacaatta ctgaaaactt tgaagtatag   10980
tgggagtagc aaacaaatac atgttttttt ttcttacaa agaactccta aatcctgagt     11040
aagtgccatt cattacaata agtctctaaa tttaaaaaa aaaaaatcat atgaggaaat     11100
ctagctttcc cctttacgct gcgtttgatc tttgtctaaa tagtgttaaa attcctttca   11160
ttccaattac agaactgagc ccactcgcaa gttggagcca tcagtgggat acgccacatt   11220
ttggaagccc cagcatcgtg tacttaccag tgtgttcaca aaatgaaatt tgtgtgagag   11280
ctgtacatta aaaaaaatca tcattattat tattatttgc agtcatggag aaccacctac   11340
ccctgacttc tgtttagtct cctttttaaa taaaaattac tgtgttagag aagaaggcta   11400
ttaaatgtag tagttaacta tgcctcttgt ctgggggttt catagagacc ggtaggaaag   11460
cgcactcctg cttttcgatt tatggtgtgt gcaagtaaac aggtgcattg ctttcaacct   11520
gccatactag ttttaaaaat tcactgaaat tacaaagata catatatg catatatata      11580
atggaaagtt tcccggaatg caacaattag cattttaaaa tcatatatag gcatgcacat   11640
tctaaatagt acttttttcat gcttcattgt ttctctggca gataaatttta ctaagaagaa   11700
aaatagatat tcgactcccc ttccctaaac aaatccacgg gcagaggctc cagcggagcc   11760
gagcccctg gttttctcgt aggccctaga cggtgttgca tttatcagtg atgtcaaacg     11820
tgctcatttg tcagacatag ctgtaaatga aacaatgtg tggcaaaata caagttagt       11880
taaatacaca ccctctgtgt gattttttgc tcccttttct ttttgctcc tactcaaaaa      11940
aaaaaaaatc acctccttta catttccctg gcttcttgca tgtttccctt ttcaaaaacc    12000
atgtaataat ttttacaat gtatctgaca cattaatata ttgacatcaa ataggcagac       12060
attctacttt tgcctggcaa ataaatctgc tacgagaca tcatttcctc actgtctcaa      12120
agccataact acctgggagt ctttcaacac agacccctcc gatgggaaat gctgtttatt    12180
actgaatgca ggatgctcac gctctgatct tttctcccctt gtgcctttac cccagtcatt    12240
tttacttagc aacaccaatt ctagatactt ctgttctgaa gtagaaccac ccccttgcca   12300
cactgccagt tttcctgcta aaagcagtgg acagaagaca gatcatggtc accctcacaa  12360
acatggcaca cagctgtctc ggtagctgca ttcccagcat gtcctggtct aaatatctag   12420
agttgcctat gacacgttca aaggttccca agcacagtac attgggaggc ttttgctgct  12480
```

```
gtggccgttg ttttcgttta ggccaactta cttccgtatt cacatactct tggctttacg   12540
aaatacactc ctccagtcta ctaggccaat caatatattt aaaagtctga ttgccacata   12600
agtctctctc tctctctttt tgttttttgt ttgtttgttt tttctgtttt tggctgccgg   12660
tagttaaaga ctgagatagg ttggaagact aaaatacagg agtacatgag tgacaacctt   12720
cagccgtctg atttccatgc cggtaaaaca cacaaccaag ctcttcttag cgctgctaat   12780
ataaacattc actaagaggg aataggaagt gagatttacc agcttcactt tgctgatttg   12840
caaggttccc cactacgatt cactgtcatt tgattttga aaaataattt tgtccgtctc   12900
tttgaagaaa tgtcttagtt cttttatttt gtttgtttgg tttttttag agaagtttta   12960 tctgcagtga taggctacaa tttttatctc cgctgattat ttgtcaggat gctgaatgaa   13020
taatttggtc ctgtgccttc cttgttgttc tgaggaaaat aagagaaact tggaagtttg   13080
tttcactctt agcccatcct aaatctaaaa gaagatgtcc caggtccagg caggccatgt   13140
agtagttata aaggaggtgg tccaggtcca gccacctcaa tcaggatttg tttgttttga   13200
agcatttgct taaaagcgga gcaagagtct taacccaact tgccataaca ctgcttttct   13260
cgcttttgat gtaaatcttc aaaattcaga catcaaacag ccccagaaaa ggggaattct   13320
ctccaggcat tgctccgccc cagctcctga acaaacccag ctctgtctag cattttttc   13380 cctagcgggg gtaggggaca gggtgagaga atttcagtct cccaggctgt ctcatgattg   13440
ttagggcata aagaaacaca gtcctgccac aaattgggag catctttacc ctttagagag   13500
aaacaaaaca aaactaaaca aacaaatcaa attgctttgc atgaaggcgt agcaaataaa   13560
atctcgggct ccctgttccc tgcaccattt gtaggaggtg agaaatgagg gaaacaagag   13620 aaagggggaac tttaaaagcg ggaggcccag aaataatccc tgttaccagt ctgaatttca   13680
cttgctccgt ggctaacgtc agacctagtg tgcatgtatg ccagaagtaa actaggctcg   13740
gctgtccatt tctttaaaat atgttcacat gtttcctttt tgaaaacaat tttggggact   13800
aaacccaaat ggagagattt gaggaaatcg ttaatgtctt aacatttgag tatatttata   13860
aatgtatcag tctgtgat                                                 13878

<210> SEQ ID NO 14
<211> LENGTH: 1368
<212> TYPE: DNA
<213> ORGANISM: Artificial Sequence
<220> FEATURE:
<223> OTHER INFORMATION: INB-1-11-8 (H1) Heavy Chain
<220> FEATURE:
<221> NAME/KEY: misc_feature
<222> LOCATION: (1)..(396)
<223> OTHER INFORMATION: Variable Heavy Chain
<220> FEATURE:
<221> NAME/KEY: misc_feature
<222> LOCATION: (397)..(402)
<223> OTHER INFORMATION: Start of constant region
<220> FEATURE:
<221> NAME/KEY: misc_feature
<222> LOCATION: (949)..(1248)
<223> OTHER INFORMATION: Variant

<400> SEQUENCE: 14
atggagactg gctgcgctg gcttctcctg gtcgctgtgc tcaaaggtgt ccagtgtcag     60
tcgctggagg agtccggggg tcgcctggtc acgcctggga caccctgac actcacctgc    120 acagcctctg gattctccct caataactat ccaatgacct gggtccgcca ggctccaggg    180
aaggggctgg attatatcgg agtcattaat aatagtggtg aaacagccta cgcgacctgg    240
gcgaagcgcc gattcaccat ctccagaacc tcgaccacgt tgtatctgaa aatcgccagt    300
```

-continued

| | |
|---|---|
| ccgacaatcg aggacacggc cacctatttc tgtgccagag ggggtcctgt tagtagtgat | 360 |
| atgtggggcc caggcaccct ggtcatcgtc tcctcagggc aacctaaggc tccatcagtc | 420 |
| ttcccactgg cccctgctg cggggacaca cccagctcca cggtgaccct gggctgcctg | 480 |
| gtcaaagggt acctcccgga gccagtgacc gtgacctgga actcgggcac cctcaccaat | 540 |
| ggggtacgca ccttcccgtc cgtccggcag tcctcaggcc tctactcgct gagcagcgtg | 600 |
| gtgagcgtga cctcaagcag ccagcccgtc acctgcaacg tggcccaccc agccaccaac | 660 |
| accaaagtgg acaagaccgt tgcgccctcg acatgcagca agcccacgtg cccacccct | 720 |
| gaactcctgg ggggaccgtc tgtcttcatc ttcccccaa aacccaagga caccctcatg | 780 |
| atctcacgca cccccgaggt cacatgcgtg gtggtggacg tgagccagga tgaccccgag | 840 |
| gtgcagttca catggtacat aaacaacgag caggtgcgca ccgccggcc gccgctacgg | 900 |
| gagcagcagt tcaacagcac gatccgcgtg gtcagcaccc tccccatcgc gcaccaggac | 960 |
| tggctgaggg gcaaggagtt caagtgcaaa gtccacaaca aggcactccc ggcccccatc | 1020 |
| gagaaaacca tctccaaagc cagagggcag cccctggagc cgaaggtcta caccatgggc | 1080 |
| cctcccgggg aggagctgag cagcaggtcg gtcagcctga cctgcatgat caacggcttc | 1140 |
| taccttccg acatctcggt ggagtgggag aagaacggga aggcagagga caactacaag | 1200 |
| accacgccgg ccgtgctgga cagcgacggc tcctacttcc tctacagcaa gctctcagtg | 1260 |
| cccacgagtg agtggcagcg gggcgacgtc ttcacctgct ccgtgatgca cgaggccttg | 1320 |
| cacaaccact acacgcagaa gtccatctcc cgctctccgg gtaaatga | 1368 |

<210> SEQ ID NO 15
<211> LENGTH: 396
<212> TYPE: DNA
<213> ORGANISM: Artificial Sequence
<220> FEATURE:
<223> OTHER INFORMATION: INB-1-11-8 (H1) Variable Heavy Chain

<400> SEQUENCE: 15

| | |
|---|---|
| atggagactg ggctgcgctg gcttctcctg gtcgctgtgc tcaaaggtgt ccagtgtcag | 60 |
| tcgctggagg agtccggggg tcgcctggtc acgcctggga cacccctgac actcacctgc | 120 |
| acagcctctg gattctccct caataactat ccaatgacct gggtccgcca ggctccaggg | 180 |
| aaggggctgg attatatcgg agtcattaat aatagtggtg aaacagccta cgcgacctgg | 240 |
| gcgaagcgcc gattcaccat ctccagaacc tcgaccacgt tgtatctgaa aatcgccagt | 300 |
| ccgacaatcg aggacacggc cacctatttc tgtgccagag ggggtcctgt tagtagtgat | 360 |
| atgtggggcc caggcaccct ggtcatcgtc tcctca | 396 |

<210> SEQ ID NO 16
<211> LENGTH: 455
<212> TYPE: PRT
<213> ORGANISM: Artificial Sequence
<220> FEATURE:
<223> OTHER INFORMATION: INB-1-11-8 (H1) Heavy Chain
<220> FEATURE:
<221> NAME/KEY: MISC_FEATURE
<222> LOCATION: (1)..(132)
<223> OTHER INFORMATION: Variable Heavy Chain
<220> FEATURE:
<221> NAME/KEY: MISC_FEATURE
<222> LOCATION: (133)..(138)
<223> OTHER INFORMATION: Start of constant region
<220> FEATURE:
<221> NAME/KEY: MISC_FEATURE
<222> LOCATION: (317)..(416)

<223> OTHER INFORMATION: Variant

<400> SEQUENCE: 16

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Pro Met Thr Trp Val Arg Gln Ala Pro Gly Lys Gly Leu Asp
50                  55                  60

Tyr Ile Gly Val Ile Asn Asn Ser Gly Glu Thr Ala Tyr Ala Thr Trp
65                  70                  75                  80

Ala Lys Arg Arg Phe Thr Ile Ser Arg Thr Ser Thr Thr Leu Tyr Leu
                85                  90                  95

Lys Ile Ala Ser Pro Thr Ile Glu Asp Thr Ala Thr Tyr Phe Cys Ala
            100                 105                 110

Arg Gly Gly Pro Val Ser Ser Asp Met Trp Gly Pro Gly Thr Leu Val
        115                 120                 125

Ile Val Ser Ser Gly Gln Pro Lys Ala Pro Ser Val Phe Pro Leu Ala
130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
290                 295                 300

Asn Ser Thr Ile Arg Val Val Ser Thr Leu Pro Ile Ala His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400
```

Thr Thr Pro Ala Val Leu Asp Ser Asp Gly Ser Tyr Phe Leu Tyr Ser
            405                 410                 415

Lys Leu Ser Val Pro Thr Ser Glu Trp Gln Arg Gly Asp Val Phe Thr
        420                 425                 430

Cys Ser Val Met His Glu Ala Leu His Asn His Tyr Thr Gln Lys Ser
        435                 440                 445

Ile Ser Arg Ser Pro Gly Lys
    450                 455

<210> SEQ ID NO 17
<211> LENGTH: 132
<212> TYPE: PRT
<213> ORGANISM: Artificial Sequence
<220> FEATURE:
<223> OTHER INFORMATION: INB-1-11-8 (H1) Variable Heavy Chain

<400> SEQUENCE: 17

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Asn
        35                  40                  45

Asn Tyr Pro Met Thr Trp Val Arg Gln Ala Pro Gly Lys Gly Leu Asp
    50                  55                  60

Tyr Ile Gly Val Ile Asn Asn Ser Gly Glu Thr Ala Tyr Ala Thr Trp
65                  70                  75                  80

Ala Lys Arg Arg Phe Thr Ile Ser Arg Thr Ser Thr Thr Leu Tyr Leu
                85                  90                  95

Lys Ile Ala Ser Pro Thr Ile Glu Asp Thr Ala Thr Tyr Phe Cys Ala
            100                 105                 110

Arg Gly Gly Pro Val Ser Ser Asp Met Trp Gly Pro Gly Thr Leu Val
        115                 120                 125

Ile Val Ser Ser
    130

<210> SEQ ID NO 18
<211> LENGTH: 711
<212> TYPE: DNA
<213> ORGANISM: Artificial Sequence
<220> FEATURE:
<223> OTHER INFORMATION: INB-1-11-8 (L) Light chain
<220> FEATURE:
<221> NAME/KEY: misc_feature
<222> LOCATION: (1)..(399)
<223> OTHER INFORMATION: Variable Light Chain
<220> FEATURE:
<221> NAME/KEY: misc_feature
<222> LOCATION: (400)..(401)
<223> OTHER INFORMATION: Start of constant region
<220> FEATURE:
<221> NAME/KEY: misc_feature
<222> LOCATION: (436)..(447)
<223> OTHER INFORMATION: Variant

<400> SEQUENCE: 18
atggacacga gggcccccac tcagctgctg gggctcctgc tgctctggct cccaggtgcc      60
acatttgccc aagtgctgac ccagactgca tcccctgtgt ctgcagttgt gggaggcaca     120
gtcaccatca attgccagtc cagtcagagt gtttatcgtg cgactggtt agcctggtat     180 cagcagagac cagggcagcc tcccaagctc ctgatctatg gtgcatccac tttggcatct     240

```
ggggtcccat cgcggttcaa aggcagtgga tctgggacac acttcactct caccatcagc    300
gacctggact gtgacgatgc tgccacttac tattgtgcag gcggttttag tggccatatt    360
tatgatttcg gcggagggac cgaggtggtg gtcaaaggtg atccagttgc acctactgtc    420
ctcatcttcc caccagctgc tgatcaggtg gcaactggaa cagtcaccat cgtgtgtgtg    480
gcgaataaat actttcccga tgtcaccgtc acctgggagg tggatggcac cacccaaaca    540
actggcatcg agaacagtaa aaccccgcag aattctgcag attgtaccta caacctcagc    600
agcactctga cactgaccag cacacagtac aacagccaca agagtacac ctgcaaggtg    660 acccagggca cgacctcagt cgtccagagc ttcaataggg gtgactgtta g            711

<210> SEQ ID NO 19
<211> LENGTH: 399
<212> TYPE: DNA
<213> ORGANISM: Artificial Sequence
<220> FEATURE:
<223> OTHER INFORMATION: INB-1-11-8 (L4) Variable Light chain

<400> SEQUENCE: 19
atggacacga gggcccccac tcagctgctg gggctcctgc tgctctggct cccaggtgcc    60
acatttgccc aagtgctgac ccagactgca tcccctgtgt ctgcagttgt gggaggcaca   120
gtcaccatca attgccagtc cagtcagagt gtttatcgtg gcgactggtt agcctggtat   180
cagcagagac cagggcagcc tcccaagctc ctgatctatg gtgcatccac tttggcatct   240
ggggtcccat cgcggttcaa aggcagtgga tctgggacac acttcactct caccatcagc   300
gacctggact gtgacgatgc tgccacttac tattgtgcag gcggttttag tggccatatt   360
tatgatttcg gcggagggac cgaggtggtg gtcaaaggt                          399

<210> SEQ ID NO 20
<211> LENGTH: 236
<212> TYPE: PRT
<213> ORGANISM: Artificial Sequence
<220> FEATURE:
<223> OTHER INFORMATION: INB-1-11-8 (L4) Light chain
<220> FEATURE:
<221> NAME/KEY: MISC_FEATURE
<222> LOCATION: (1)..(133)
<223> OTHER INFORMATION: Variable Light Chain
<220> FEATURE:
<221> NAME/KEY: MISC_FEATURE
<222> LOCATION: (134)..(139)
<223> OTHER INFORMATION: Start of constant region
<220> FEATURE:
<221> NAME/KEY: MISC_FEATURE
<222> LOCATION: (146)..(149)
<223> OTHER INFORMATION: Variant

<400> SEQUENCE: 20

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Val Val Gly Gly Thr Val Thr Ile Asn Cys Gln Ser Ser
        35                  40                  45

Gln Ser Val Tyr Arg Gly Asp Trp Leu Ala Trp Tyr Gln Gln Arg Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr His Phe Thr
                85                  90                  95
```

```
Leu Thr Ile Ser Asp Leu Asp Cys Asp Asp Ala Ala Thr Tyr Tyr Cys
            100                 105                 110

Ala Gly Gly Phe Ser Gly His Ile Tyr Asp Phe Gly Gly Thr Glu
            115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
            210                 215                 220

Thr Ser Val Val Gln Ser Phe Asn Arg Gly Asp Cys
225                 230                 235

<210> SEQ ID NO 21
<211> LENGTH: 133
<212> TYPE: PRT
<213> ORGANISM: Artificial Sequence
<220> FEATURE:
<223> OTHER INFORMATION: INB-1-11-8 (L4) Variable Light chain

<400> SEQUENCE: 21

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Val Val Gly Gly Thr Val Thr Ile Asn Cys Gln Ser Ser
            35                  40                  45

Gln Ser Val Tyr Arg Gly Asp Trp Leu Ala Trp Tyr Gln Gln Arg Pro
        50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr His Phe Thr
                85                  90                  95

Leu Thr Ile Ser Asp Leu Asp Cys Asp Asp Ala Ala Thr Tyr Tyr Cys
            100                 105                 110

Ala Gly Gly Phe Ser Gly His Ile Tyr Asp Phe Gly Gly Thr Glu
            115                 120                 125

Val Val Val Lys Gly
        130

<210> SEQ ID NO 22
<211> LENGTH: 18
<212> TYPE: PRT
<213> ORGANISM: Homo sapiens

<400> SEQUENCE: 22

Glu Gln Lys Ala His Leu Glu Asp Tyr Tyr Trp Met Thr Gly Tyr Pro
1               5                   10                  15

Gln Gln
```

```
<210> SEQ ID NO 23
<211> LENGTH: 95
<212> TYPE: PRT
<213> ORGANISM: Artificial Sequence
<220> FEATURE:
<223> OTHER INFORMATION: VKI_2-1-(U)_L12

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 24
<211> LENGTH: 22
<212> TYPE: PRT
<213> ORGANISM: Artificial Sequence
<220> FEATURE:
<223> OTHER INFORMATION: Leader

<400> SEQUENCE: 24

Met Asp Thr Arg Ala Pro Thr Gln Leu Leu Gly Leu Leu Leu Leu Trp
1               5                   10                  15

Leu Pro Gly Ala Thr Phe
            20

<210> SEQ ID NO 25
<211> LENGTH: 23
<212> TYPE: PRT
<213> ORGANISM: Artificial Sequence
<220> FEATURE:
<223> OTHER INFORMATION: Framework 1

<400> SEQUENCE: 25

Ala Gln Val Leu Thr Gln Thr Ala Ser Pro Val Ser Ala Val Val Gly
1               5                   10                  15

Gly Thr Val Thr Ile Asn Cys
            20

<210> SEQ ID NO 26
<211> LENGTH: 13
<212> TYPE: PRT
<213> ORGANISM: Artificial Sequence
<220> FEATURE:
<223> OTHER INFORMATION: CDR1

<400> SEQUENCE: 26

Gln Ser Ser Gln Ser Val Tyr Arg Gly Asp Trp Leu Ala
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Framework 2
```

<400> SEQUENCE: 27

Trp Tyr Gln Gln Arg Pro Gly Gln Pro Pro Lys Leu Leu Ile Tyr
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: CDR2

<400> SEQUENCE: 28

Gly Ala Ser Thr Leu Ala Ser
1               5

<210> SEQ ID NO 29
<211> LENGTH: 32
<212> TYPE: PRT
<213> ORGANISM: Artificial Sequence
<220> FEATURE:
<223> OTHER INFORMATION: Framework 3

<400> SEQUENCE: 29

Gly Val Pro Ser Arg Phe Lys Gly Ser Gly Ser Gly Thr His Phe Thr
1               5                   10                  15

Leu Thr Ile Ser Asp Leu Asp Cys Asp Asp Ala Ala Thr Tyr Tyr Cys
            20                  25                  30

<210> SEQ ID NO 30
<211> LENGTH: 10
<212> TYPE: PRT
<213> ORGANISM: Artificial Sequence
<220> FEATURE:
<223> OTHER INFORMATION: CDR3

<400> SEQUENCE: 30

Ala Gly Gly Phe Ser Gly His Ile Tyr Asp
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Junction

<400> SEQUENCE: 31

Phe Gly Gly Gly Thr Glu Val Val Val Lys
1               5                   10

<210> SEQ ID NO 32
<211> LENGTH: 104
<212> TYPE: PRT
<213> ORGANISM: Artificial Sequence
<220> FEATURE:
<223> OTHER INFORMATION: LC Portion

<400> SEQUENCE: 32

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
            35                  40                  45

Thr Gly Ile Glu Asn Ser Lys Thr Pro Gln Asn Ser Ala Asp Cys Thr
 50                  55                  60

Tyr Asn Leu Ser Ser Thr Leu Thr Leu Thr Ser Thr Gln Tyr Asn Ser
 65                  70                  75                  80

His Lys Glu Tyr Thr Cys Lys Val Thr Gln Gly Thr Thr Ser Val Val
                 85                  90                  95

Gln Ser Phe Asn Arg Gly Asp Cys
            100

<210> SEQ ID NO 33
<211> LENGTH: 98
<212> TYPE: PRT
<213> ORGANISM: Artificial Sequence
<220> FEATURE:
<223> OTHER INFORMATION: VH3_1-3_3-64

<400> SEQUENCE: 33

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Tyr Val
             35                  40                  45

Ser Ala Ile Ser Ser Asn Gly Gly Ser Thr Tyr Tyr Ala Asn Ser Val
         50                  55                  60

Lys Gly Arg Phe Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
                 85                  90                  95

Ala Arg

<210> SEQ ID NO 34
<211> LENGTH: 97
<212> TYPE: PRT
<213> ORGANISM: Artificial Sequence
<220> FEATURE:
<223> OTHER INFORMATION: VH3_1-1_3-66

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 35
<211> LENGTH: 97
<212> TYPE: PRT
<213> ORGANISM: Artificial Sequence
<220> FEATURE:

<223> OTHER INFORMATION: VH3_1-1_3-53

<400> SEQUENCE: 35

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 36
<211> LENGTH: 19
<212> TYPE: PRT
<213> ORGANISM: Artificial Sequence
<220> FEATURE:
<223> OTHER INFORMATION: Leader

<400> SEQUENCE: 36

Met Glu Thr Gly Leu Arg Trp Leu Leu Leu Val Ala Val Leu Lys Gly
1               5                   10                  15

Val Gln Cys

<210> SEQ ID NO 37
<211> LENGTH: 29
<212> TYPE: PRT
<213> ORGANISM: Artificial Sequence
<220> FEATURE:
<223> OTHER INFORMATION: Framework 1

<400> SEQUENCE: 37

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Asn
            20                  25

<210> SEQ ID NO 38
<211> LENGTH: 5
<212> TYPE: PRT
<213> ORGANISM: Artificial Sequence
<220> FEATURE:
<223> OTHER INFORMATION: CDR1

<400> SEQUENCE: 38

Asn Tyr Pro Met Thr
1               5

<210> SEQ ID NO 39
<211> LENGTH: 14
<212> TYPE: PRT
<213> ORGANISM: Artificial Sequence
<220> FEATURE:
<223> OTHER INFORMATION: Framework 2

<400> SEQUENCE: 39

Trp Val Arg Gln Ala Pro Gly Lys Gly Leu Asp Tyr Ile Gly

```
<210> SEQ ID NO 40
<211> LENGTH: 16
<212> TYPE: PRT
<213> ORGANISM: Artificial Sequence
<220> FEATURE:
<223> OTHER INFORMATION: CDR2

<400> SEQUENCE: 40

Val Ile Asn Asn Ser Gly Glu Thr Ala Tyr Ala Thr Trp Ala Lys Arg
1               5                   10                  15

<210> SEQ ID NO 41
<211> LENGTH: 30
<212> TYPE: PRT
<213> ORGANISM: Artificial Sequence
<220> FEATURE:
<223> OTHER INFORMATION: Framework 3

<400> SEQUENCE: 41

Arg Phe Thr Ile Ser Arg Thr Ser Thr Thr Leu Tyr Leu Lys Ile Ala
1               5                   10                  15

Ser Pro Thr Ile Glu Asp Thr Ala Thr Tyr Phe Cys Ala Arg
            20                  25                  30

<210> SEQ ID NO 42
<211> LENGTH: 8
<212> TYPE: PRT
<213> ORGANISM: Artificial Sequence
<220> FEATURE:
<223> OTHER INFORMATION: CDR3

<400> SEQUENCE: 42

Gly Gly Pro Val Ser Ser Asp Met
1               5

<210> SEQ ID NO 43
<211> LENGTH: 11
<212> TYPE: PRT
<213> ORGANISM: Artificial Sequence
<220> FEATURE:
<223> OTHER INFORMATION: Junction

<400> SEQUENCE: 43

Trp Gly Pro Gly Thr Leu Val Ile Val Ser Ser
1               5                   10

<210> SEQ ID NO 44
<211> LENGTH: 323
<212> TYPE: PRT
<213> ORGANISM: Artificial Sequence
<220> FEATURE:
<223> OTHER INFORMATION: HC portion

<400> SEQUENCE: 44

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60
```

```
Leu Ser Ser Val Val Ser Val Thr Ser Ser Ser Gln Pro Val Thr Cys
 65                  70                  75                  80

Asn Val Ala His Pro Ala Thr Asn Thr Lys Val Asp Lys Thr Val Ala
                 85                  90                  95

Pro Ser Thr Cys Ser Lys Pro Thr Cys Pro Pro Glu Leu Leu Gly
            100                 105                 110

Gly Pro Ser Val Phe Ile Phe Pro Pro Lys Pro Lys Asp Thr Leu Met
            115                 120                 125

Ile Ser Arg Thr Pro Glu Val Thr Cys Val Val Val Asp Val Ser Gln
        130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Ser Lys Leu Ser Val
        275                 280                 285

Pro Thr Ser Glu Trp Gln Arg Gly Asp Val Phe Thr Cys Ser Val Met
290                 295                 300

His Glu Ala Leu His Asn His Tyr Thr Gln Lys Ser Ile Ser Arg Ser
305                 310                 315                 320

Pro Gly Lys

<210> SEQ ID NO 45
<211> LENGTH: 190
<212> TYPE: PRT
<213> ORGANISM: Artificial Sequence
<220> FEATURE:
<223> OTHER INFORMATION: Fragment of cMAF used including Aa 19-208

<400> SEQUENCE: 45

Met Glu Tyr Val Asn Asp Phe Asp Leu Met Lys Phe Glu Val Lys Lys
1               5                   10                  15

Glu Pro Val Glu Thr Asp Arg Ile Ile Ser Gln Cys Gly Arg Leu Ile
            20                  25                  30

Ala Gly Gly Ser Leu Ser Ser Thr Pro Met Ser Thr Pro Cys Ser Ser
        35                  40                  45

Val Pro Pro Ser Pro Ser Phe Ser Ala Pro Ser Pro Gly Ser Gly Ser
    50                  55                  60

Glu Gln Lys Ala His Leu Glu Asp Tyr Tyr Trp Met Thr Gly Tyr Pro
65                  70                  75                  80

Gln Gln Leu Asn Pro Glu Ala Leu Gly Phe Ser Pro Glu Asp Ala Val
                85                  90                  95

Glu Ala Leu Ile Ser Asn Ser His Gln Leu Gln Gly Gly Phe Asp Gly
```

```
                100                 105                 110
Tyr Ala Arg Gly Ala Gln Gln Leu Ala Ala Ala Gly Ala Gly Ala
            115                 120                 125
Gly Ala Ser Leu Gly Gly Ser Gly Glu Glu Met Gly Pro Ala Ala Ala
        130                 135                 140
Val Val Ser Ala Val Ile Ala Ala Ala Ala Gln Ser Gly Ala Gly
145                 150                 155                 160
Pro His Tyr His His His His His His Ala Ala Gly His His His
                165                 170                 175
Pro Thr Ala Gly Ala Pro Gly Ala Ala Gly Ser Ala Ala Ala
            180                 185                 190

<210> SEQ ID NO 46
<211> LENGTH: 95
<212> TYPE: PRT
<213> ORGANISM: Artificial Sequence
<220> FEATURE:
<223> OTHER INFORMATION: VKI_2-1-(1)_L19

<400> SEQUENCE: 46

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro
                85                  90                  95

<210> SEQ ID NO 47
<211> LENGTH: 95
<212> TYPE: PRT
<213> ORGANISM: Artificial Sequence
<220> FEATURE:
<223> OTHER INFORMATION: VKI_2-1-(1)_L5

<400> SEQUENCE: 47

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro
                85                  90                  95
```

BINDING MEMBERS FOR HUMAN C-MAF

REFERENCE TO SEQUENCE LISTING

The content of the electronically submitted sequence listing (Name 3190_0120001_SeqListing.txt; Size: 77,505 bytes; and Date of Creation: Jun. 5, 2017) is incorporated herein by reference in its entirety.

FIELD OF THE INVENTION

This invention relates to binding members, especially antibody molecules, which bind to human c-MAF. The binding members are useful for the quantitation of c-MAF, for the diagnosis and prognosis of c-MAF-related disorders, and for the treatment of c-MAF-related disorders.

BACKGROUND

Problem

Metastasis, a complex process caused by elaborate interactions between tumor cells and the surrounding normal tissues in different vital organs, accounts for 90 percent of all cancer deaths in patients with solid tumors. The molecular and cellular mechanisms that lead primary tumors to form metastases must be understood in order to better address this major life-threatening problem. The identification of metastasis genes and mechanisms is essential for understanding the basic biology of this lethal condition and its implications for clinical practice. Previous work provided a sense of the complexity of the metastasis process, but it failed to explain how and why metastasis occurs, what mechanisms make metastasis a tissue-specific process, what events allow dormant metastases to become active and lethal many years after removal of a primary tumor, and what metastasis-mediating genes would eventually constitute worthy diagnostic markers and therapeutic targets.

The present invention is based on the realization that the reliable identification of markers that predict bone metastasis would provide a preventive therapeutic opportunity by imposing restrictions to the spreading and colonization of bone metastatic tissue by cancer cells and delay or transform a lethal condition, and the necessity for a mechanism of identifying the expression of the metastasis predicting marker. Thus, for example, it has been shown that protein and mRNA accumulation of MAF, a bona fide breast cancer bone metastasis gene, can be acquired by 16q22-24 (16q23) amplifications or 16q23 translocations among other potential mechanisms. c-MAF is also responsible for driving the cancer bone metastatic lesions, including osteolytic cancer bone metastasis.

SUMMARY OF INVENTION

In one embodiment, the present invention relates to the detection of genetic abnormalities through the use of an antibody and to the prognosis and/or diagnosis of metastasis (e.g., bone metastasis) in cancer based on same. In one embodiment, the invention involves the use of an antibody to determine the levels of a gene of interest in a primary tumor sample. In one embodiment, the invention relates to a binding member (e.g., an antibody) that specifically binds to human c-MAF. Likewise, the invention also relates to a method for designing a customized therapy in a subject with cancer which comprises determining the level of a gene of interest in a sample using an antibody. In one embodiment, the gene of interest is MAF. In another embodiment, the cancer is breast cancer, lung cancer, prostate cancer, or renal cancer.

In one aspect, the present invention is directed to a binding member or functional fragment or variant thereof that specifically binds to the epitope encoded by SEQ ID NO: 22. In some embodiments, the binding member or functional fragment or variant thereof specifically binds to human c-MAF, wherein the binding member or functional fragment or variant thereof comprises a heavy chain CDR1 comprising the amino acid sequence of SEQ ID NO: 38, and/or a heavy chain CDR2 comprising the amino acid sequence of SEQ ID NO: 40, and/or a heavy chain CDR3 comprising the amino acid sequence of SEQ ID NO: 42; and/or a light chain CDR1 comprising the amino acid sequence of SEQ ID NO: 26, and/or a light chain CDR2 comprising the amino acid sequence of SEQ ID NO: 28 and/or a light chain CDR3 comprising the amino acid sequence of SEQ ID NO: 30.

In some embodiments, said binding member is an antibody. In some embodiments, the antibody is a rabbit antibody, a chimeric antibody or a humanized antibody.

In some embodiments, said binding member or functional fragment or variant thereof comprises a VH domain with a sequence that is at least 80% identical to the amino acid sequence of SEQ ID NO: 17. In some embodiments, the binding member or functional fragment or variant thereof comprises a VH domain with a sequence that is at least 90% identical to the amino acid sequence of SEQ ID NO: 17. In some embodiments, the binding member or functional fragment or variant thereof comprises a VH domain with a sequence that is at least 95% identical to the amino acid sequence of SEQ ID NO: 17. In some embodiments, the binding member of functional fragment or variant thereof comprises a VH domain with a sequence comprising the amino acid sequence of SEQ ID NO: 17.

In some embodiments, the binding member of functional fragment or variant thereof comprises a VL domain with a sequence that is at least 80% identical to the amino acid sequence of SEQ ID NO: 21. In some embodiments, the binding member of functional fragment or variant thereof comprises a VL domain with a sequence that is at least 90% identical to the amino acid sequence of SEQ ID NO: 21. In some embodiments, the binding member or functional fragment or variant thereof comprises a VL domain with a sequence that is at least 95% identical to the amino acid sequence of SEQ ID NO: 21. In some embodiments, the binding member or functional fragment or variant thereof comprises a VL domain with a sequence comprising the amino acid sequence of SEQ ID NO: 21.

In some embodiments, the binding member or functional fragment or variant thereof comprises a heavy chain sequence that is at least 80% identical to the amino acid sequence of SEQ ID NO: 16. In some embodiments, the binding member or functional fragment or variant thereof comprises a heavy chain sequence that is at least 90% identical to the amino acid sequence of SEQ ID NO: 16. In some embodiments, the binding member or functional fragment or variant thereof comprises a heavy chain sequence that is at least 95% identical to the amino acid sequence of SEQ ID NO: 16. In some embodiments, the binding member or functional fragment or variant thereof comprises a heavy chain sequence comprising the amino acid sequence of SEQ ID NO: 16.

In some embodiments, the binding member or functional fragment or variant thereof comprises a light chain sequence that is at least 80% identical to the amino acid sequence of SEQ ID NO: 20. In some embodiments, the binding member or functional fragment or variant thereof comprises a light chain sequence that is at least 90% identical to the amino acid sequence of SEQ ID NO: 20.

The binding member or functional fragment or variant thereof of claim 18, wherein the binding member or functional fragment or variant thereof comprises a light chain sequence that is at least 95% identical to the amino acid sequence of SEQ ID NO: 20. In some embodiments, the antibody or fragment thereof comprises a light chain sequence comprising the amino acid sequence of SEQ ID NO: 20.

In some embodiments, the present invention is directed to a polynucleotide encoding any binding member or functional fragment or variant thereof described herein. In some embodiments, the polynucleotide encode as a polypeptide that encodes an antigen binding molecule or fragment thereof. In some embodiments, the binding member or functional fragment or variant thereof is an antibody.

In some embodiments, the polynucleotide comprises a VH domain with a sequence that is at least 80% identical to the nucleotide sequence of SEQ ID NO: 15. In some embodiments, the polynucleotide encodes a VH domain with a sequence that is at least 90% identical to the nucleotide sequence of SEQ ID NO: 15. In some embodiments, the polynucleotide encodes a VH domain with a sequence that is at least 95% identical to the nucleotide sequence of SEQ ID NO: 15. In some embodiments, the polynucleotide encodes a VH domain with a sequence that is identical to the nucleotide sequence of SEQ ID NO: 15.

In some embodiments, the polynucleotide encodes a VL domain with a sequence that is at least 80% identical to the nucleotide sequence of SEQ ID NO: 20. In some embodiments, polynucleotide encodes a VL domain with a sequence that is at least 90% identical to the nucleotide sequence of SEQ ID NO: 20. In some embodiments, the polynucleotide encodes a VL domain with a sequence that is at least 95% identical to the nucleotide sequence of SEQ ID NO: 20. In some embodiments, polynucleotide encodes a VL domain with a sequence that is identical to the nucleotide sequence of SEQ ID NO: 20.

In some embodiments, the polynucleotide encodes a heavy chain with a sequence that is at least 80% identical to the nucleotide sequence of SEQ ID NO: 14. In some embodiments, the polynucleotide encodes a heavy chain with a sequence that is at least 90% identical to the nucleotide sequence of SEQ ID NO: 14. In some embodiments, the polynucleotide encodes a heavy chain with a sequence that is at least 95% identical to the nucleotide sequence of SEQ ID NO: 14. In some embodiments, the polynucleotide encodes a heavy chain with a sequence that is identical to the nucleotide sequence of SEQ ID NO: 14.

In some embodiments, the polynucleotide encodes a light chain with a sequence that is at least 80% identical to the nucleotide sequence of SEQ ID NO: 18. In some embodiments, the polynucleotide encodes a light chain with a sequence that is at least 90% identical to the nucleotide sequence of SEQ ID NO: 18. In some embodiments, the polynucleotide encodes a light chain with a sequence that is at least 95% identical to the nucleotide sequence of SEQ ID NO: 18. In some embodiments, the polynucleotide encodes a light chain with a sequence that is identical to the nucleotide sequence of SEQ ID NO: 18.

In some embodiments, the amino acid encoded for by the polynucleotide binds to the epitope described by SEQ ID NO: 22.

In some embodiments, the binding member or functional fragment or variant thereof binds to human c-MAF with an affinity (KD) of at least about 1.5 nM or less. In some embodiments, the binding member or variant thereof binds to human c-MAF with an affinity (KD) of at least about 1.2 nM or less. In some embodiments, the binding member or variant thereof binds to human c-MAF with an affinity (KD) of at least about 1.1 nM or less.

In some embodiments, the present invention is directed to a vector comprising any polynucleotide disclosed herein.

In some embodiments, the present invention is directed to a host cell comprising any polynucleotide disclosed herein or any vector disclosed herein, or expressing the any binding member disclosed herein. In some embodiments, the present invention is directed to a method of producing an antigen binding member comprising culturing the host cell. In some embodiments, the present invention is directed to a method of using an antigen binding member produced by the host cell or the method or production to detect c-MAF.

In some embodiments, the present invention is directed to a binding member or functional fragment or variant thereof that competes for binding with INB-1-11-8 to the epitope encoded by SEQ ID NO: 22.

BRIEF DESCRIPTION OF THE FIGURES

FIG. 2 illustrates a comparison of c-MAF amino sequences from *H. sapiens, P. troglodytes, B. Taurus, M musculus, R norvegicus, G. gallus,* and *D. rerio*.

FIG. 8 illustrates the sequences of the heavy and light chains of the c-MAF antibody INB-1-11-8.

FIG. 10. Baseline characteristics bivariate analysis.

DETAILED DESCRIPTION OF THE INVENTION

Definitions of General Terms and Expressions

Figure 1:
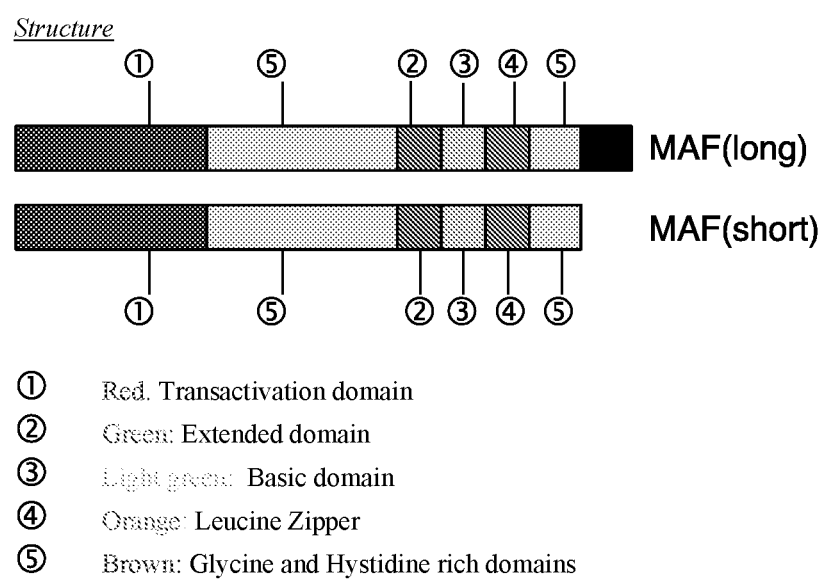
FIG. 1 illustrates a comparison of the 2 isoforms of c-MAF—the short isoform (MAF(short)), and the long isoform (MAF(long)).

"And/or" where used herein is to be taken as specific disclosure of each of the two specified features or components with or without the other. For example 'A and/or B' is to be taken as specific disclosure of each of (i) A, (ii) B and (iii) A and B, just as if each is set out individually herein.

As used herein, "binding member" describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, receptor-ligand and enzyme-substrate. In some embodiments, the binding member is an antibody. In some embodiments, the binding member is an antibody that binds a c-MAF antigen.

As used herein, "CDR region" or "CDR" is intended to indicate the hypervariable regions of the heavy and light chains of the immunoglobulin as defined by Kabat et al., (1991) Sequences of Proteins of Immunological Interest, 5th Edition. US Department of Health and Human Services, Public Service, NIH, Washington. An antibody typically contains 3 heavy chain CDRs, termed HCDR1, HCDR2, and HCDR3, and 3 light chain CDRs, termed LCDR1, LCDR2 and LCDR3. The term CDR or CDRs is used here in order to indicate one of these regions or several, or even the whole, of these regions which contain the majority of the amino acid residues responsible for the binding by affinity of the antibody for the antigen or the epitope which it recognizes. Among the six CDR sequences, the third CDR of the heavy chain (HCDR3) has a greatest size variability i.e. greater diversity, essentially due to the mechanism known in the art as V(D)J rearrangement of the V, D and J gene segments of the germline immunoglobulin heavy chain gene locus. The HCDR3 may be as short as two amino acids or as long as 26 amino acids, or may have any length in between these two extremes. CDR length may also vary according to the length that can be accommodated by the particular underlying framework. Functionally, HCDR3 can play an important role in the determination of the specificity of the antibody (Segal et al., (1974) *Proc Natl Acad Sci USA.* 71(11): 4298-302; Amit et al., (1986) *Science* 233(4765): 747-53; Chothia et al., (1987) *J. Mol. Biol.* 196(4): 901-17; Chothia et al., (1989) Nature 342(6252): 877-83; Caton et al., (1990) *J. Immunol.* 144(5): 1965-8; Sharon (1990a) *PNAS USA.* 87(12): 4814-7, Sharon (1990b) J. *Immunol.* 144: 4863-4869, Kabat et al., (1991) Sequences of Proteins of Immunological Interest, 5th Edition. US Department of Health and Human Services, Public Service, NIH, Washington).

As used herein, "antibody", "antibody molecule", or "antibodies" describes an immunoglobulin whether naturally, or partly, or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids. Antibody fragments that comprise an antibody antigen-binding site include, but are not limited to, molecules such as Fab, Fab', F(ab')$_2$, Fab'-SH, scFv, Fv, dAb and Fd. Various other antibody molecules including one or more antibody antigen-binding sites have been engineered, including for example Fab2, Fab3, diabodies, triabodies, tetrabodies, camelbodies, nanobodies and minibodies. Antibody molecules and methods for their construction and use are described in Hollinger & Hudson (2005) *Nature Biot.* 23(9): 1126-1136.

As used herein, "antibody molecule" should be construed as covering any binding member or substance having an antibody antigen-binding site with the required specificity and/or binding to antigen. Thus, this term covers functional antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described for example in EP0120694A (Boss et al) and EP0125023A (Cabilly et al), which are incorporated herein in their entirety.

As used herein, "functional fragment or variant" of, for example, a binding member of the present invention means a fragment or variant of a binding member that retains at least some function of a full binding member (e.g., the ability to specifically bind to antigen such as Maf).

As used herein, the term "amplification of a gene" refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, i.e., the gene expression level, also increases in proportion to the copy number of a particular gene.

As used herein, "MAF gene", "Maf", "c-MAF" or "c-Maf" (v-Maf musculoaponeurotic fibrosarcoma oncogene homologue (avian) also known as Maf or MGC71685) is a transcription factor containing a leucine zipper which acts like a homodimer or a heterodimer. Depending on the DNA binding site, the encoded protein can be a transcriptional activator or repressor. The DNA sequence encoding MAF is described in the NCBI database under accession number NG_016440 (SEQ ID NO: 1 (coding)). The genomic sequence of MAF is set forth in SEQ ID NO:13. The methods of the present invention may utilize either the coding sequence or the genomic DNA sequence. Two messenger RNA are transcribed from said DNA sequence, each of which will give rise to one of the two c-MAF protein isoforms, the a isoform and the β isoform. The complementary DNA sequences of each of said isoforms are described, respectively, in the NCBI database under accession numbers NM_005360.4 (SEQ ID NO: 2) and NM_001031804.2 (SEQ ID NO: 3). More information about the isoforms of c-MAF can be found in Eychene et al., *NRC* 8: 683-693 (2008), which is incorporated herein by reference in its entirety. In some embodiments, the invention is directed to use of the c-MAF gene to predict the prognosis of cancer generally, for example, Int'l. Appl. Nos. PCT/IB2013/001204 and PCT/ES2011/070693 and U.S. application Ser. No. 13/878,114 and Ser. No. 13/878,114 (triple-negative breast cancer and ER+ breast cancer), Int'l Appl. No. PCT/US2014/026154 (renal cell carcinoma), Int'l Appl. No.

PCT/US2014/028722 (breast cancer), Int'l Appl. No. PCT/US2013/044584 (lung cancer), U.S. application Ser. No. 14/050,262 and Int'l Appl. No. PCT/IB2013/002866 (prostate cancer), Int'l Appl. No. PCT/US2014/059506 (HER2+ breast cancer), U.S. application Ser. No. 14/213,670 and Int'l Appl. No. PCT/US2014/028569 (metastatic cancer), each of which is incorporated here by reference in its entirety.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, i.e., to act as a DNA binding transcription factor. Variants of the c-MAF protein can be identified using methods based on the capacity of c-MAF for promoting in vitro cell proliferation as shown in Int'l Pat. Publ. WO2005/046731 (incorporated herein by reference in its entirety), based on the capacity of an inhibitor or test compound for blocking the transcription capacity of a reporter gene under the control of cyclin D2 promoter or of a promoter containing the c-MAF responsive region (MARE or c-MAF responsive element) in cells expressing c-MAF as described in Int'l Pat. Publ. WO2008/098351 (incorporated herein by reference in its entirety). Variants of c-MAF can also be identified based on the capacity of an inhibitor for blocking reporter gene expression under the control of the IL-4 promoter in response to the stimulation with PMA/ionomycin in cells expressing NFATc2 and c-MAF as described in U.S. Publ. No. US2009/048117A (incorporated herein by reference in its entirety).

c-MAF variants according to the invention preferably have sequence similarity with the amino acid sequence of any of the c-MAF protein isoforms (SEQ ID NO: 4 or SEQ ID NO: 5) of at least about 50%, at least about 60%, at least about 70%, at least about 80%, at least about 90%, at least about 91%, at least about 92%, at least about 93%, at least about 94%, at least about 95%, at least about 96%, at least about 97%, at least about 98% or at least about 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

As used herein, Mammalian target of rapamycin (mTOR) or "mTor" refers to those proteins that correspond to EC 2.7.11.1. mTor enzymes are serine/threonine protein kinases and regulate cell proliferation, cell motility, cell growth, cell survival, and transcription.

As used herein, an "mTor inhibitor" refers to any molecule capable of completely or partially inhibiting the mTor gene expression, both by preventing the expression product of said gene from being produced (interrupting the mTor gene transcription and/or blocking the translation of the mRNA coming from the mTor gene expression) and by directly inhibiting the mTor protein activity. Including inhibitors that have a dual or more targets and among them mTor protein activity.

As used herein, "Src" refers to those proteins that correspond to EC 2.7.10.2. Src is a non-receptor tyrosine kinase and a proto-oncogene. Src may play a role in cell growth and embryonic development.

As used herein, a "Src inhibitor" refers to any molecule capable of completely or partially inhibiting Src gene expression, both by preventing the expression product of said gene from being produced (interrupting the Src gene transcription and/or blocking the translation of the mRNA coming from the Src gene expression) and by directly inhibiting the Src protein activity.

As used herein, "Prostaglandin-endoperoxide synthase 2", "cyclooxygenase-2" or "COX-2" refers to those proteins that correspond to EC 1.14.99.1. COX-2 is responsible for converting arachidonic acid to prostaglandin endoperoxide H2.

As used herein, a "COX-2 inhibitor" refers to any molecule capable of completely or partially inhibiting COX-2 gene expression, both by preventing the expression product of said gene from being produced (interrupting the COX-2 gene transcription and/or blocking the translation of the mRNA coming from the COX-2 gene expression) and by directly inhibiting the COX-2 protein activity.

As used herein "outcome" or "clinical outcome" refers to the resulting course of disease and/or disease progression and can be characterized for example by recurrence, period of time until recurrence, metastasis, period of time until metastasis, number of metastases, number of sites of metastasis and/or death due to disease. For example a good clinical outcome includes cure, prevention of recurrence, prevention of metastasis and/or survival within a fixed period of time (without recurrence), and a poor clinical outcome includes disease progression, metastasis and/or death within a fixed period of time.

As used herein, the term "expression level" of a gene refers to the measurable quantity of gene product produced by the gene in a sample of the subject, wherein the gene product can be a transcriptional product or a translational product. Accordingly, the expression level can pertain to a nucleic acid gene product such as mRNA or cDNA or a polypeptide gene product. The expression level is derived from a subject's sample and/or a reference sample or samples, and can for example be detected de novo or correspond to a previous determination. The expression level can be determined or measured, for example, using microarray methods, PCR methods (such as qPCR), and/or antibody based methods, as is known to a person of skill in the art. In some embodiments, the expression level of c-MAF is measured using an antibody disclosed herein.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

"Increased expression level" is understood as the expression level when it refers to the levels of the MAF gene greater than those in a reference sample or control sample. Increased levels can be caused without excluding other mechanisms by a gene or 16q23 or 16q22-24 chromosomal locus amplification or translocation. Particularly, a sample can be considered to have high c-MAF expression level when the expression level in the sample isolated from the patient is at least about 1.1 times, about 1.5 times, about 5 times, about 10 times, about 20 times, about 30 times, about 40 times, about 50 times, about 60 times, about 70 times, about 80 times, about 90 times, about 100 times or even more with respect to the reference or control.

"Probe", as used herein, refers to an oligonucleotide sequence that is complementary to a specific nucleic acid sequence of interest. In some embodiments, the probes may be specific to regions of chromosomes which are known to undergo translocations. In some embodiments, the probes have a specific label or tag. In some embodiments, the tag is a fluorophore. In some embodiments, the probe is a DNA in situ hybridization probe whose labeling is based on the stable coordinative binding of platinum to nucleic acids and proteins. In some embodiments, the probe is described in U.S. patent application Ser. No. 12/067,532 and U.S. patent application Ser. No. 12/181,399, which are incorporated by reference in their entirety, or as described in Swennenhuis et al. "Construction of repeat-free fluorescence in situ hybridization probes" *Nucleic Acids Research* 40(3):e20 (2012).

"Tag" or "label", as used herein, refers to any physical molecule which is directly or indirectly associated with a probe, allowing the probe or the location of the probed to be visualized, marked, or otherwise captured.

"Translocation", as used herein, refers to the exchange of chromosomal material in unequal or equal amounts between chromosomes. In some cases, the translocation is on the same chromosome. In some cases, the translocation is between different chromosomes. Translocations occur at a high frequency in many types of cancer, including breast cancer and leukemia. Translocations can be either primary reciprocal translocations or the more complex secondary translocations. There are several primary translocations that involve the immunoglobin heavy chain (IgH) locus that are believed to constitute the initiating event in many cancers. (Eychène, A., Rocques, N., and Puoponnot, C., A new MAFia in cancer. 2008. *Nature Reviews: Cancer.* 8: 683-693.)

"Polyploid" or "polyploidy", as used herein, indicates that the cell contains more than two copies of a gene of interest. In some instances, the gene of interest is MAF. In some embodiments, polyploidy is associated with an accumulation of expression of the gene of interest. In some embodiments, polyploidy is associated with genomic instability. In some embodiments, the genomic instability may lead to chromosome translocations.

"Whole genome sequencing", as used herein, is a process by which the entire genome of an organism is sequenced at a single time. See, e.g., Ng., P. C. and Kirkness, E. F., Whole Genome Sequencing. 2010. *Methods in Molecular Biology.* 628: 215-226.

"Exome sequencing", as used herein, is a process by which the entire coding region of the DNA of an organism is sequenced. In exome sequencing, the mRNA is sequenced. The untranslated regions of the genome are not included in exome sequencing. See, e.g., Choi, M. et al., Genetic diagnosis by whole exome capture and massively parallel DNA sequencing. 2009. *PNAS.* 106(45): 19096-19101.

"Metastasis", as used herein, is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a breast cancer, for example, spreads (metastasizes) to the lung, the secondary tumor is formed of malignant breast cancer cells. The disease in the lung is metastatic breast cancer and not lung cancer.

"Predicting", as used herein, refers to the determination of the likelihood that the subject suffering from cancer will develop metastasis to a distant organ. As used herein, "good prognosis" indicates that the subject is expected (e.g. predicted) to survive and/or have no, or is at low risk of having, recurrence or distant metastases within a set time period. The term "low" is a relative term and, in the context of this application, refers to the risk of the "low" expression group with respect to a clinical outcome (recurrence, distant metastases, etc.). A "low" risk can be considered as a risk lower than the average risk for an heterogeneous cancer patient population. In the study of Paik et al. (2004), an overall "low" risk of recurrence was considered to be lower than 15 percent. The risk will also vary in function of the time period. The time period can be, for example, five years, ten years, fifteen years or even twenty years after initial diagnosis of cancer or after the prognosis was made.

As used herein, "poor prognosis" indicates that the subject is expected, e.g. predicted, to not survive and/or to have, or is at high risk of having, recurrence or distant metastases within a set time period. The term "high" is a relative term and, in the context of this application, refers to the risk of the "high" expression group with respect to a clinical outcome (recurrence, distant metastases, etc.). A "high" risk can be considered as a risk higher than the average risk for a heterogeneous cancer patient population. In the study of Paik et al. (2004), an overall "high" risk of recurrence was considered to be higher than 15 percent. The risk will also vary in function of the time period. The time period can be, for example, five years, ten years, fifteen years or even twenty years of initial diagnosis of cancer or after the prognosis was made.

"Reference value", as used herein, refers to a laboratory value used as a reference for values/data obtained by laboratory examinations of patients or samples collected from patients. The reference value or reference level can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested.

As used herein, "Subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

The term "treatment", as used herein, refers to any type of therapy, which aims at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency. In some embodiments, the treatment is to prevent bone degradation. In some embodiments, the treatment is any treatment disclosed or considered in Int'l. Appl. No. PCT/IB2013/001204, U.S. Prov. Appl. No. 61/801,769, U.S. Prov. Appl. No. 61/801,642, U.S. Prov. Appl. No. 61/801,718, Int'l Appl. No. PCT/US2013/044584, U.S. Prov. Appl. No. 61/713,318, and Int'l Appl. No. PCT/US2014/059506 which are incorporated here by reference in its entirety.

As used herein, "sample" or "biological sample" means biological material isolated from a subject. The biological sample may contain any biological material suitable for determining the expression level of the c-MAF gene. The sample can be isolated from any suitable biological tissue or fluid such as, for example, tumor tissue, blood, blood plasma, serum, urine or cerebral spinal fluid (CSF).

"Tumor tissue sample" is understood as the tissue sample originating from the primary cancer tumor. Said sample can be obtained by conventional methods, for example biopsy, using methods well known by the persons skilled in related medical techniques.

"Osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Binding Members

A binding member normally comprises a molecule having a binding site. For example, a binding member may be an antibody molecule or a non-antibody protein that comprises a binding site. A binding site may be provided by means of arrangement of CDRs on antibody framework regions and/or on non-antibody protein scaffolds, such as fibronectin or cytochrome B etc. (Haan & Maggos (2004) *BioCentury*, 12(5): A1-A6; Koide et al., (1998) *J. Mol. Biol.* 284: 1141-1151; Nygren et al., (1997) *Curr. Op. Struct. Biol.* 7: 463-469), or by randomizing or mutating amino acid residues of a loop within a protein scaffold to confer binding specificity for a desired target. Scaffolds for engineering novel binding sites in proteins have been reviewed in detail by Nygren et al., ibid. Protein scaffolds for antibody mimics are disclosed in WO 00/034784 A1 (Lipovsek), in which the inventors describe proteins (antibody mimics) that include a fibronectin type III domain having at least one randomized loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, (2004) In: *BioCentury, The Bernstein Report on BioBusiness*, 12(42), A1-A7. Typical are proteins having a stable backbone and one or more variable loops, in which the amino acid sequence(s) of the loop or loops is/are specifically or randomly mutated to create an antigen-binding site that binds the target. Such proteins include the IgG-binding domains of protein A from *S. aureus*, transferrin, tetranectin, fibronectin, lipocalins as well as gamma-crystalline and other Affilin™ scaffolds (Scil Proteins).

Examples of other approaches include synthetic 'Microbodies' based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

In some embodiments, the binding member is an antibody. Although, as noted, the CDRs of the antibody can be carried by non-antibody scaffolds, the structure for carrying a CDR or a set of CDRs of the invention will often be an antibody heavy or light chain sequence or substantial portion thereof in which the CDR or set of CDRs is located at a location corresponding to the CDR or set of CDRs of naturally occurring $V_H$ and $V_L$ antibody variable domains encoded by rearranged immunoglobulin genes. The structures and locations of immunoglobulin variable domains may be determined by reference to Kabat et al., (1991), ibid and updates thereof. A number of academic and commercial on-line resources are available to query this database. For example, see Martin, (1996) *PROTEINS: Structure, Function and Genetics*, 25:130-133 and the associated on-line resource, currently at the web address of http://www.bioinf.org.uk/abs/simkab.html.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP0184187A (Kudo et al) or EP0239400A (Winter). A hybridoma or other cell producing an antibody may be subject to genetic mutation or other changes, which may or may not alter the binding specificity of antibodies produced.

Further techniques available in the art of antibody engineering have made it possible to isolate human and humanized antibodies. For example, human hybridomas can be made as described by Kontermann & Dubel (2001) *Antibody Engineering*, Springer-Verlag New York, LLC; ISBN: 3540413545. Phage display, another established technique for generating binding members has been described in detail in many publications, such as Kontermann & Dubel, ibid and WO 92/01047 A1 (McCafferty et al).

Transgenic mice in which the mouse antibody genes are inactivated and functionally replaced with human antibody genes while leaving intact other components of the mouse immune system, can be used for isolating human antibodies (Mendez et al., (1997) Nature Genet. 15(2): 146-156). Alternatively, the method described by Grawunder & Melchers (WO 03/068819 A1) can be used to generate genetically modified vertebrate precursor lymphocytes for the production of heterologous antibodies or binding proteins. In some embodiments, rabbits are used to generate the antibodies. In some embodiments, the antibody is generated using a hybridoma supernatant, a recombinant antibody-transient expression method, or a recombinant antibody—stable cell line development and production method. In some embodiments, the antibody is optionally purified with Protein A. Humanized antibodies can be produced using techniques known in the art such as those disclosed in for example WO 91/09967 A1 (Adair et al). Further, WO 04/006955 A1 (Foote) describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 04/006955 A1 ibid, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

It has been shown that fragments of a whole antibody can perform the function of binding antigens. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment (Ward et al., (1989) Nature 341(6242): 544-6; McCafferty et al., (1990) Nature 348(6301): 552-4; Holt et al., (2003) Trends in Biotechnology 21:484-490), which consists of a $V_H$ or a $V_L$ domain; (v) isolated CDR regions; (vi) F(ab')$_2$ fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site (Bird et al., (1998) Science 242(4877): 423-6; Huston et al., (1988) PNAS USA, 85: 5879-5883); (viii) bispecific single chain Fv dimers (WO 93/011161 A1 (Whitlow et al.)) and (ix) 'diabodies', multivalent or multispecific fragments constructed by gene fusion (Holliger et al., 1993) PNAS USA. 90(14): 6444-8 & WO 94/13804 A1). Fv, scFv or diabody molecules may be stabilized by the incorporation of disulphide bridges linking the $V_H$ and $V_L$ domains (Reiter et al., (1996) Nature Biotech, 14: 1239-1245). Minibodies comprising an scFv joined to a $C_H3$ domain may also be made (Hu et al, (1996) Cancer Res. 56: 3055-3061). Other examples of binding fragments are Fab', which differs from Fab fragments by the addition of a few residues at the carboxyl terminus of the heavy chain $C_H1$ domain, including one or more cysteines from the antibody hinge region, and Fab'-SH, which is a Fab' fragment in which the cysteine residue(s) of the constant domains bear a free thiol group. Antibody molecules have also been described that containing just two CDRs linked by a framework region (Qui et al., (2007) Nat. Biotechnol. 25:921-929). CDR3 from the $V_H$ or $V_L$ domain was linked to the CDR1 or CDR2 loop of the other domain with linkage through the C terminus of the selected CDR1 or CDR2 to the N terminus of the CDR3, via a FR region.

A domain antibody (dAb) is a small monomeric antigen-binding fragment of an antibody, namely the variable region of an antibody heavy or light chain (Holt et al., (2003) Trends in Biotechnology 21: 484-490). $V_H$ dAbs occur naturally in camelids (e.g. camel, llama) and may be produced by immunizing a camelid with a target antigen, isolating antigen-specific B cells and directly cloning dAb genes from individual B cells; however dAbs can also be produced in cell culture. A binding member of the present invention may be a dAb comprising a $V_H$ or $V_L$ domain substantially as set out herein, or a $V_H$ or $V_L$ domain comprising a set of CDRs substantially as set out herein.

Antibody fragments of the invention can be obtained starting from any of the antibodies disclosed herein, by methods such as digestion by enzymes e.g. pepsin or papain and/or by cleavage of the disulfide bridges by chemical reduction. In another manner, the antibody fragments comprised in the present invention can be obtained by techniques of genetic recombination well known to the person skilled in the art or else by peptide synthesis or by nucleic acid synthesis and expression.

Functional antibody fragments according to the present invention include any functional fragment whose half-life is increased by a chemical modification, especially by PEGylation, or by incorporation in a liposome for example.

Bispecific or bifunctional antibodies form a second generation of monoclonal antibodies in which two different variable regions are combined in the same molecule (Holliger & Bohlen, (1999) Cancer & Metastasis Rev. 18: 411-419). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger & Winter, (1993) Curr. Op. Biotech. 4: 446-449). Examples of bispecific antibodies include those of the BiTE® technology (Micromet, Inc.) in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific F(ab')$_2$, as Fab'PEG, as diabodies or else as bispecific scFv. Further, two bispecific antibodies can be linked using routine methods known in the art to form tetravalent antibodies. Bispecific diabodies, as opposed to bispecific whole antibodies, may also be particularly useful because they can be readily constructed and expressed in E. coli.

As noted above, in some embodiments, a binding member in accordance with the present invention is an antibody that binds to c-MAF. A high potency binding member may be obtained directly from an initial screen. Assays and potencies are described in more detail elsewhere herein.

In some embodiments, the binding member is an antigen binding molecule or fragment thereof that binds to human c-MAF, wherein the antibody binding molecule or fragment thereof comprises a heavy chain CDR1 at least about 70%, about 75%, about 80%, about 85%, about 90%, about 95%, about 99% or about 100% identical to the amino acid sequence of SEQ ID NO: 38, and/or a heavy chain CDR2 at least about 70%, about 75%, about 80%, about 85%, about 90%, about 95%, about 99% or about 100% identical to the amino acid sequence of SEQ ID NO: 40, and/or a heavy chain CDR3 at least about 70%, about 75%, about 80%, about 85%, about 90%, about 95%, about 99% or about 100% identical to the amino acid sequence of SEQ ID NO: 42; and/or comprising a light chain CDR1 at least about 70%, about 75%, about 80%, about 85%, about 90%, about 95%, about 99% or about 100% identical to the amino acid sequence of SEQ ID NO: 26, and/or a light chain CDR2 at least about 70%, about 75%, about 80%, about 85%, about 90%, about 95%, about 99% or about 100% identical to the amino acid sequence of SEQ ID NO: 28 and/or a light chain CDR3 at least about 70%, about 75%, about 80%, about 85%, about 90%, about 95%, about 99% or about 100% identical to the amino acid sequence of SEQ ID NO: 30.

In some embodiments, the antigen binding molecule or fragment thereof is an antibody. In some embodiments, the antibody is a rabbit antibody, a mouse antibody, a chimeric antibody or a humanized antibody.

In some embodiments, the antibody or fragment thereof comprises a $V_H$ domain with a sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 17.

In some embodiments, the antigen binding molecule or fragment thereof comprises a $V_L$ domain with a sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 21.

In some embodiments, the antibody or fragment thereof comprises a heavy chain sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 16.

In some embodiments, the antibody or fragment thereof comprises a light chain sequence that is at least about 70%, at least about 75%, at least about 80%, at least about 85%, at least about 90%, at least about 95%, at least about 99%, at least about 99%, or at least about 100% identical to the amino acid sequence of SEQ ID NO: 20.

In some embodiments, an antibody $V_H$ variable domain with the amino acid sequence of a said selected binding member may be provided in isolated form, as may a binding member comprising such a $V_H$ domain. In some embodiments, an antibody $V_L$ variable domain with the amino acid sequence of a said selected binding member may be provided in isolated form, as may a binding member comprising such a $V_L$ domain. In some embodiments, the binding member is a variant of any binding member disclosed herein. In some embodiments, the $V_H$ and/or $V_L$ domains are variants of any $V_H$ and/or $V_L$ domains disclosed herein.

The ability to bind c-MAF may be further tested, also the ability to compete with any antibody molecule of the present invention for binding to c-MAF. Binding affinity of different binding members can be compared under appropriate conditions.

Variants of the $V_H$ and $V_L$ domains and CDRs of the present invention, including those for which amino acid sequences are set out herein, and which can be employed in binding members of the invention can be obtained by means of methods of sequence alteration or mutation and screening for antigen binding members with desired characteristics. Examples of desired characteristics include but are not limited to:

Increased binding affinity for antigen relative to known antibodies which are specific for the antigen Increased neutralization of an antigen activity relative to known antibodies which are specific for the antigen if the activity is known Specified competitive ability with a known antibody or ligand to the antigen at a specific molar ratio Ability to immunoprecipitate complex Ability to bind to a specified epitope such as a linear epitope, e.g. using peptides screened in linear and/or constrained conformation or conformational epitope, formed by non-continuous residues Ability to modulate a new biological activity of c-MAF, or a downstream molecule. Such methods are also provided herein.

In some embodiments, the binding member binds to the antigen c-MAF. In some embodiments, the binding member binds to human c-MAF. In some embodiments, the binding member binds to an epitope corresponding to 83-EQKAHL-EDYYWMTGYPQQ-100 (18 a.a.) of c-MAF of human origin (SEQ ID NO: 22)

An antibody antigen-binding site composed of a $V_H$ domain and a $V_L$ domain is typically formed by six loops of polypeptide: three from the light chain variable domain ($V_L$) and three from the heavy chain variable domain ($V_H$). Analysis of antibodies of known atomic structure has elucidated relationships between the sequence and three-dimensional structure of antibody combining sites. These relationships imply that, except for the third region (loop) in $V_H$ domains, binding site loops have one of a small number of main-chain conformations or canonical structures. The canonical structure formed in a particular loop has been shown to be determined by its size and the presence of certain residues at key sites in both the loop and in framework regions (Chothia et al., (1992) *J. Molecular Biology* 227: 799-817; Al-Lazikani et al., (1997) *J. Mol. Biol.* 273(4): 927-948).

This study of sequence-structure relationship can be used for prediction of those residues in an antibody of known sequence, but of an unknown three-dimensional structure, which are important in maintaining the three-dimensional structure of its CDR loops and hence maintain binding specificity. In a structural approach, a model can be created of the antibody molecule (Chothia et al., (1986) *Science* 223: 755-758) using any freely available or commercial package, such as WAM (Whitelegg & Rees, (2000) *Prot. Eng.* 12: 815-824). A protein visualization and analysis software package, such as Insight II (Accelrys, Inc.) or Deep View (Guex & Peitsch, (1997) *Electrophoresis* 18: 2714-2723) may then be used to evaluate possible substitutions at each position in the CDR. This information may then be used to make substitutions likely to have a minimal or beneficial effect on activity.

The techniques required to make substitutions within amino acid sequences of CDRs, antibody $V_H$ or $V_L$ domains and binding members generally are available in the art. Variant sequences may be made, with substitutions that may or may not be predicted to have a minimal or beneficial effect on activity, and tested for ability to bind c-MAF and/or for any other desired property.

Variable domain amino acid sequence variants of any of the $V_H$ and $V_L$ domains whose sequences are specifically disclosed herein may be employed in accordance with the present invention, as discussed.

A further aspect of the invention is an antibody molecule comprising a $V_H$ domain that has at least about 60, about 70, about 80, about 85, about 90, about 95, about 98 or about 99% amino acid sequence identity with a $V_H$ domain of any of antibodies shown in the appended sequence listing (e.g., SEQ ID NO. 17), and/or comprising a $V_L$ domain that has at least about 60, about 70, about 80, about 85, about 90, about 95, about 98 or about 99% amino acid sequence identity with a $V_L$ domain of any of antibodies in the appended sequence listing (e.g., SEQ ID NO. 21). Algorithms that can be used to calculate % identity of two amino acid sequences include e.g. BLAST (Altschul et al., (1990) *J. Mol. Biol.* 215(3): 403-10), FASTA (Pearson & Lipman, (1988) PNAS USA 85(8): 2444-8), or the Smith-Waterman algorithm (Smith & Waterman, (1981) *J. Mol. Biol.* 147(1): 195-7), e.g. employing default parameters. Particular variants may include one or more amino acid sequence alterations (addition, deletion, substitution and/or insertion of an amino acid residue).

Alterations may be made in one or more framework regions and/or one or more CDRs. The alterations normally do not result in loss of function, so a binding member comprising a thus-altered amino acid sequence may retain an ability to bind c-MAF. It may retain the same quantitative binding ability as a binding member in which the alteration is not made, e.g. as measured in an assay described herein. The binding member comprising a thus-altered amino acid sequence may have an improved ability to bind c-MAF.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 'standard' L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine (Voet & Voet, *Biochemistry*, 3rd Edition, (Wiley) 2004). Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the 'original' standard amino acids after synthesis of the amino acid sequence.

Use of non-standard and/or non-naturally occurring amino acids increases structural and functional diversity, and can thus increase the potential for achieving desired c-MAF-binding properties in a binding member of the invention. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Novel $V_H$ or $V_L$ regions carrying CDR-derived sequences of the invention may be generated using random mutagenesis of one or more selected $V_H$ and/or $V_L$ genes to generate mutations within the entire variable domain. Such a technique is described by Gram et al., (1992), who used error-prone PCR. In some embodiments one or two amino acid substitutions are made within an entire variable domain or set of CDRs. Another method that may be used is to direct mutagenesis to CDR regions of $V_H$ or $V_L$ genes (Barbas et al., (1994) *PNAS USA* 91: 3809-3813; Schier et al., (1996) *J. Mol. Biol.* 263: 551-567).

All the above-described techniques are known as such in the art and the skilled person will be able to use such techniques to provide binding members of the invention using routine methodology in the art.

A further aspect of the invention provides a method for obtaining an antibody antigen-binding site for c-MAF, the method comprising providing by way of addition, deletion, substitution or insertion of one or more amino acids in the amino acid sequence of a $V_H$ domain set out herein a $V_H$ domain which is an amino acid sequence variant of the $V_H$ domain, optionally combining the $V_H$ domain thus provided with one or more $V_L$ domains, and testing the $V_H$ domain or $V_H/V_L$ combination or combinations to identify a binding member or an antibody antigen-binding site for c-MAF and optionally with one or more desired properties, e.g. ability to bind c-MAF. Said $V_L$ domain may have an amino acid sequence which is substantially as set out herein. An analogous method may be employed in which one or more sequence variants of a $V_L$ domain disclosed herein are combined with one or more $V_H$ domains. In some embodiments, the variant of the $V_L$ or $V_H$ domain is a functional variant. As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof.

Similarly, one or more, or all three CDRs may be grafted into a repertoire of $V_H$ or $V_L$ domains that are then screened for a binding member or binding members for c-MAF.

For example, one or more of antibody HCDR1, HCDR2 and HCDR3 or set of HCDRs may be employed (SEQ ID NOs 38, 40, and 42), and/or one or more of antibody LCDR1, LCDR2 and LCDR3 or set of LCDRs may be employed (SEQ ID NOs 26, 28, and 30). Similarly, other $V_H$ and V$_L$ domains, sets of CDRs and sets of HCDRs and/or sets of LCDRs disclosed herein may be employed.

Other manipulation steps include the introduction of linkers to join variable domains of the invention to further protein sequences including antibody constant regions, other variable domains or detectable/functional labels as discussed in more detail elsewhere herein.

Although in some aspects of the invention, binding members comprise a pair of V$_H$ and V$_L$ domains, single binding domains based on either V$_H$ or V$_L$ domain sequences form further aspects of the invention. It is known that single immunoglobulin domains, especially V$_H$ domains, are capable of binding target antigens in a specific manner. In the case of either of the single binding domains, these domains may be used to screen for complementary domains capable of forming a two-domain binding member able to bind c-MAF. This may be achieved by phage display screening methods using the so-called hierarchical dual combinatorial approach as disclosed in WO92/01047 (McCafferty et al) and in Marks et al., (1992) *Biotechnology* 10(7): 779-83.

Binding members of the present invention may further comprise antibody constant regions or parts thereof, e.g. human antibody constant regions or parts thereof. For example, a V$_L$ domain may be attached at its C-terminal end to antibody light chain constant domains. Similarly, a binding member based on a V$_H$ domain may be attached at its C-terminal end to all or part (e.g. a C$_H$1 domain) of an immunoglobulin heavy chain derived from any antibody isotype, e.g. IgG, IgA, IgE and IgM and any of the isotype sub-classes, particularly IgG$_1$ and IgG$_4$. IgG$_1$ is advantageous, due to its effector function and ease of manufacture. Any synthetic or other constant region variant that has these properties and stabilizes variable regions may also be useful in the present invention.

Binding members of the present invention may also include antibodies or fragments comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity. Fc region refers to naturally occurring or synthetic polypeptides homologous to the IgG C-terminal domain that is produced upon papain digestion of IgG. IgG Fc has a molecular weight of approximately 50 kD. For antibodies and/or fragments of the present invention, an entire Fc region can be used, or only a half-life enhancing portion.

The Fc region can be mutated, if desired, to inhibit its ability to fix complement and bind the Fc receptor with high affinity. In an embodiment of the present invention, antibodies or fragments may be provided with a modified Fc region where a naturally occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253 (Presta & Snedecor). Effector functions that can be altered (e.g., enhanced) by making modifications to the Fc region, either by modifying glycosylation patterns or by modifying the amino acid sequence of the Fc region, include, but are not limited to: such as complement-dependent cytotoxicity (CDC), antibody-dependent cellular cytotoxicity (ADCC) and antibody-dependent cell phagocytosis (ADCP). Potential modifications include insertion, deletion or substitution of one or more amino acid residues, including substitution with alanine, a conservative substitution, a non-conservative substitution, or replacement with a corresponding amino acid residue at the same position from a different IgG subclass (e.g. replacing an IgG$_1$ residue with a corresponding IgG$_2$ residue at that position).

Thus, in a further aspect, the present invention encompasses a c-MAF binding member as described elsewhere herein, wherein said binding member comprises an Fc region or an equivalent region that comprises at least an IgG CH2 region, that has been modified to increase one or more effector functions. In one embodiment, the binding member is modified to alter the glycosylation pattern of the N-linked oligosaccharides such that the activity of one or more effector functions is increased. In another embodiment, the binding member is modified to alter the amino acid sequence of the Fc region such that the activity of one or more effector functions is increased. Methods of measuring effector function activity and determining whether or not they are increased are well known in the art.

Binding members of the present invention may be labeled with a detectable or functional label. Thus, a binding member or antibody molecule can be present in the form of an immunoconjugate so as to obtain a detectable and/or quantifiable signal. An immunoconjugate may comprise an antibody molecule of the invention conjugated with detectable or functional label. A label can be any molecule that produces or can be induced to produce a signal, including but not limited to fluorochromes, radiolabels, enzymes, chemiluminescers or photosensitizers. Thus, binding may be detected and/or measured by detecting fluorescence or luminescence, radioactivity, enzyme activity or light absorbance. Illustrative examples of labels that can be used include radioactive isotopes, enzymes, fluorochromes, chemiluminescence reagents, enzyme substrates or cofactors, enzyme inhibitors, particles, dyes, etc.

Suitable labels include, by way of illustration and not limitation, enzymes, such as alkaline phosphatase, glucose-6-phosphate dehydrogenase ('G6PDH'), alpha-D-galactosidase, glucose oxydase, glucose amylase, carbonic anhydrase, acetylcholinesterase, lysozyme, malate dehydrogenase and peroxidises, e.g. horseradish peroxidase; dyes; fluorescent labels or fluorochromes, such as fluorescein and its derivatives, rhodamine compounds and derivatives, green/yellow fluorescent protein (G/YFP), red fluorescent protein (RFP), blue fluorescent protein (BFP), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational), chemoluminescent labels or chemiluminescers, such as isoluminol, luminol and the dioxetanes; bio-luminescent labels, such as luciferase and luciferin; sensitizers; coenzymes; enzyme substrates; radiolabels including but not limited to bromine77, carbon14, cobalt57, fluorine8, gallium67, gallium 68, hydrogen3 (tritium), indium111, indium113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in U.S. Pat. No. 4,275,149 (Litman et al) and U.S. Pat. No. 4,318,980 (Boguslaski et al) and suitable fluorescers and chemiluminescers are disclosed in U.S. Pat. No. 4,275,149, which are incorporated herein by reference in their entirety. Labels further include chemical moieties, such as biotin that may be detected via binding to a specific cognate detectable moiety, e.g. labeled avidin or streptavidin, or genetically engineered streptavidin, like streptactin (IBA GmbH, Göttingen, Del.). Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA, mentioned above, can be used for the radio-elements which can be used in diagnosis. It is likewise possible to perform labeling with Iodine-131 by the chloramine T method (Hunter & Greenwood, (1962) Nature 194: 495-6) or else with technetium-99m (Tc-99m) by the technique described in U.S. Pat. No. 4,424,200 (Crockford & Rhodes) or attached via DTPA as described in U.S. Pat. No. 4,479,930 (Hnatowich), both of which are herein incorporated by reference in their entirety.

There are numerous methods by which the label can produce a signal detectable by external means, for example, by visual examination, electromagnetic radiation, heat and chemical reagents. The label can also be bound to another binding member that binds the binding member of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labeled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymatic products, catalysts, activators, co-factors, inhibitors, scavengers, metal ions, and a specific binding substance required for binding of signal generating substances. A detailed discussion of suitable signal producing systems can be found in U.S. Pat. No. 5,185,243 (Ullman et al). The present invention provides a method comprising causing or allowing binding of a binding member as provided herein specific for c-MAF. As noted, such binding may take place in vivo, e.g. following administration of a binding member, or nucleic acid encoding a binding member, or it may take place in vitro, for example in ELISA, Western blotting, affinity chromatography, immunocytochemistry, immunoprecipitation, neutralization and biochemical or cell-based assays.

Determination of the Levels of the Gene of Interest Using an Antibody of the Invention In a preferred embodiment, the binding members (e.g., antibodies) of the present invention are used to quantify c-MAF protein expression levels. c-MAF protein expression level can be quantified by any conventional method which allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. In some embodiments, the antibodies used to detect the c-MAF protein expression level are any antibody described herein. The antibodies used in these assays may or may not be labeled. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. Nevertheless, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, nanobodies, alphabodies, stapled peptides, cyclopeptides and antibodies is preferred. In some embodiments, the antibody is INB-1-11-8, which is described in Example 1. The INB-1-11-8 light chain sequence is SEQ ID NO: 20 and the INB-1-11-8 heavy chain sequence is SEQ ID NO: 16.

The $K_D$ may be determined by surface plasmon resonance, e.g. BIAcore®. Surface plasmon resonance involves passing an analyte in fluid phase over a ligand attached to a solid support, and determining association rates ($k_a$) and dissociation rates ($k_d$) between analyte and ligand. Surface plasmon resonance may for example be performed whereby a binding member is passed in fluid phase over gB protein attached to a support. Biacore allows the extent to which different molecules interact with a single partner immobilized on a sensor surface to be determined, and reveals the specificity of an interaction. Biacore allows for a determination of the association rates ($k_a$) and dissociation rates ($k_d$) between analyte and ligand. The kinetics of an interaction, i.e. the rates of complex formation ($k_a$) and dissociation ($k_d$), can be determined from the information in a sensorgram The affinity may be expressed as the dissociation constant, $K_D$, which is calculated from the ratio of the dissociation and the association rate constants $k_d/k_a$ as determined by surface plasmon resonance using a monovalent analyte data model. In some embodiments, the affinity is the monovalent binding affinity.

In some embodiments, the antibody or fragment thereof described herein binds to human c-MAF with an affinity (KD) of at least about 1 µM, 100 nM, 50 nM, 10 nM, at least about 9 nM, at least about 8 mM, at least about 7 nM, at least about 6 nM, at least about 5 nM, at least about 4 nM, at least about 3 nM, at least about 2.5 nM, at least about 2 nM, at least about 1.9 nM, at least about 1.8 nM, at least about 1.7 nM, at least about 1.6 nM, at least about 1.5 nM, at least about 1.4 nM, at least about 1.3 nM, at least about 1.2 nM, at least about 1.1 nM, at least about 1.0 nM, at least about 0.9 nM, at least about 0.8 nM, at least about 0.7 nM, at least about 0.6 nM, at least about 0.5 nM, at least about 0.4 nM, at least about 0.3 nM, at least about 0.2 nM, at least about 0.1 nM, at least about 75 pM, at least about 50 pM, at least about 25 pM, or at least about 1 pM. In some embodiments, the affinity (KD) of the antibody for c-MAF is between at least about 1 nM and about 1.2 nM, between at least about 1 nM and about 1.5 nM, between at least about 1 nM and about 2.0 nM, between at least about 1 nM and about 3.0 nM, between at least about 1 nM and about 4.0 nM, between at least about 1 nM and about 5.0 nM, between at least about 1 nM and about 6.0 nM, between at least about 1 nM and about 7.0 nM, between at least about 1 nM and about 8.0 nM, between at least about 1 nM and about 9.0 nM, between at least about 1 nM and about 10 nM In some embodiments, between at least about 1 nM and about 50 nM, between at least about 1 nM and about 100 nM, between at least about 1 nM and about 1 µM between at least about 0.1 nM and about 1.5 nM, or between at least about 10 pM and about 1.5 nM. In some embodiments, the antibody or fragment thereof described herein binds to human c-MAF with an affinity (KD) of at least about 1.1 nM.

In a particular embodiment, the c-MAF protein levels are quantified by means of western blot, ELISA or a protein array.

In another particular embodiment, the c-MAF protein levels are quantified from exosomes, circulating DNA or circulating tumor cells. Exosomes are 40-100 nm membrane vesicles secreted by most cell types in vivo and in vitro. Exosomes form in a particular population of endosomes, called multivesicular bodies (MVBs) by inward budding into the lumen of the compartment. Upon fusion of MVBs with the plasma membrane, these internal vesicles are secreted. Exosomes can be isolated from diverse cell lines or body fluids by several methods well known in the art (Théry C. et al., *Curr Protoc Cell Biol.* 2006 April; Chapter 3:Unit 3.22) (the entire contents of which are incorporated by reference herein). Several commercial kits are available for the isolation of exosomes such as ExoQuick™ or ExoTest™.

The present invention provides methods for measuring levels of antigen directly, by employing a binding member according to the invention, e.g. in a biosensor system. For instance, the present invention comprises a method of detecting and/or measuring binding to c-MAF, comprising, (i) exposing said binding member to c-MAF and (ii) detecting binding of said binding member to c-MAF, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of a binding member to c-MAF may be determined. Quantitation may be related to the amount of the antigen in a test sample, which may be of diagnostic interest. Screening for binding and/or the quantitation thereof may be useful, for instance, in screening patients for diseases or disorders referred to herein and/or any other disease or disorder involving aberrant c-MAF expression and/or activity.

A diagnostic method of the invention may comprise (i) obtaining a tissue or fluid sample from a subject, (ii) exposing said tissue or fluid sample to one or more binding members (e.g., antibodies) of the present invention; and (iii) detecting bound c-MAF as compared with a control sample, wherein an increase in the amount of c-MAF binding as compared with the control may indicate c-MAF expression and/or activity. Tissue or fluid samples to be tested include tumor, blood, serum, saliva, urine, sputum, a biopsy material or any tissue suspected of containing Maf. Subjects testing positive for increased c-MAF may also benefit from the treatment methods disclosed later herein. Those skilled in the art are able to choose a suitable mode of determining binding of the binding member to an antigen according to their preference and general knowledge, in light of the methods disclosed herein.

One embodiment comprises in a second step comparing the c-MAF gene expression level obtained in the sample (e.g., tumor sample) from the subject with a reference value.

Once the c-MAF gene expression level in a sample from a subject with cancer has been measured and compared with the reference value, if the expression level of said gene is increased with respect to said reference value, then it can be concluded that said subject has a greater tendency to develop metastasis (e.g., bone metastasis).

The determination of the c-MAF gene expression level should be correlated with the reference value.

In an embodiment, reference value(s) as intended herein may convey absolute quantities of MAF. In another embodiment, the quantity of any one or more biomarkers in a sample from a tested subject may be determined directly relative to the reference value (e.g., in terms of increase or decrease, or fold-increase or fold-decrease). Advantageously, this may allow one to compare the quantity of any one or more biomarkers in the sample from the subject with the reference value (in other words to measure the relative quantity of any one or more biomarkers in the sample from the subject vis-a-vis the reference value) without the need to first determine the respective absolute quantities of said one or more biomarkers.

In a preferred embodiment, the reference value is the c-MAF gene expression level in a control sample or reference sample. Depending on the type of tumor to be analyzed, the exact nature of the control or reference sample may vary. Thus, in the event that a prognosis is to be evaluated, then the reference sample is a sample from cancer that has not metastasized or that corresponds to the median value of the c-MAF gene expression level measured in a tumor tissue collection in biopsy samples from subjects with cancer, which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 100 to preferably more than about 1000 subjects, preferably classified according to the foregoing considerations, for example according to various age categories, are taken as the reference group. The sample collection from which the reference level is derived will preferably be formed by subjects suffering from the same type of cancer as the patient object of the study.

In a particular embodiment the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression level. The "reduced" level of c-MAF can then preferably be assigned to samples wherein the c-MAF expression level is equal to or lower than about the $50^{th}$ percentile in the normal population including, for example, expression level equal to or lower than about the $60^{th}$ percentile in the normal population, equal to or lower than about the $70^{th}$ percentile in the normal population, equal to or lower than about the $80^{th}$ percentile in the normal population, equal to or lower than about the $90^{th}$ percentile in the normal population, and equal to or lower than about the $95^{th}$ percentile in the normal population. The "increased" c-MAF gene expression level can then preferably be assigned to samples wherein the c-MAF gene expression level is equal to or greater than the $50^{th}$ percentile in the normal population including, for example, expression level equal to or greater than about the $60^{th}$ percentile in the normal population, equal to or greater than about the $70^{th}$ percentile in the normal population, equal to or greater than about the $80^{th}$ percentile in the normal population, equal to or greater than about the $90^{th}$ percentile in the normal population, and equal to or greater than about the $95^{th}$ percentile in the normal population.

The reactivities of binding members in a sample may be determined by any appropriate means. A competitive binding assay may be used with radioactive antigen, for example an isotope label such as $^{99}Tc$, $^{14}C$, $^{131}I$, $^{125}I$, $^{3}H$, $^{32}P$ or $^{35}S$, or nonradioactive antigen using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are coloured, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase or horseradish peroxidase detection systems may be employed.

The signals generated by individual binding member-reporter conjugates may be used to derive quantifiable absolute or relative data of the relevant binding member binding in samples (normal and test).

The present invention also provides the use of a binding member (e.g., an antibody) as above for measuring antigen levels (e.g., Maf) in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In various aspects and embodiments, the present invention extends to a binding member that competes for binding to c-MAF with any antibody. Competition between binding members may be assayed in vitro, for example by tagging a specific reporter molecule to one binding member which can be detected in the presence of other untagged binding member(s), to enable identification of binding members which bind the same epitope or an overlapping epitope. Competition may be determined for example using ELISA or by surface plasmon resonance, in which hCMV is immobilized to a solid phase and a first tagged or labeled binding member along with one or more other untagged or unlabeled binding members is added to the solid phase. Presence of an untagged binding member that competes with the tagged binding member is observed by a decrease in the signal emitted by the tagged binding member.

For example, the present invention includes a method of identifying a c-MAF binding compound, comprising (i) immobilizing a protein to a support, (ii) contacting said immobilized protein simultaneously or in a step-wise manner with at least one tagged or labeled binding member according to the invention and one or more untagged or unlabeled test binding compounds, and (iii) identifying a new c-MAF binding compound by observing a decrease in the amount of bound tag from the tagged binding member. Such methods can be performed in a high-throughput manner using a multiwell or array format. Such assays may be also be performed in solution. See, for instance, U.S. Pat. No. 5,814,468 (Sliman et al), which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report or any other visual or physical representation of a result of the method.

Competition assays can also be used in epitope characterization. In one instance epitope characterization may be used to identify the epitope bound by a c-MAF binding member which optionally may have optimized neutralizing and/or modulating characteristics. Such an epitope can be linear or conformational. A conformational epitope can comprise at least two different domains of Maf, wherein said domains are positioned in proximity to each other when c-MAF proteins are folded in its tertiary or quaternary structure to form a conformational epitope which is recognized by an inhibitor of Maf, such as any c-MAF-binding member provided in this specification. In testing for competition a peptide fragment of the antigen may be employed, especially a peptide including or consisting of an epitope of interest. A peptide having the epitope sequence plus one or more amino acids at either end may be used. Binding members according to the present invention may be such that their binding for antigen is inhibited by a peptide with or including the sequence given.

Methods of Using Binding Members Described Herein

In some embodiments, the present invention is directed to an in vitro method for quantifying the c-MAF gene expression level in a tumor sample of a subject using a binding member (e.g., an antibody), variant, or fragment thereof described herein.

In some embodiments, the present invention is directed to an in vitro method for the diagnosis of metastasis in a subject with cancer and/or for the prognosis of the tendency to develop metastasis in a subject with cancer, said method comprising:
(i) quantifying the c-MAF gene expression level in a tumor sample of said subject using binding member (e.g., an antibody), variant, or fragment thereof described herein and
(ii) comparing the expression level obtained in (i) with the expression level of the c-MAF gene in a control sample,
wherein if the expression level of the c-MAF gene in said tumor sample is increased with respect to the expression level of the c-MAF gene in the control sample, then said subject has a positive diagnosis for metastasis or a greater tendency to develop metastasis.

In some embodiments, the present invention is directed to an in vitro method for designing a customized therapy for a subject with cancer which comprises
(i) quantifying the c-MAF gene expression level in a tumor sample of said subject using binding member (e.g., an antibody), variant, or fragment thereof of described herein, and
(ii) comparing the expression level obtained in (i) with the expression level of the c-MAF gene in a control sample,
wherein if the expression level is increased with respect to said reference value, then said subject is susceptible to receive a therapy aiming to prevent and/or treat the metastasis. If the expression level is not increased with respect to said reference value, then said subject is not susceptible to receive a therapy aiming to prevent and/or treat the metastasis. In some embodiments, the sample is a tumor derived sample, including: a tumor sample, a circulating tumor sample, circulating tumor DNA, or tumor-derived exosomes.

In some embodiments, the present invention is directed to an in vitro method for designing a customized therapy for a subject having cancer with metastasis which comprises
(i) quantifying the c-MAF gene expression level in a tumor tissue sample of said subject using a binding member (e.g., an antibody), variant, or fragment described herein, and
(ii) comparing the expression level obtained in step (i) with the expression level of the c-MAF gene in a control sample,
wherein if the c-MAF gene expression level in the tumor tissue sample is increased with respect to the expression level of the c-MAF gene in the control sample, then said subject is susceptible to receive a therapy intended to prevent or inhibit bone metastasis and degradation. If the expression level is not increased with respect to said reference value, then said subject is not susceptible to receive a therapy aiming to prevent and/or treat bone metastasis and degradation In some embodiments, the present invention is directed to an in vitro method for designing a customized therapy for a subject having cancer with metastasis which comprises
(i) quantifying the c-MAF gene expression level in a bone metastatic tumor tissue sample of said subject using a binding member (e.g., an antibody), variant, or fragment described herein, and
(ii) comparing the expression level obtained in step (i) with the expression level of the c-MAF gene in a control sample,
wherein if the c-MAF gene expression level in the tumor tissue sample is increased with respect to the expression level of the c-MAF gene in the control sample, then said subject is susceptible to receive a therapy intended to prevent or inhibit bone degradation. If the expression level is not increased with respect to said reference value, then said subject is not susceptible to receive a therapy aiming to prevent and/or treat bone degradation.

In some embodiments, the present invention is directed to an in vitro method for typing a sample of a subject suffering from cancer, the method comprising:
a) providing a sample from said subject;
b) quantifying the expression level of c-MAF in said sample using a binding member (e.g., an antibody), variant, or fragment described herein; and,
c) typing said sample by comparing the quantified expression level of c-MAF to a predetermined reference level of c-MAF expression;
wherein said typing provides prognostic information related to the risk of bone metastasis in said subject.

In another aspect, the present invention relates to an in vitro method for determining the risk of metastasis in a subject suffering cancer, which comprises determining the expression level of the c-MAF gene in a sample of said subject using a binding member described herein.

In a preferred embodiment, the metastasis is bone metastasis. In one embodiment, an expression level of said gene above the average value plus one standard deviation is indicative of an increased risk of early bone metastasis.

In a preferred embodiment, the bone metastasis is very early bone metastasis.

In a preferred embodiment, the bone metastasis is osteolytic metastasis.

"Early bone metastasis" as used herein, relates to a bone metastasis that appears before 5 years post surgery in a patient with breast cancer.

"Very early bone metastasis" as used herein, relates to a bone metastasis that appears before 3 years post surgery in a patient with breast cancer.

In some embodiments, the present invention is directed to a method for preventing, inhibiting or reducing the risk of metastasis in a subject suffering from cancer, said method comprising administering to said subject a binding member (e.g., an antibody), variant, or fragment thereof described herein. In some embodiments, the metastasis is bone metastasis.

In some embodiments, the cancer is selected from a group consisting of: breast cancer, lung cancer, prostate cancer, and renal cell carcinoma. In some embodiments, the breast cancer is selected from: HER2+ breast cancer, ER+ breast cancer, and triple negative breast cancer.

Accordingly, the present invention provides a method of treating or diagnosis of a c-MAF related disorder. In some embodiments, the invention provides a method of treatment of a c-MAF related disorder comprising administering to a patient in need thereof an effective amount of one or more binding members (e.g., antibodies) of the present invention alone or in a combined therapeutic regimen with another appropriate medicament known in the art or described herein.

As is known in the state of the art, the treatment to be administered to a subject suffering from cancer depends on whether the latter is a malignant tumor, i.e., whether it has high probabilities of undergoing metastasis, or whether the latter is a benign tumor. In the first assumption, the treatment of choice is a systemic treatment such as chemotherapy and in the second assumption, the treatment of choice is a localized treatment such as radiotherapy.

Therefore, as described in the present invention, given that c-MAF gene overexpression in cancer cells is related to the presence of metastasis (e.g., bone metastasis), the expression level of the c-MAF gene is useful for making decisions in terms of the most suitable therapy for the subject suffering said cancer.

In a particular embodiment, the metastasis is bone metastasis. In some embodiments, the bone metastasis is osteolytic metastasis.

In one embodiment, the present invention comprises in a first step quantifying the c-MAF gene expression level in a sample in a subject suffering from cancer. In a preferred embodiment, the sample is a tumor tissue sample.

In another particular embodiment, the method comprises quantifying only the c-MAF gene expression level as a single marker, i.e., the method does not involve determining the expression level of any additional marker.

In a particular embodiment, the sample can be a primary tumor tissue sample of the subject.

In one embodiment, the c-MAF gene expression level obtained in the tumor sample of the subject is compared with a reference value. In a preferred embodiment, the reference value is the c-MAF gene expression level of said gene in a control sample. The determination of the c-MAF gene expression level must be related to values of a control sample or reference sample. Depending on the type of tumor to be analyzed, the exact nature of the control sample may vary. Thus preferably the reference sample is a sample of a subject with cancer, that has not metastasized or that corresponds to the median value of the c-MAF gene expression level measured in a tumor tissue collection in biopsy samples of subjects with cancer, which has not metastasized.

Once the c-MAF gene expression level in the sample has been measured, using a binding member disclosed herein, and compared with the reference value, if the expression level of said gene is increased with respect to the reference value, then it can be concluded that said subject is susceptible to receiving therapy or not receiving therapy aiming to prevent (if the subject has yet to undergo metastasis) and/or treat metastasis or not prevent and/or treat metastasis (if the subject has already experienced metastasis).

When the primary cancer with or without metastasis is detected or has metastasized, systemic treatments including but not limited to chemotherapy, hormone treatment, immunotherapy, or a combination thereof can be used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body and could represent therapies therapy aiming to prevent or inhibit (if the subject has yet to undergo metastasis) and/or treat metastasis (if the subject has already experienced metastasis), such as:

Chemotherapy is the use of medicaments to destroy cancer cells. The medicaments are generally administered through oral or intravenous route. Sometimes, chemotherapy is used together with radiation treatment. Suitable chemotherapeutic treatments for breast cancer include, without limitation, anthracyclines (doxorubicin, epirubicin, pegylated liposomal doxorubicin), Taxanes (paclitaxel, docetaxel, albumin nano-particle bound paclitaxel), 5-fluorouracil (continuous infusion 5-FU, capecitabine), Vinca alkaloids (vinorelbine, vinblastine), Gemcitabine, Platinum salts (cisplatin, carboplatin), cyclophosphamide, Etoposide and combinations of one or more of the above such as Cyclophosphamide/anthracycline+/−5-fluorouracil regimens (such as doxorubicin/cyclophosphamide (AC), epirubicin/cyclophosphamide, (EC) cyclophosphamide/epirubicin/5-fluorouracil (CEF), cyclophosphamide/doxorubicin/5-fluorouracil (CAF), 5-fluorouracil/epirubicin/cyclophosphamide (FEC)), cyclophosphamide/metothrexate/5-fluorouracil (CMF), anthracyclines/taxanes (such as doxorubicin/paclitaxel or doxorubicin/docetaxel), Docetaxel/capecitabine, Gemcitabine/paclitaxel, Taxane/platinum regimens (such as paclitaxel/carboplatin or docetaxel/carboplatin).

Immunotherapy is a treatment that aids the immune system itself of the patient to combat cancer. There are several types of immunotherapy which are used to treat metastasis in patients. These include but are not limited to cytokines, monoclonal antibodies and antitumor vaccines.

In another aspect, the treatment is Alpharadin (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer. Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

In another aspect, the treatment is an mTor inhibitor. In some aspects, the mTor inhibitor is a dual mTor/PI3kinase inhibitor. In some aspects, the mTor inhibitor is used to prevent or inhibit metastasis. In some aspects the mTor inhibitor is selected from the group consisting of: ABI009 (sirolimus), rapamycin (sirolimus), Abraxane (paclitaxel), Absorb (everolimus), Afinitor (everolimus), Afinitor with Gleevec, AS703026 (pimasertib), Axxess (umirolimus), AZD2014, BEZ235, Biofreedom (umirolimus), BioMatrix (umirolimus), BioMatrix flex (umirolimus), CC115, CC223, Combo Bio-engineered Sirolimus Eluting Stent ORBUS-NEICH (sirolimus), Curaxin CBLC102 (mepacrine), DE109 (sirolimus), DS3078, Endeavor DES (zotarolimus), Endeavor Resolute (zotarolimus), Femara (letrozole), Hocena (antroquinonol), INK128, Inspiron (sirolimus), IPI504 (retaspimycin hydrochloride), KRN951 (tivozanib), ME344, MGA031 (teplizumab), MiStent SES (sirolimus), MKC1, Nobori (umirolimus), OSI027, OVI123 (cordycepin), Palomid 529, PF04691502, Promus Element (everolimus), PWT33597, Rapamune (sirolimus), Resolute DES (zotarolimus), RG7422, SAR245409, SF1126, SGN75 (vorsetuzumab mafodotin), Synergy (everolimus), Taltorvic (ridaforolimus), Tarceva (erlotinib), Torisel (temsirolimus), Xience Prime (everolimus), Xience V (everolimus), Zomaxx (zotarolimus), Zortress (everolimus), Zotarolimus Eluting Peripheral Stent MEDTRONIC (zotarolimus), AP23841, AP24170, ARmTOR26, BN107, BN108, Canstatin GENZYME (canstatin), CU906, EC0371, EC0565, KI1004, LOR220, NV128, Rapamycin ONCOIMMUNE (sirolimus), SB2602, Sirolimus PNP SAMYANG BIOPHARMACEUTICALS (sirolimus), TOP216, VLI27, VS5584, WYE125132, XL388, Advacan (everolimus), AZD8055, Cypher Select Plus Sirolimus eluting Coronary Stent (sirolimus), Cypher Sirolimus eluting coronary stent (sirolimus), Drug Coated Balloon (sirolimus), E-Magic Plus (sirolimus), Emtor (sirolimus), Esprit (everolimus), Evertor (everolimus), HBF0079, LCP-Siro (sirolimus), Limus CLARIS (sirolimus), mTOR Inhibitor CELLZOME, Nevo Sirolimus eluting Coronary Stent (sirolimus), nPT-mTOR, Rapacan (sirolimus), Renacept (sirolimus), ReZolve (sirolimus), Rocas (sirolimus), SF1126, Sirolim (sirolimus), Sirolimus NORTH CHINA (sirolimus), Sirolimus RANBAXY (sirolimus), Sirolimus WATSON (sirolimus) Siropan (sirolimus), Sirova (sirolimus), Supralimus (sirolimus), Supralimus-Core (sirolimus), Tacrolimus WATSON (tacrolimus), TAFA93, Temsirolimus ACCORD (temsirolimus), Temsirolimus SANDOZ (temsirolimus), TOP216, Xience Prime (everolimus), Xience V (everolimus). In a specific aspect the mTor inhibitor is Afinitor (everolimus) (http://www.afinitor.com/index.jsp?usertrack.filter_applied= true&NovaId=4029462064338207963; last accessed Nov. 28, 2012). In another aspect, everolimus is combined with an aromatase inhibitor. (See. e.g., Baselga, J., el al., Everolimus in Postmenopausal Hormone-Receptor Positive Advanced Breast Cancer. 2012. *N. Engl. J. Med.* 366(6): 520-529, which is herein incorporated by reference). In another aspect, mTor inhibitors can be identified through methods known in the art. (See, e.g., Zhou, H. et al. Updates of mTor inhibitors. 2010. *Anticancer Agents Med. Chem.* 10(7): 571-81, which is herein incorporated by reference). In some aspects, the mTor inhibitor is used to treat or prevent or inhibit metastasis in a patient that is positive for a hormone receptor. (See. e.g., Baselga, J., el al., Everolimus in Postmenopausal Hormone-Receptor Positive Advanced Breast Cancer. 2012. *N. Engl. J. Med.* 366(6): 520-529). In some embodiments, the patient is ER+. In some aspects, the mTor inhibitor is used to treat or prevent or inhibit metastasis in a patient with advanced breast cancer. In some aspects, the mTor inhibitor is used in combination with a second treatment. In some aspects, the second treatment is any treatment described herein.

In another aspect, the treatment is a Src kinase inhibitor. In some aspects, the Src inhibitor is used to prevent or inhibit metastasis. In some aspects, the Src kinase inhibitor is selected from the group: AZD0530 (saracatinib), Bosulif (bosutinib), ENMD981693, KD020, KX01, Sprycel (dasatinib), Yervoy (ipilimumab), AP23464, AP23485, AP23588, AZD0424, c-Src Kinase Inhibitor KISSEI, CU201, KX2361, SKS927, SRN004, SUNK706, TG100435, TG100948, AP23451, Dasatinib HETERO (dasatinib), Dasatinib VALEANT (dasatinib), Fontrax (dasatinib), Src Kinase Inhibitor KINEX, VX680, (tozasertib lactate), XL228, and SUNK706. In some embodiments, the Src kinase inhibitor is dasatinib. In another aspect, Src kinase inhibitors can be identified through methods known in the art (See, e.g., Sen, B. and Johnson, F. M. Regulation of Src Family Kinases in Human Cancers. 2011. *J. Signal Transduction.* 2011: 14 pages, which is herein incorporated by reference). In some aspects, the Src kinase inhibitor is used to treat or prevent or inhibit metastasis in a patient that is positive for the SRC-responsive signature (SRS). In some aspects, the patient is SRS+ and ER−. (See. e.g., Zhang, CH.-F, et al. Latent Bone Metastasis in Breast Cancer Tied to Src-Dependent survival signals. 2009. *Cancer Cell.* 16: 67-78, which is herein incorporated by reference.) In some aspects, the Src kinase inhibitor is used to treat or prevent or inhibit metastasis in a patient with advanced breast cancer. In some aspects, the Src kinase inhibitor is used in combination with a second treatment. In some aspects, the second treatment is any treatment described herein.

In another aspect, the treatment is a COX-2 inhibitor. In some aspects, the COX-2 inhibitor is used to prevent or inhibit metastasis. In some aspects, the COX-2 inhibitor is selected from the group: ABT963, Acetaminophen ER JOHNSON (acetaminophen), Acular X (ketorolac tromethamine), BAY1019036 (aspirin), BAY987111 (diphenhydramine, naproxen sodium), BAY11902 (piroxicam), BCIBUCH001 (ibuprofen), Capoxigem (apricoxib), CS502, CS670 (pelubiprofen), Diclofenac HPBCD (diclofenac), Diractin (ketoprofen), GW406381, HCT1026 (nitroflurbiprofen), Hyanalgese-D (diclofenac), HydrocoDex (acetaminophen, dextromethorphan, hydrocodone), Ibuprofen Sodium PFIZER (ibuprofen sodium), Ibuprofen with Acetaminophen PFIZER (acetaminophen, ibuprofen), Impracor (ketoprofen), IP880 (diclofenac), IP940 (indomethacin), ISV205 (diclofenac sodium), JNS013 (acetaminophen, tramadol hydrochloride), Ketoprofen TDS (ketoprofen), LTNS001 (naproxen etemesil), Mesalamine SALIX (mesalamine), Mesalamine SOFAR (mesalamine), Mesalazine (mesalamine), ML3000 (licofelone), MRX7EAT (etodolac), Naproxen IROKO (naproxen), NCX4016 (nitroaspirin), NCX701 (nitroacetaminophen), Nuprin SCOLR (ibuprofen), OMS103HP (amitriptyline hydrochloride, ketoprofen, oxymetazoline hydrochloride), Oralease (diclofenac), OxycoDex (dextromethorphan, oxycodone), P54, PercoDex (acetaminophen, dextromethorphan, oxycodone), PL3100 (naproxen, phosphatidyl choline), PSD508, R-Ketoprofen (ketoprofen), Remura (bromfenac sodium), ROX828 (ketorolac tromethamine), RP19583 (ketoprofen lysine), RQ00317076, SDX101 (R-etodolac), TDS943 (diclofenac sodium), TDT070 (ketoprofen), TPR100, TQ1011 (ketoprofen), TT063 (S-flurbiprofen), UR8880 (cimicoxib), V0498TA01A (ibuprofen), VT122 (etodolac, propranolol), XP20B (acetaminophen, dextropropoxyphene), XP21B (diclofenac potassium), XP21L (diclofenac potassium), Zoenasa (acetylcysteine, mesalamine), Acephen, Actifed Plus, Actifed-P, Acular, Acular LS, Acular PF, Acular X, Acuvail, Advil, Advil Allergy Sinus, Advil Cold and Sinus, Advil Congestion Relief, Advil PM, Advil PM Capsule, Air Salonpas, Airtal, Alcohol-Free NyQuil Cold & Flu Relief, Aleve, Aleve ABDI IBRAHIM, Aleve-D, Alka-Seltzer, Alka-Seltzer BAYER, Alka-Seltzer Extra Strength, Alka-Seltzer Lemon-Lime, Alka-Seltzer Original, Alka-Seltzer Plus, Alka-Seltzer plus Cold and Cough, Alka-Seltzer plus Cold and Cough Formula, Alka-Seltzer Plus Day and Night Cold Formula, Alka-Seltzer Plus Day Non-Drowsy Cold Formula, Alka-Seltzer Plus Flu Formula, Alka-Seltzer Plus Night Cold Formula, Alka-Seltzer Plus Sinus Formula, Alka-Seltzer Plus Sparkling Original Cold Formula, Alka-Seltzer PM, Alka-Seltzer Wake-Up Call, Anacin, Anaprox, Anaprox MINERVA, Ansaid, Apitoxin, Apranax, Apranax abdi, Arcoxia, Arthritis Formula Bengay, Arthrotec, Asacol, Asacol HD, Asacol MEDUNA ARZNEIMITTEL, Asacol ORIFARM, Aspirin BAYER, Aspirin Complex, Aspirin Migran, AZD3582, Azulfidine, Baralgan M, BAY1019036, BAY987111, BAY11902, BCIBUCH001, Benadryl Allergy, Benadryl Day and Night, Benylin 4 Flu, Benylin Cold and Flu, Benylin Cold and Flu Day and Night, Benylin Cold and Sinus Day and Night, Benylin Cold and Sinus Plus, Benylin Day and Night Cold and Flu Relief, Benylinl All-In-One, Brexin, Brexin ANGELINI, Bromday, Bufferin, Buscopan Plus, Caldolor, Calmatel, Cambia, Canasa, Capoxigem, Cataflam, Celebrex, Celebrex ORIFARM, Children's Advil Allergy Sinus, Children's Tylenol, Children's Tylenol Cough and Runny Nose, Children's Tylenol plus cold, Children's Tylenol plus Cold and Cough, Children's Tylenol plus cold and stuffy nose, Children's Tylenol plus Flu, Children's Tylenol plus cold & allergy, Children's Tylenol plus Cough & Runny Nose, Children's Tylenol plus Cough & Sore Throat, Children's Tylenol plus multi symptom cold, Clinoril, Codral Cold and Flu, Codral Day and Night Day Tablets, Codral Day and Night Night Tablets, Codral Nightime, Colazal, Combunox, Contac Cold plus Flu, Contac Cold plus Flu Non-Drowsy, Coricidin D, Coricidin HBP Cold and Flu, Coricidin HBP Day and Night Multi-Symptom Cold, Coricidin HBP Maximum Strength Flu, Coricidin HBP Nighttime Multi-Symptom Cold, Coricidin II Extra Strength Cold and Flu, CS502, CS670, Daypro, Daypro Alta, DDS06C, Demazin Cold and Flu, Demazin Cough, Cold and Flu, Demazin day/night Cold and Flu, Demazin PE Cold and Flu, Demazin PE day/night Cold and Flu, Diclofenac HPBCD, Dimetapp Day Relief, Dimetapp Multi-Symptom Cold and Flu, Dimetapp Night Relief, Dimetapp Pain and Fever Relief, Dimetapp PE Sinus Pain, Dimetapp PE Sinus Pain plus Allergy, Dipentum, Diractin, Disprin Cold 'n' Fever, Disprin Extra, Disprin Forte. Disprin Plus, Dristan Cold, Dristan Junior, Drixoral Plus, Duexis, Dynastat, Efferalgan, Efferalgan Plus Vitamin C, Efferalgan Vitamin C, Elixsure IB, Excedrin Back and Body, Excedrin Migraine, Excedrin PM, Excedrin Sinus Headache, Excedrin Tension Headache, Falcol, Fansamac, Feldene, Fever-All, Fiorinal, Fiorinal with Codeine, Flanax, Flector Patch, Flucam, Fortagesic, Gerbin, Giazo, Gladio, Goody's Back and Body Pain, Goody's Cool Orange, Goody's Extra Strength, Goody's PM, Greaseless Bengay, GW406381, HCT1026, He Xing Yi, Hyanalgese-D, HydrocoDex, Ibuprofen Sodium PFIZER, Ibuprofen with, Acetaminophen PFIZER, Icy Hot SANOFI AVENTIS, Impracor, Indocin, Indomethacin APP PHARMA, Indomethacin MYLAN, Infants' Tylenol, IP880, IP940, Iremod, ISV205, JNS013, Jr. Tylenol, Junifen, Junior Strength Advil, Junior Strength Motrin, Ketoprofen TDS, Lemsip Max, Lemsip Max All in One, Lemsip Max All Night, Lemsip Max Cold and Flu, Lialda, Listerine Mouth Wash, Lloyds Cream, Lodine, Lorfit P, Loxonin, LTNS001, Mersyndol, Mesalamine SALIX, Mesalamine SOFAR, Mesalazine, Mesasal GLAXO, Mesasal SANOFI, Mesulid, Metsal Heat Rub, Midol Complete, Midol Extended Relief, Midol Liquid Gels, Midol PM, Midol Teen Formula, Migranin COATED TABLETS, ML3000, Mobic, Mohrus, Motrin, Motrin Cold and Sinus Pain, Motrin PM, Movalis ASPEN, MRX7EAT, Nalfon, Nalfon PEDINOL, Naprelan, Naprosyn, Naprosyn RPG LIFE SCIENCE, Naproxen IROKO, NCX4016, NCX701, NeoProfen LUNDBECK, Nevanac, Nexcede, Niflan, Norgesic MEDICIS, Novalgin, Nuprin SCOLR, Nurofen, Nurofen Cold and Flu, Nurofen Max Strength Migraine, Nurofen Plus, Nuromol, NyQuil with Vitamin C, Ocufen, OMS103HP, Oralease, Orudis ABBOTT JAPAN, Oruvail, Osteluc, OxycoDex, P54, Panadol, Panadol Actifast, Paradine, Paramax, Parfenac, Pedea, Pennsaid, Pentasa, Pentasa ORIFARM, Peon, Percodan, Percodan-Demi, PercoDex, Percogesic, Perfalgan, PL2200, PL3100, Ponstel, Prexige, Prolensa, PSD508, R-Ketoprofen, Rantudil, Relafen, Remura, Robaxisal, Rotec, Rowasa, ROX828, RP19583, RQ00317076, Rubor, Salofalk, Salonpas, Saridon, SDX101, Seltouch, sfRowasa, Shinbaro, Sinumax, Sinutab, Sinutab, sinus, Spalt, Sprix, Strefen, Sudafed Cold and Cough, Sudafed Head Cold and Sinus, Sudafed PE Cold plus Cough, Sudafed PE Pressure plus Pain, Sudafed PE, Severe Cold, Sudafed PE Sinus Day plus Night Relief Day Tablets, Sudafed PE Sinus Day plus Night Relief Night Tablets, Sudafed PE Sinus plus Anti-inflammatory Pain Relief, Sudafed Sinus Advance, Surgam, Synalgos-DC, Synflex, Tavist allergy/sinus/headache, TDS943, TDT070, Theraflu Cold and Sore Throat, Theraflu Daytime Severe Cold and Cough, Theraflu Daytime Warming Relief,Theraflu Warming Relief Caplets Daytime Multi-Symptom Cold, Theraflu Warming Relief Cold and Chest Congestion, Thomapyrin, Thomapyrin C, Thomapyrin Effervescent, Thomapyrin Medium, Tilcotil, Tispol, Tolectin, Toradol, TPR100, TQ1011, Trauma-Salbe, Trauma-Salbe Kwizda, Treo, Treximet, Trovex, TT063, Tylenol, Tylenol Allergy Multi-Symptom, Tylenol Back Pain, Tylenol Cold & Cough Daytime, Tylenol Cold & Cough Nighttime, Tylenol Cold and Sinus Daytime, Tylenol Cold and Sinus Nighttime, Tylenol Cold Head Congestion Severe, Tylenol Cold Multi Symptom Daytime, Tylenol Cold Multi Symptom Nighttime Liquid, Tylenol Cold Multi Symptom Severe, Tylenol Cold Non-Drowsiness Formula, Tylenol Cold Severe Congestion Daytime, Tylenol Complete Cold, Cough and Flu Night time, Tylenol Flu Nighttime, Tylenol Menstrual, Tylenol PM, Tylenol Sinus Congestion & Pain Daytime, Tylenol Sinus Congestion & Pain Nighttime, Tylenol Sinus Congestion & Pain Severe, Tylenol Sinus Severe Congestion Daytime, Tylenol Ultra Relief, Tylenol with Caffeine and Codeine phosphate, Tylenol with Codeine phosphate, Ultra Strength Bengay Cream, Ultracet, UR8880, V0498TA01A, Vicks NyQuil Cold and Flu Relief, Vicoprofen, Vimovo, Voltaren Emulgel, Voltaren GEL, Voltaren NOVARTIS CONSUMER HEALTH GMBH, Voltaren XR, VT122, Xefo, Xefo Rapid, Xefocam, Xibrom, XL3, Xodol, XP20B, XP21B, XP21L, Zipsor, and Zoenasa. In another aspect, COX-2 inhibitors can be identified through methods known in the art (See, e.g., Dannhardt, G. and Kiefer, W. Cyclooxygenase inhibitors—current status and future prospects. 2001. *Eur. J. Med. Chem.* 36: 109-126, which is herein incorporated by reference). In some aspects, the COX-2 inhibitor is used to treat or prevent or inhibit metastasis in a patient with advanced breast cancer. In some aspects, the COX-2 inhibitor is used in combination with a second treatment. In some aspects, the second treatment is any treatment described herein. In some aspects, the COX-2 inhibitor is used in combination with a second treatment selected from the group consisting of: Denosumab, Zometa (http://www.us.zometa.com/index.jsp?usertrack.filter_applied=true&NovaId=2935376934467633633; last accessed Dec. 2, 2012), Carbozantinib or Cabozantinib, Antibody or peptide blocking PTHLH (parathyroid hormone like hormone) or PTHrP (parathyroid hormone related protein) and Everolimus.

In another aspect, the treatment agents used for avoiding and/or preventing bone degradation include, but are not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.

"DKK-1(Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., American Association for Cancer Research Annual Meeting. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (i.e., blastic lesions) or destruction (i.e., lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl)piperidin-1-yl]carbonylaminopyridin-4-yl}oxy)phenyl]-N'-(4-fluorophenyl) cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495). Antibodies suitable in the context of the present invention include intact antibodies which comprise a variable antigen binding region and a constant region, fragments "Fab", "F(ab')2" and "Fab'", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223 calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary breast cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. et al. 2012. CCR5 Antagonist Blocks Metastasis of Basal Breast Cancer Cells. *Cancer Research*. 72:3839-3850.). In some embodiments, the CCR5 antagonist is Vicriviroc. Velasco-Veláquez, M. et al. 2012. CCR5 Antagonist Blocks Metastasis of Basal Breast Cancer Cells. *Cancer Research*. 72:3839-3850.). In some aspects, the CCR5 antagonist is Aplaviroc (Demarest J. F. et al. 2005. Update on Aplaviroc: An HIV Entry Inhibitor Targeting CCR5. *Retrovirology* 2(Suppl. 1): S13). In some aspects, the CCR5 antagonist is a spiropiperidine CCR5 antagonist. (Rotstein D. M. et al. 2009. Spiropiperidine CCR5 antagonists. *Bioorganic & Medicinal Chemistry Letters*. 19 (18): 5401-5406. In some embodiments, the CCR5 antagonist is INCB009471 (Kuritzkes, D. R. 2009. HIV-1 entry inhibitors: an overview. *Curr. Opin. HIV AIDS*. 4(2): 82-7).

In a preferred embodiment the dual MET and VEGFR2 inhibitor is selected from the group consisting of Cabozantinib, Foretinib and E7050.

In a preferred embodiment the Radium 223 therapy is alpharadin.

Alternatively a combined treatment can be carried out in which more than one agent from those mentioned above are combined to treat and/or prevent the metastasis or said agents can be combined with other supplements, such as calcium or vitamin D or with a hormone treatment.

Once the c-MAF gene expression level in the sample is measured and compared with the reference value (e.g., the c-MAF gene expression level of a control sample), if the expression level of said gene is increased with respect to the reference value, then this is indicative that said subject is susceptible to receive a therapy aiming to avoid or prevent bone degradation.

Illustrative examples of agents used for avoiding and/or preventing bone degradation include, although not limited to:

Parathyroid hormone (PTH) and Parathyroid like hormone (PTHLH) inhibitors (including blocking antibodies) or recombinant forms thereof (teriparatide corresponding to the amino acids 7-34 of PTH). This hormone acts by stimulating the osteoclasts and increasing their activity.

Strontium ranelate: is an alternative oral treatment, and forms part of the group of drugs called "dual action bone agents" (DABAs) because they stimulate the osteoblast proliferation and inhibit the osteoclast proliferation.

"Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which can be used in the therapy designed by means of the fifth method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

Alpharadin (radium-223 dichloride). Alpharadin uses alpha radiation from radium-223 decay to kill cancer cells. Radium-223 naturally self-targets to bone metastases by virtue of its properties as a calcium-mimic. Alpha radiation has a very short range of 2-10 cells (when compared to current radiation therapy which is based on beta or gamma radiation), and therefore causes less damage to surrounding healthy tissues (particularly bone marrow). With similar properties to calcium, radium-223 is drawn to places where calcium is used to build bone in the body, including the site of faster, abnormal bone growth—such as that seen in the skeletal metastases of men with advanced, castration-resistant prostate cancer.

Radium-223, after injection, is carried in the bloodstream to sites of abnormal bone growth. The place where a cancer starts in the body is known as the primary tumor. Some of these cells may break away and be carried in the bloodstream to another part of the body. The cancer cells may then settle in that part of the body and form a new tumor. If this happens it is called a secondary cancer or a metastasis. Most patients with late stage prostate cancer suffer the maximum burden of disease in their bones. The aim with radium-223 is to selectively target this secondary cancer. Any radium-223 not taken-up in the bones is quickly routed to the gut and excreted.

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 01/49288 of Merck Frosst Canada & Co. and Axys Pharmaceuticals.

"DKK-1(Dickkopf-1) inhibitor" as used herein refers to any compound which is capable of reducing DKK-1 activity. DKK-1 is a soluble Wnt pathway antagonist expressed predominantly in adult bone and upregulated in myeloma patients with osteolytic lesions. Agents targeting DKK-1 may play a role in preventing osteolytic bone disease in multiple myeloma patients. BHQ880 from Novartis is a first-in-class, fully human, anti-DKK-1 neutralizing antibody. Preclinical studies support the hypothesis that BHQ880 promotes bone formation and thereby inhibits tumor-induced osteolytic disease (Ettenberg S. et al., *American Association for Cancer Research Annual Meeting*. Apr. 12-16, 2008; San Diego, Calif. Abstract).

"Dual MET and VEGFR2 inhibitor" as used herein refers to any compound which is a potent dual inhibitor of the MET and VEGF pathways designed to block MET driven tumor escape. MET is expressed not only in tumor cells and endothelial cells, but also in osteoblasts (bone-forming cells) and osteoclasts (bone-removing cells). HGF binds to MET on all of these cell types, giving the MET pathway an important role in multiple autocrine and paracrine loops. Activation of MET in tumor cells appears to be important in the establishment of metastatic bone lesions. At the same time, activation of the MET pathway in osteoblasts and osteoclasts may lead to pathological features of bone metastases, including abnormal bone growth (i.e., blastic lesions) or destruction (i.e., lytic lesion. Thus, targeting the MET pathway may be a viable strategy in preventing the establishment and progression of metastatic bone lesions. Cabozantinib (Exelixis, Inc), formerly known as XL184 (CAS 849217-68-1), is a potent dual inhibitor of the MET and VEGF pathways designed to block MET driven tumor escape. In multiple preclinical studies cabozantinib has been shown to kill tumor cells, reduce metastases, and inhibit angiogenesis (the formation of new blood vessels necessary to support tumor growth). Another suitable dual inhibitors are E7050 (N-[2-Fluoro-4-({2-[4-(4-methylpiperazin-1-yl)piperidin-1-yl]carbonylaminopyridin-4-yl} oxy) phenyl]-N'-(4-fluorophenyl) cyclopropane-1,1-dicarboxamide (2R,3R)-tartrate) (CAS 928037-13-2) or Foretinib (also known as GSK1363089, XL880, CAS 849217-64-7).

"RANKL inhibitors" as used herein refer to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:

a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.

Osteoprotegerin or a variant thereof with RANKL-binding capacity.

RANKL-specific antisense molecules

Ribozymes capable of processing the transcribed products of RANKL

Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al., (1975) *Nature,* 256: 495). Antibodies suitable in the context of the present invention include intact antibodies which comprise a variable antigen binding region and a constant region, fragments "Fab", "F(ab')2" and "Fab'", Fv, scFv, diabodies and bispecific antibodies.

Specific anti-RANKL nanobodies. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. The general structure of nanobodies is FR1-CDR1-FR2-CDR2-FR3-CDR3-FR4 wherein FR1 to FR4 are the framework regions 1 to 4 CDR1 to CDR3 are the complementarity determining regions 1 to 3. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. These newly discovered VHH domains with their unique structural and functional properties form the basis of a new generation of therapeutic antibodies which Ablynx has named Nanobodies.

In one embodiment, the RANKL inhibitor is selected from the group consisting of a RANKL specific antibody, a RANKL specific nanobody and osteoprotegerin. In a specific embodiment, the anti-RANKL antibody is a monoclonal antibody. In a yet more specific embodiment, the anti-RANKL antibody is Denosumab (Pageau, Steven C. (2009) *mAbs* 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). Various aspects of Denosumab are covered by U.S. Pat. Nos. 6,740,522; 7,411,050; 7,097,834; 7,364,736 (the entire contents of each of which are hereby incorporated by reference in their entirety). In another embodiment, the RANKL inhibitor an antibody, antibody fragment, or fusion construct that binds the same epitope as Denosumab.

In a preferred embodiment, the anti-RANKL nanobody is any of the nanobodies as described in WO2008142164, (the contents of which are incorporated in the present application by reference). In a still more preferred embodiment, the anti-RANKL antibody is the ALX-0141 (Ablynx). ALX-0141 has been designed to inhibit bone loss associated with post-menopausal osteoporosis, rheumatoid arthritis, cancer and certain medications, and to restore the balance of healthy bone metabolism.

In a preferred embodiment, the agent preventing the bone degradation is selected from the group consisting of a bisphosphonate, a RANKL inhibitor, PTH and PTHLH inhibitor or a PRG analog, strontium ranelate, a DKK-1 inhibitor, a dual MET and VEGFR2 inhibitor, an estrogen receptor modulator, Radium-223, calcitonin, and a cathepsin K inhibitor. In a more preferred embodiment the agent preventing the bone degradation is a bisphosphonate. In a yet more preferred embodiment, the bisphosphonate is the zoledronic acid.

In one embodiment, a CCR5 antagonist is administered to prevent or inhibit metastasis of the primary breast cancer tumor to bone. In one embodiment, the CCR5 antagonist is a large molecule. In another embodiment, the CCR5 antagonist is a small molecule. In some embodiments, the CCR5 antagonist is Maraviroc (Velasco-Veláquez, M. et al. (2012). CCR5 Antagonist Blocks Metastasis of Basal Breast Cancer Cells. *Cancer Research.* 72:3839-3850.). In some embodiments, the CCR5 antagonist is Vicriviroc. Velasco-Veláquez, M. et al. (2012). CCR5 Antagonist Blocks Metastasis of Basal Breast Cancer Cells. *Cancer Research.* 72:3839-3850.). In some aspects, the CCR5 antagonist is Aplaviroc (Demarest J. F. et al. 2005. Update on Aplaviroc: An HIV Entry Inhibitor Targeting CCR5. *Retrovirology* 2(Suppl. 1): S13). In some aspects, the CCR5 antagonist is a spiropiperidine CCR5 antagonist. (Rotstein D. M. et al. (2009). Spiropiperidine CCR5 antagonists. *Bioorganic & Medicinal Chemistry Letters.* 19 (18): 5401-5406. In some embodiments, the CCR5 antagonist is INCB009471 (Kuritzkes, D. R. (2009). HIV-1 entry inhibitors: an overview. *Curr. Opin. HIV AIDS.* 4(2): 82-7).

In a preferred embodiment the dual MET and VEGFR2 inhibitor is selected from the group consisting of Cabozantinib, Foretinib and E7050.

In a preferred embodiment the Radium 223 therapy is alpharadin.

An additional aspect of the invention relates to the use of isolated "antisense" nucleic acids to inhibit expression, for example, for inhibiting transcription and/or translation of a nucleic acid which encodes c-MAF the activity of which is to be inhibited. The antisense nucleic acids can be bound to the potential target of the drug by means of conventional base complementarity or, for example, in the case of binding to Double stranded DNA through specific interaction in the large groove of the double helix. Generally, these methods refer to a range of techniques generally used in the art and they include any method which is based on the specific binding to oligonucleotide sequences.

Small interfering RNA or siRNA are agents which are capable of inhibiting the expression of a target gene by means of RNA interference. A siRNA can be chemically synthesized, can be obtained by means of in vitro transcription or can be synthesized in vivo in the target cell. Typically, the siRNA consist of a double stranded RNA between 15 and 40 nucleotide long and may contain a 3' and/or 5' protruding region of 1 to 6 nucleotides. The length of the protruding region is independent of the total length of the siRNA molecule. The siRNA acts by means of degrading or silencing the target messenger after transcription.

The siRNA of the invention are substantially homologous to the mRNA of the c-MAF encoding gene or to the gene sequence which encodes said protein. "Substantially homologous" is understood as having a sequence which is sufficiently complementary or similar to the target mRNA such that the siRNA is capable of degrading the latter through RNA interference. The siRNA suitable for causing said interference include siRNA formed by RNA, as well as siRNA containing different chemical modifications such as:
- siRNA in which the bonds between the nucleotides are different than those that appear in nature, such as phosphorothionate bonds.
- Conjugates of the RNA strand with a functional reagent, such as a fluorophore.
- Modifications of the ends of the RNA strands, particularly of the 3' end by means of the modification with different hydroxyl functional groups in 2' position.
- Nucleotides with modified sugars such as O-alkylated residues on 2' position like 2'-O-methylribose or 2'-O-fluororibose.
- Nucleotides with modified bases such as halogenated bases (for example 5-bromouracil and 5-iodouracil), alkylated bases (for example 7-methylguanosine).

On the other hand, the invention also contemplates the use of DNA enzymes to inhibit the expression of the c-MAF gene of the invention. DNA enzymes incorporate some of the mechanistic features of both antisense and ribozyme technologies. DNA enzymes are designed such that they recognize a particular target nucleic acid sequence similar to the antisense oligonucleotide, nevertheless like the ribozyme they are catalytic and specifically cleave the target nucleic acid.

Ribozyme molecules designed for catalytically cleaving transcription products of a target mRNA to prevent the translation of the mRNA which encodes c-MAF the activity of which is to be inhibited, can also be used. Ribozymes are enzymatic RNA molecules capable of catalyzing specific RNA cleaving (For a review, see, Rossi, *Current Biology* 4: 469-471, 1994). The mechanism of ribozyme action involves a specific hybridization of a ribozyme molecule sequence to a complementary target RNA followed by an endonucleolytic cleavage event. The composition of the ribozyme molecules preferably includes one or more sequences complementary to the target mRNA and the well-known sequence responsible for cleaving the mRNA or a functionally equivalent sequence (see, for example, U.S. Pat. No. 5,093,246).

In one embodiment, the subject is treated with any c-MAF inhibitory agent, antisense oligonucleotide, siRNA, DNA enzymes, ribozymes, inhibitory antibodies, inhibitory peptides, negative c-MAF dominants, or other c-MAF inhibitory molecules disclosed in Int'l. Appl. No. PCT/IB2013/001204 and U.S. application Ser. No. 13/878,114 (triple-negative breast cancer and ER+ breast cancer), Int'l Appl. No. PCT/US2014/026154 (renal cell carcinoma), Int'l Appl. No. PCT/US2014/028722 (breast cancer), Int'l Appl. No. PCT/US2013/044584 (lung cancer), U.S. application Ser. No. 14/050,262 and Int'l Appl. No. PCT/IB2013/002866 (prostate cancer), Int'l Appl. No. PCT/US2014/059506 (HER2+ breast cancer), U.S. application Ser. No. 14/213,670 and Int'l Appl. No. PCT/US2014/028569 (metastatic cancer), each of which are incorporated here by reference in its entirety. In some embodiments, the c-MAF inhibitory agents are used to treat or prevent bone degradation.

Alternatively a combined treatment can be carried out in which more than one agent from those mentioned above are combined to treat and/or prevent the metastasis or said agents can be combined with other supplements, such as calcium or vitamin D or with a hormone treatment.

In another aspect, the invention relates to an in vitro method for predicting metastasis of a cancer, in a subject suffering said cancer which comprises determining if the c-MAF gene is amplified, using a binding member disclosed herein, in a sample of said subject relative to a reference gene copy number wherein an amplification of the c-MAF gene with respect to said reference gene copy number is indicative of increased risk of developing metastasis. In some embodiments, the amplification is in region at the 16q23 locus.

In another aspect, the invention relates to an in vitro method for predicting the clinical outcome of a patient suffering from cancer, which comprises determining if the c-MAF gene is translocated in a sample of said subject wherein a translocation of the c-MAF gene is indicative of a poor clinical outcome.

In another aspect, the invention relates to an in vitro method for predicting the clinical outcome of a patient suffering cancer, which comprises determining if the c-MAF gene is translocated in a sample of said subject wherein a translocation of the c-MAF gene is indicative of a poor clinical outcome.

In some embodiments, the translocated gene is from the region at the 16q23 locus. In some embodiments, the translocated gene is from any part of the chromosomal region between about Chr. 16—about 79,392,959 bp to 79,663,806 bp (from centromere to telomere). In some embodiments, the translocated gene is from the genomic region between about Chr. 16—about 79,392,959 bp to 79,663,806 bp, but excluding DNA repeating elements.

In another aspect, the invention relates to an in vitro method (hereinafter seventh method of the invention) for predicting the clinical outcome of a patient suffering cancer, which comprises determining if the c-MAF gene is amplified in a sample of said subject relative to a reference gene copy number wherein an amplification of the c-MAF gene with respect to said reference gene copy number is indicative of a poor clinical outcome.

One embodiment comprises, in a first step, determining if the c-MAF gene is amplified in a sample of a subject. The determination of the amplification of the c-MAF is carried out essentially as described previously. In a preferred embodiment the sample is a tumor tissue sample. In a preferred embodiment, the amplification of the c-MAF gene is determined by means of determining the amplification of the locus 16q23 or 16q22-q24. In another preferred embodiment, the amplification of the c-MAF gene is determined by means of using a c-MAF gene-specific probe or an antibody disclosed herein. In a second step, this embodiment comprises comparing said copy number with the copy number of a control or reference sample, wherein if the c-MAF copy number is greater with respect to the c-MAF copy number of a control sample, then this is indicative of a poor clinical outcome.

In a preferred embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number of the c-MAF gene is increased by at least 2- (i.e., 6 copies), 3- (i.e., 8 copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number of the c-MAF gene per cell is at least 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In some embodiment, the antibody is used in any method described in Int'l. Appl. No. PCT/IB2013/001204 and U.S. application Ser. No. 13/878,114 (triple-negative breast cancer and ER+ breast cancer), Int'l Appl. No. PCT/US2014/026154 (renal cell carcinoma), Int'l Appl. No. PCT/US2014/

028722 (breast cancer), Int'l Appl. No. PCT/US2013/044584 (lung cancer), U.S. application Ser. No. 14/050,262 and Int'l Appl. No. PCT/IB2013/002866 (prostate cancer), Int'l Appl. No. PCT/US2014/059506 (HER2+ breast cancer), U.S. application Ser. No. 14/213,670 and Int'l Appl. No. PCT/US2014/028569 (metastatic cancer), each of which are incorporated here by reference in its entirety.

Methods of Treatment

Binding members (e.g., antibodies) of the present invention may be administered in the form of a pharmaceutical composition, which may comprise at least one component in addition to the binding member. Thus, pharmaceutical compositions according to the present invention, and for use in accordance with the present invention, may comprise, in addition to active ingredient, a pharmaceutically active excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration may be in tablet, capsule, powder, liquid or semisolid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members (e.g., antibodies) of the present invention may be formulated in liquid, semi-solid or solid forms depending on the physicochemical properties of the molecule and the route of delivery. Formulations may include excipients or combinations of excipients, for example: sugars, amino acids and surfactants. Liquid formulations may include a wide range of antibody concentrations and pH. Solid formulations may be produced by lyophilization, spray drying, or drying by supercritical fluid technology, for example. Formulations of binding members will depend upon the intended route of delivery. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art (Robinson, (1978) *Sustained and Controlled Release Drug Delivery Systems*, Marcel Dekker, Inc., New York).

A composition may be administered alone or in combination with other treatments, either simultaneously or sequentially dependent upon the condition to be treated.

A binding member (e.g., antibody) of the invention may be used as part of a combination therapy in conjunction with an additional medicinal component. Combination treatments may be used to provide significant synergistic effects, particularly the combination of a binding member of the invention with one or more other antibodies. A binding member of the invention may be administered concurrently or sequentially or as a combined preparation with another therapeutic agent or agents, for the treatment of one or more of the conditions listed herein.

A binding member (e.g., antibody) of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a 'therapeutically effective amount', this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody are well known in the art (Ledermann et al., (1991) *Int. J. Cancer* 47: 659-664; Bagshawe et al., (1991) *Antibody, Immunoconjugates and Radiopharmaceuticals* 4: 915-922). Specific dosages indicated herein or in the Physician's Desk Reference (2009) as appropriate for the type of medicament being administered may be used. A therapeutically effective amount or suitable dose of a binding member (e.g., antibody) of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody or fragment) and the nature of any detectable label or other molecule attached to the antibody. A typical antibody dose will be in the range of at least about 100 µg to about 1 g for systemic applications, and at least about 1 µg to about 1 mg for topical applications. An initial higher loading dose, followed by one or more lower doses, may be administered. Typically, the antibody will be a whole antibody, e.g. the $IgG_1$ isotype. This is a dose for a single treatment of an adult patient, which may be proportionally adjusted for children, infants and neonates, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after transplantation surgery, and/or may be administered or applied directly at the anatomical site of surgical treatment.

Nucleic Acids

The present invention further provides an isolated nucleic acid encoding a binding member (e.g., antibody) of the present invention. A nucleic acid may include DNA and/or RNA. In one embodiment, the present invention provides a nucleic acid that codes for a CDR or set of CDRs or $V_H$ domain or $V_L$ domain or antibody antigen-binding site or antibody molecule, of the invention as defined above. In some embodiments, the polynucleotides encode polypeptides comprising the heavy chain CDRs at least about about 70%, about 75%, about 80%, about 85%, about 90%, about 95%, about 99% or about 100% identical SEQ ID NO: 38, 40, and 42. In some embodiments, the polynucleotides encode polypeptides comprising the heavy chain CDRs at least about 70%, about 75%, about 80%, about 85%, about 90%, about 95%, about 99% or about 100% identical SEQ ID NO: 26, 28, and 30. In some embodiments, the polynucleotide encoding the $V_H$ is at least about 70%, about 75%, about 80%, about 85%, about 90%, about 95%, about 99% or about 100% identical to SEQ ID NO: 15. In some embodiments, the polynucleotide encoding the $V_H$ is SEQ ID NO: 15. In some embodiments, the polynucleotide encoding the heavy chain is at least about 70%, about 75%, about 80%, about 85%, about 90%, about 95%, about 99% or about 100% identical to SEQ ID NO: 14. In some embodiments, the polynucleotide encoding the heavy chain is SEQ ID NO: 14. In some embodiments, the polynucleotide encoding the $V_L$ is at least about 70%, about 75%, about 80%, about 85%, about 90%, about 95%, about 99% or about 100% identical to SEQ ID NO: 20. In some embodiments, the polynucleotide encoding the $V_L$ is SEQ ID NO: 20. In some embodiments, the polynucleotide encoding the light chain is at least about 70%, about 75%, about 80%, about 85%, about 90%, about 95%, about 99% or about 100% identical to SEQ ID NO: 18. In some embodiments, the polynucleotide encoding the light chain is SEQ ID NO: 18.

In some embodiments, the invention is directed to a vector comprising a polynucleotide that encodes any antigen binding member described herein. In some embodiments, a host cell comprises the vector. The present invention also provides constructs in the form of plasmids, vectors, transcription or expression cassettes which comprise at least one polynucleotide as above.

In some embodiments, the invention is directed to a host cell comprising a polynucleotide encoding any antigen binding molecule described herein. The present invention also provides a recombinant host cell that comprises one or more constructs as above. A nucleic acid encoding any CDR or set of CDRs or $V_H$ domain or $V_L$ domain or antibody antigen-binding site or antibody molecule, itself forms an aspect of the present invention, as does a method of production of the encoded product, which method comprises expression from encoding nucleic acid. Expression may conveniently be achieved by culturing said recombinant host cell containing the nucleic acid under appropriate conditions. Following production by expression of a binding member comprising $V_H$ or $V_L$ domain as disclosed herein, the binding member may be isolated and/or purified using any suitable technique known in the art and deemed as appropriate.

A nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

In some embodiments, the invention is directed to a method of producing an antibody or fragment thereof that binds to human c-MAF comprising culturing any host cell described herein so that the nucleic acid is expressed and the antibody produced. A yet further aspect provides a method of production of a binding member comprising $V_H$ and/or $V_L$ variable domain of the present invention, the method including causing expression from encoding nucleic acid. Such a method may comprise culturing recombinant host cells under conditions for production of said antibody $V_H$ and/or $V_L$ variable domain.

A method of production may comprise a step of isolation and/or purification of the product. A method of production may comprise formulating the product into a composition including at least one additional component, such as a pharmaceutically active excipient.

Systems for cloning and expression of a polypeptide in a variety of different host cells are well known. Suitable host cells include bacteria, mammalian cells, plant cells, filamentous fungi, yeast and insect cells and transgenic plants and animals. The expression of antibodies and antibody fragments in prokaryotic cells is well established in the art. For a review, see for example Pluckthun, (1991) *BioTechnology* 9: 545-551. A common bacterial host is *E. coli*.

Expression in eukaryotic cells in culture is also available to those skilled in the art as an option for production of a binding member (Chadd & Chamow, (2001) Curr. Op. Biotech. 12: 188-194; Andersen & Krummen, (2002) Curr. Op. Biotech. 13: 117; Larrick & Thomas, (2001) Curr. Op. Biotech. 12: 411-418). Mammalian cell lines available in the art for expression of a heterologous polypeptide include Chinese hamster ovary (CHO) cells, HeLa cells, baby hamster kidney (BHK) cells, NS0 mouse melanoma cells, YB2/0 rat myeloma cells, human embryonic kidney (HEK) cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, phagemids, or viral vectors, e.g. retroviral vectors, as appropriate (Sambrook & Russell, Molecular Cloning: a Laboratory Manual: 3rd edition, 2001, Cold Spring Harbor Laboratory Press). Many known techniques and protocols for manipulation of nucleic acid, for example in preparation of nucleic acid constructs, mutagenesis, sequencing, introduction of DNA into cells and gene expression, as well as analysis of proteins, are described in detail in Ausubel et al., eds. Short Protocols in Molecular Biology: A Compendium of Methods from Current Protocols in Molecular Biology, John Wiley & Sons, 4th edition 1999.

A further aspect of the present invention provides a host cell containing nucleic acid as disclosed herein. Such a host cell may be maintained in vitro and may be propagated in tissue culture. Such a host cell may also be maintained in vivo, e.g. in order to produce binding members in ascites. In vivo presence of the host cell may allow intra-cellular expression of the binding members of the present invention as 'intrabodies' or intra-cellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus, or any combination thereof. Introducing nucleic acid in the host cell, in particular a eukaryotic cell may use a viral or a plasmid based system. The plasmid system may be maintained episomally or may be incorporated into the host cell genome or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the binding member. The purification of the expressed product may be achieved by methods known to one of skill in the art.

A nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

In some embodiments, the binding members of the present invention may therefore be used in a method of diagnosis or treatment of a disorder associated with increased c-MAF infection.

Kits of the Invention

A kit comprising a binding member (e.g., antibody) according to any aspect or embodiment of the present invention is also provided. In another aspect, the kit is for predicting metastasis of a cancer in a subject suffering from said cancer, the kit comprising: a) means for quantifying the expression level of c-MAF in a sample of said subject; and b) means for comparing the quantified level of expression of c-MAF in said sample to a reference c-MAF expression level. In some embodiments, the means used are optical density measurements to quantify c-MAF immunohistochemistry staining or histopathological scoring where – stands for non positive tumors and +, ++, +++ stands for different levels of positivity.

In some embodiments, the immunohistochemistry staining is tissue microarray immunohistochemistry staining. In some embodiments, the means are reagents used to perform immunohistochemistry staining. In some embodiments, the reagents are used to prepare formalin-fixed and/or paraffin-embedded (FFPE) cell or tissue samples for immunohistochemistry staining. A description of immunohistochemistry can be found in U.S. Pat. No. 8,785,150, which is incorporated herein by reference in its entirety.

In some embodiments, the means are reagents used to perform histopathological scoring. In some embodiments, the means for comparing the quantified level of expression of c-MAF to a reference c-MAF expression level includes a quantifiable internal reference standard for c-MAF. In some embodiments, the metastasis is bone metastasis. In some embodiments, the bone metastasis is osteolytic bone metastasis.

In another aspect, the invention relates to a kit for predicting the clinical outcome of a subject suffering from bone metastasis from a cancer, the kit comprising: a) means for quantifying the expression level of c-MAF in a sample of said subject; and b) means for comparing the quantified expression level of c-MAF in said sample to a reference c-MAF expression level.

In another aspect the invention relates to a kit for determining a therapy for a subject suffering from cancer, the kit comprising: a) means for quantifying the expression level of c-MAF in a sample of said subject; b) means for comparing the quantified expression level of c-MAF in said sample to a reference c-MAF expression level; and c) means for determining a therapy for preventing and/or reducing bone metastasis in said subject based on the comparison of the quantified expression level to the reference expression level.

In another aspect the invention relates to a kit comprising: i) means for quantifying the expression level of c-MAF in a sample of a subject suffering from, and ii) one or more c-MAF gene expression level indices that have been predetermined to correlate with the risk of bone metastasis.

In some embodiments, the invention provides a kit for predicting bone metastasis of a cancer in a subject suffering from said cancer, the kit comprising: a) the antigen binding molecule or fragment thereof described herein or a polypeptide encoded for by a polynucleotide described herein, which is used to quantify the expression level of c-MAF in a tumor sample of said subject; and b) means for comparing the quantified level of expression of c-MAF in said sample to a reference c-MAF expression level.

Means for quantifying the expression level of c-MAF in a sample of said subject have been previously described in detail including 16q23 and 16q22-24 locus amplification and translocation.

In one embodiment, means for quantifying expression comprise a set of antibodies. In some embodiments, the means for quantifying expression further comprises probes and/or primers that specifically bind and/or amplify the c-MAF gene.

In a particular embodiment the cancer is breast cancer, lung cancer, prostate cancer, or renal cancer.

All the particular embodiments of the methods of the present invention are applicable to the kits of the invention and to their uses.

In the kit, the binding member (e.g., antibody) may be labeled to allow its reactivity in a sample to be determined, e.g. as described further below. Further the binding member may or may not be attached to a solid support. Components of a kit are generally sterile and in sealed vials or other containers. Kits may be employed in diagnostic analyses or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member, which binds to the first binding member and is conjugated to a detectable label (e.g., a fluorescent label, radioactive isotope or enzyme). Antibody-based kits may also comprise beads for conducting immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

EXAMPLES

Example 1

Construction of a c-MAF Specific Antibody

Antibody INB-1-11-8 was raised against an epitope corresponding to the amino acids 83-EQKAHLEDYYWMTGYPQQ-100 (18 a.a.) (SEQ ID NO: 22) of c-MAF of human origin. The epitope was coupled to KLH (NAc-EQKAHLEDYYWMTGYPQQ-Ahx-C-KLH (20 a.a.)). This antibody was compared to M153 (Santa Cruz Biotechnologies Inc.). The M153 antibody was raised against epitope corresponding to amino acids 19-171 of c-MAF of mouse origin. c-MAF is highly conserved between human and mouse (see alignment at FIG. 2).

The INB-1-11-8 light chain sequence (FIG. 8) is SEQ ID NO: 20 (Leader (SEQ ID NO: 24); Framework 1 (SEQ ID NO: 25); CDR1 (SEQ ID NO: 26); Framework 2 (SEQ ID NO: 27); CDR2 (SEQ ID NO: 28); Framework 3 (SEQ ID NO: 29); CDR3 (SEQ ID NO: 30); Junction (SEQ ID NO: 31); LC portion (SEQ ID NO: 32))

The closest Human germinal sequences to the light chain of the INB-1-11-8 light chain sequence are as follows:

```
>VKI_2-1-(U)_L12
                                               (SEQ ID NO: 23)
DIQMTQSPSTLSASVGDRVTITC RASQSISS------WLA WYQQK
PGKAPKLLIYDASSLES GVPSRFSGSGSGTEFTLTISSLQPDDFAT
YYC QQYNSYS

>VKI_2-1-(1)_L19
                                               (SEQ ID NO: 46)
DIQMTQSPSSVSASVGDRVTITC RASQGISS------WLA WYQQK
PGKAPKLLIYAASSLQS GVPSRFSGSGSGTDFTLTISSLQPEDFAT
YYC QQANSFP

>VKI_2-1-(1)_L5
                                               (SEQ ID NO: 47)
DIQMTQSPSSVSASVGDRVTITC RASQGISS------WLA WYQQK
PGKAPKLLIYAASSLQS GVPSRFSGSGSGTDFTLTISSLQPEDFAT
YYC QQANSFP
```

The INB-1-11-8 heavy chain sequence (FIG. 8) is SEQ ID NO: 16 (Leader (SEQ ID NO: 36); Framework 1 (SEQ ID NO: 37); CDR1 (SEQ ID NO: 38); Framework 2 (SEQ ID NO: 39); CDR2 (SEQ ID NO: 40); Framework 3 (SEQ ID NO: 41); CDR3 (SEQ ID NO: 42); Junction (SEQ ID NO: 43) HC portion (SEQ ID NO: 44))

The closest human germinal sequences of the INB-1-11-8 heavy chain sequence are as follows:

```
>VH3_1-3_3-64
                                               (SEQ ID NO: 33)
EVQLVESGGGLVQPGGSLRLSCAASGFTFS S--YAMH WVRQAPGK
GLEYVSAISS---NGGSTYYANSVKG RFTISRDNSKNTLYLQMGSLR
AEDMAVYYCAR

>VH3_1-1_3-66
                                               (SEQ ID NO: 34)
EVQLVESGGGLVQPGGSLRLSCAASGFTVS S--NYMS WVRQAPGK
GLEWVSVIY---SGGSTYYADSVKG RFTISRDNSKNTLYLQMNSLR
AEDTAVYYCAR

>VH3_1-1_3-53
                                               (SEQ ID NO 35)
EVQLVETGGGLIQPGGSLRLSCAASGFTVS S--NYMS WVRQAPGK
GLEWVSVIY---SGGSTYYADSVKG RFTISRDNSKNTLYLQMNSLR
AEDTAVYYCAR
```

Maf antibody sensitivity was calculated in a range of crescent dilutions of primary antibody from 1:10 to 1:1000. Antibody specificity was determined using parental and Maf-overexpressing (Maf long and short isoforms) MCF7, T47D (obtained from The American Type Culture Collection; ATCC) and 0990 human breast cancer cells. Formalin-fixed cell pellets were processed using immunohistochemistry standard procedures. Specificity was also shown in heterotopic MCF7 and MCF7-Maf (Long and short isoforms) xenoimplants in balb-c mice [mouse type]. Sections from the same specimens incubated with normal rabbit IgG2 (IS600, Dako) instead primary antibodies were used as negative controls.

Antigen Specific ELISA

Figure 3:
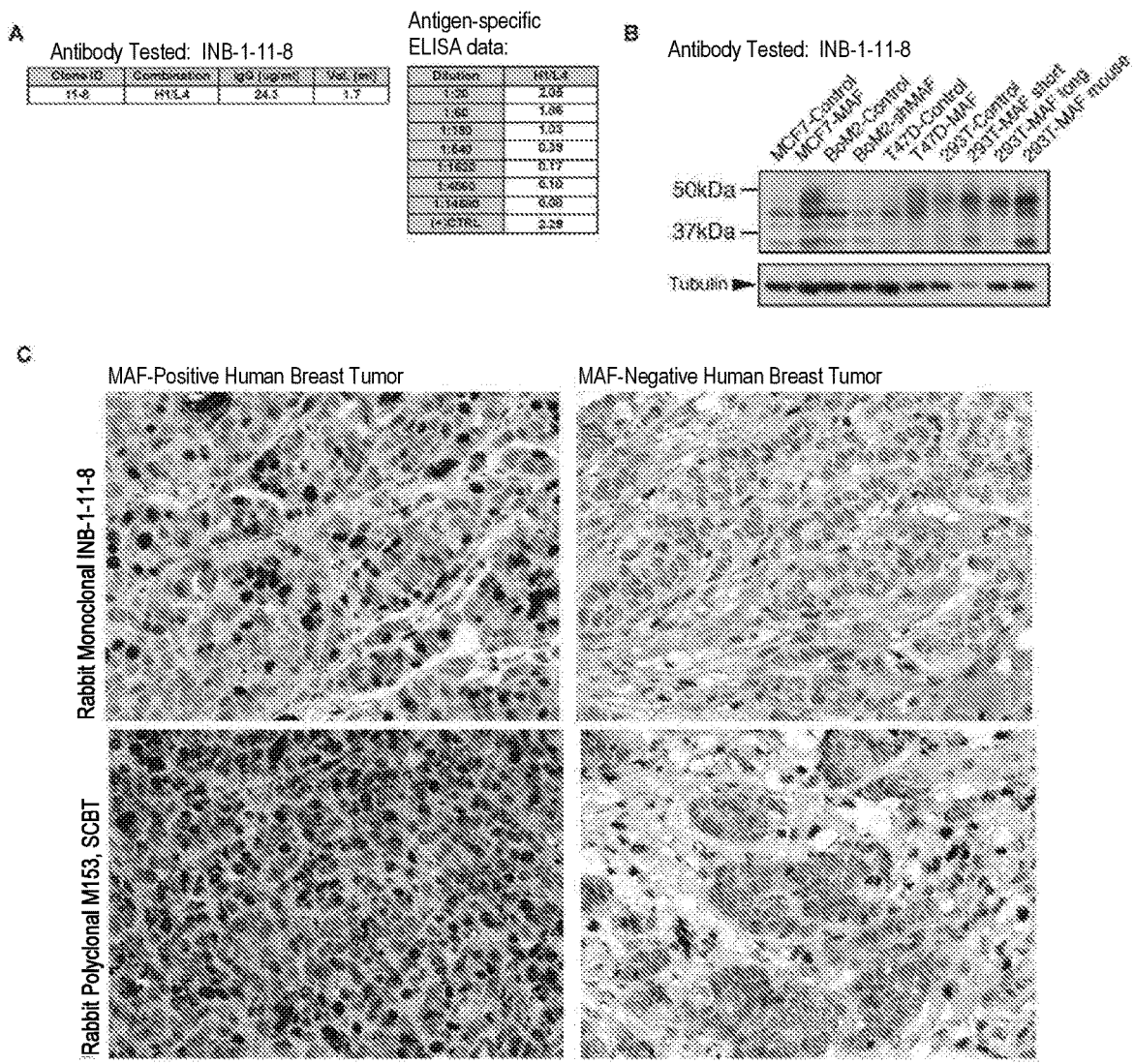
FIG. 3. A) Elisa antigen-specific binding results. INB-1-11-8 was tested in a range of dilutions to assess its specificity for antigen binding. The results confirmed that antigen affinity was retained even at dilutions above 1:500. B) INB-1-11-8 Antibody specificity was tested by western blot. The antibody was used at 1:50 dilution using 3% BSA as the blocking solution. The antibody specifically recognized endogenous c-MAF isforms (including post translational modified proteins) and its degradation forms. Moreover, it specifically recognized recombinantly expressed long and short human c-MAF isoforms and Mouse c-MAF isoform. MCF7 and T47 are ER+ breast cancer cell lines. BoM2 are a bone metastatic MCF7 derivative. 293T cells are kidney cells C) Representative c-MAF immunohistochemistry images of primary breast cancer tissues. The left column images represents c-MAF positive tumors. The right column are c-MAF negative tumors. Top images were stained with INB-1-11-8 antibody against Maf. Bottom images, where acquired with M153 antibody from Santa Cruz Biotechnology Inc., are provided for comparison purposes.

An Antigen-specific ELISA was used to test the antibody sensitivity for the antigen. To this end, the epitope, Peptide 1, described above, was conjugated to BSA. This was attached to a the plate surface where the ELISA is performed and washed. The INB-1-11-8 c-MAF specific antibody was then applied so that it could bind to the antigen. Following, the incubation time and wash with TBST, a secondary antibody specific for rabbit antibodies and conjugated to Alkaline Phosphatase was used to score binding of the primary antibody to the antigen. Several dilutions were used to test the titer of the antibody, which is an indication of the affinity of the antibody for its antigen (FIG. 3A).

Western Blot c-MAF antibody specificity by western blot was calculated in a range of crescent dilutions of primary antibody from 1:50 to 1:250. Specificity was determined using parental and Maf-overexpressing (Maf long and short isoforms) MCF7, T47D, 293T (obtained from The American Type Culture Collection; ATCC) and BoM2 human breast cancer cells derived from MCF7 with bone metastasis propensity. Cell pellets were processed as described per standard procedures (Tarragona et al. *J. Biol. Chem.* (2012) 287: 21346-55) and results confirmed by western blot from whole lysates (FIG. 3B).

c-MAF Immunostaining.

Immunostaining was performed using 3 µm tissue sections, placed on plus charged glass slides in a Dako Link platform. After deparaffinization, heat antigen retrieval was performed in pH 6.1, 0.01 mol/L citrate-based buffered solution (Dako). Endogenous peroxidase was quenched. A mouse polyclonal anti-cMaf antibody was used for 30 minutes at room temperature, 1:100 dilution, followed by incubation with an anti-rabbit Ig dextran polymer coupled with peroxidase (Flex+, Dako). Sections were then visualized with 3,3'-diaminobenzidine (DAB) and counterstained with Hematoxylin (FIG. 3C).

Example 2

Figure 4:
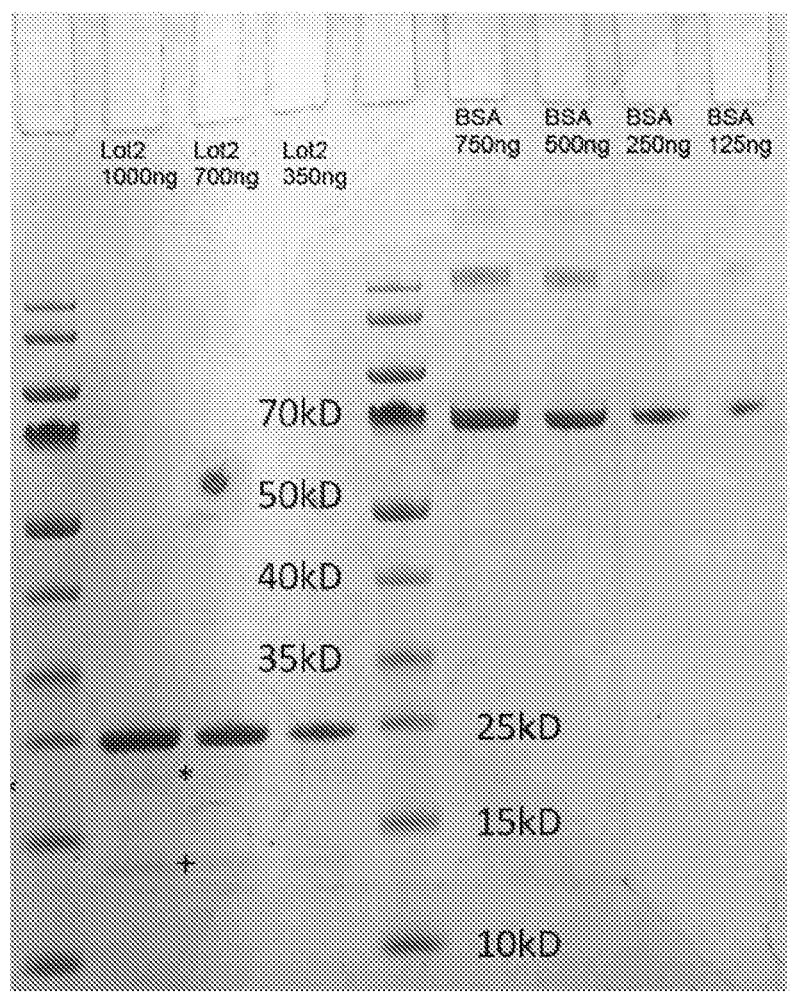
FIG. 4 illustrates an SDS-PAGE analysis of commercial BSA and cMaf (Q1) samples.

Analysis of the Interaction Between a Monoclonal Rabbit Antibody and the Antigen c-MAF a) Analysis of cMaf Protein Preparations by SDS-PAGE To confirm the purity of the antigen preparation, c-MAF (Q1) was compared to a commercial BSA standard through the use of SD S-PAGE under reducing conditions. Three amounts (800 ng, 550 ng and 275 ng) of c-MAF (Q1) were compared to four amounts (750 ng, 500 ng, 250 ng and 125 ng) of BSA. FIG. 4 shows the SDS-PAGE gel after Coomassie staining.

The SDS-PAGE gel shows two distinct bands of approximately 25 kDa (~60%) and 20 kDa (*) (~40%) for c-MAF (Q1). The calculated molecular weight for the molecule based on the sequence information would be 19.2 kDa, anyhow such differences between calculated and apparent size in SDS-PAGE are common. For c-MAF (Q1) the nominal concentration seems to have a lower (less than a third) concentration as indicated on the vial.

Mr=19.2 kDa; pI 5,6; no consensus N-glycosylation site; 2 Cysteines b) Analysis of c-MAF Protein Preparations by Calibration Free Concentration Analysis (CFCA)

To determine active concentrations of c-MAF (Q1) binding to INB-1-11-8, the

Figure 5:
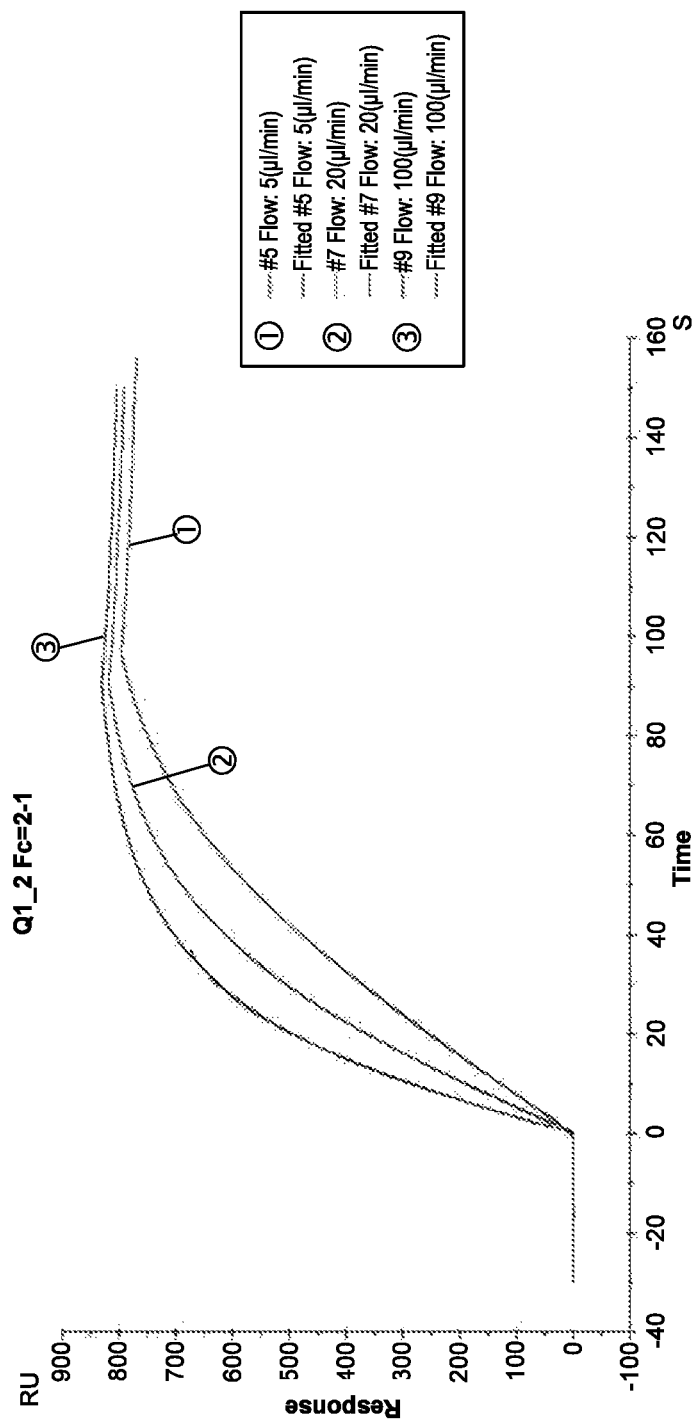
FIG. 5 illustrates an exemplary sensorgram of the CFCA-Analysis of cMaf (Q1).

CFCA method was used. The method relies on changes in the binding rate with varying flow rates, when the transport of molecules to the sensor surface is limited by diffusion. Concentrations are calculated from the measured binding rates and the molecular weight and estimated diffusion coefficient of the analyte. A high density of binding on the ligand surface was achieved by capturing >3000 RU of INB-1-11-8. Binding rates were measured at flow rates of 5, 20 and 100 µL/min. FIG. 5 shows an example of the sensorgrams of the CFCA analysis. A concentration of 1.3 mg/ml was determined for c-MAF (Q1). These results support the observations made in the SDS-PAGE analysis, where the concentration was estimated in comparison with the BSA standard. The CFCA measured concentration determined for the c-MAF (Q1), assuming that both the 25 kDa band and the smaller 20 kDa band observed in the SDS-PAGE have antibody binding activity. In this case, the amounts of the bands observed on the SDS-PAGE gel summed to estimate the active concentration of the antigen preparation.

c) Kinetic Analysis

Kinetic measurements were performed under the following conditions to measure the affinity constants between the antibody INB-1-11-8 and the c-MAF (Q1) preparation:

Experimental Conditions
Instrument: BiacoreT200
Running buffer: HBS-EP, 10 mM HEPES, 150 mM NaCl, 3 mM EDTA, 0.05% Tween 20, pH 7.4
Assay Temperature: 25° C.
Sensor-surface: Recombinant Protein A; Immobilized by standard amine-coupling (EDC/NHS chemistry)

Figure 6:
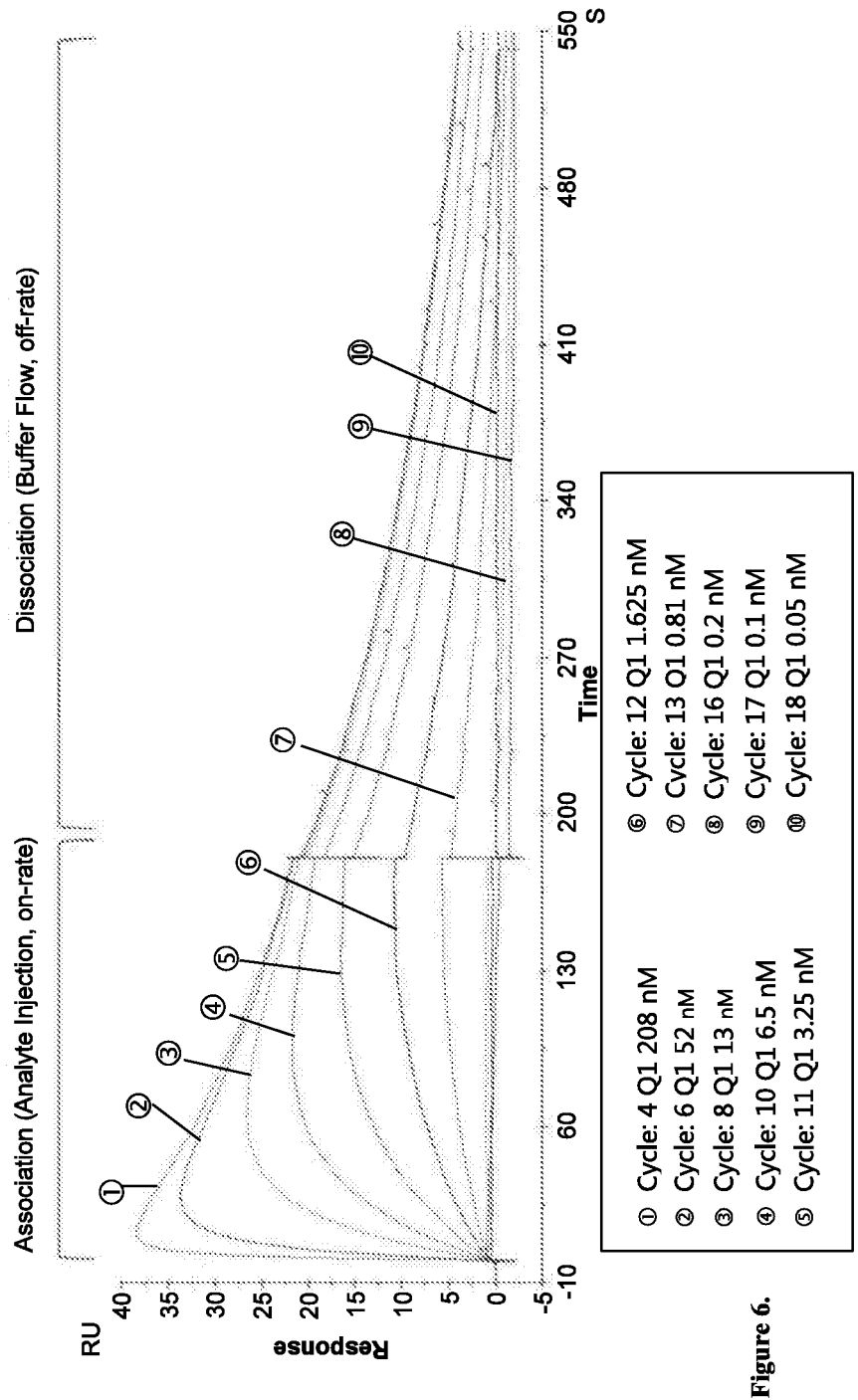
FIG. 6 illustrates a kinetic analysis of c-MAF (Q1) binding to INB-1-11-8.

Test measurements were conducted to confirm protein A-binding of the antibody INB-1-11-8 and to select appropriate capture levels for the kinetic measurements of the analyte. A capture level of 240 RU was chosen for the measurement with c-MAF (Q1), resulting in an expected Rmax of ca 64 RU for two 19.6 kDa antigens binding per antibody molecule. To generate sufficiently high binding signals for the peptide, a higher capture level of 980 kDa was chosen, also resulting in an expected Rmax of ca 30 RU. Serial dilutions of the antigen were injected for 180 s, followed by a 600 s buffer injection for off-rate determination (see FIG. 6). For the c-MAF fragment the molar concentrations used for the serial dilutions were calculated based on the concentrations determined by CFCA. The kinetic measurements were performed twice to confirm the binding behavior. The figure show that for the Analyte fast binding at concentrations >10 nM for the protein.

Figure 7:
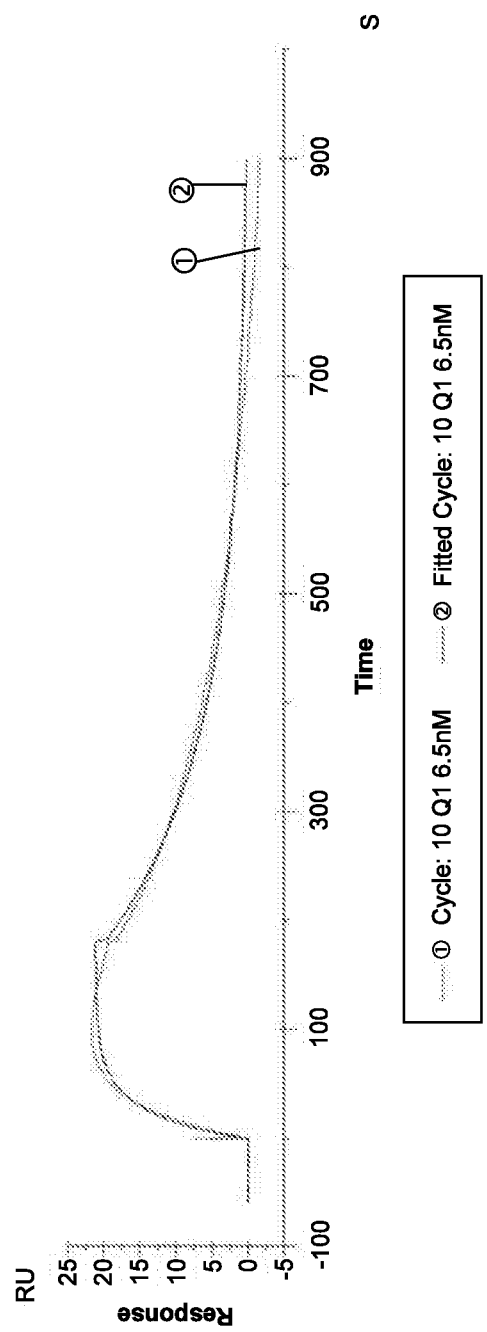
FIG. 7 illustrates a single concentration fit of c-MAF (Q1) binding to INB-1-11-8.

To estimate the affinity (Table 1) of the interactions of the c-MAF (Q1) with the antibody INB-1-11-8, single concentration fits based on a 1:1 interaction model were performed, assuming a Rmax of 23 RU (FIG. 7). Based on this preliminary data, an affinity in the nM-range has been roughly estimated for the interaction. The binding is characterized by a very fast association rate and a fast dissociation rate, i.e. the binding is not very tight.

TABLE 1

Estimated kinetic rate and equilibrium dissociation constant of c-MAF with antibody INB-1-11-8

| Sample | $c_{Analyte}$ | $k_{ass}$ | $k_{diss}$ | $K_D$ | $R_{max}$ | Chi$^2$ |
|---|---|---|---|---|---|---|
| c-MAF (Q1) | 6.5 nM | $5.3 \cdot 10^6 \cdot M^{-1}s^{-1}$ | $5.6 \cdot 10^{-3} \cdot s^{-1}$ | 1.1 nM | 23 RU | 0.77 | c-MAF (Q1): Fragment of c-MAF used including Aa 19-208

(SEQ ID NO: 45)
MEYVNDFDLMKFEVKKEPVETDRIISQCGRLIAGGSLSSTPMST

PCSSVPPSPSFSAPSPGSGSEQKAHLEDYYWMTGYPQQLNPEAL

GFSPEDAVEALISNSHQLQGGFDGYARGAQQLAAAAGAGAGASL

GGSGEEMGPAAAVVSAVIAAAAAQSGAGPHYHHHHHHAAGHHHH

PTAGAPGAAGSAAA

Reagents:
INB-1-11-8; c-MAF specific monoclonal antibody (rabbit) INB-1-11-8 (Clone ID11-8; Lot: 11-8); conc. 1.7 mg/ml; 3 aliquots, ca 200 µL
c-MAF (Q1) fragment
HBS-EP (Running Buffer)
CM5 sensor chip
Amine coupling kit
Protein-A
30 mM HCl (Regeneration Buffer)

Example 3

Validation Breast Cancer Primary Tumor Sample Cohort

The ability of the antibody to identify and predict bone metastasis was tested in a human breast tumor cohort. The validation set was composed of more than 380 primary breast cancer specimens from patients with stage I, II or III breast cancer and annotated clinical follow up (Rojo F., Ann Oncol 23 (5): 1156-1164 (2012)). Tissue microarrays were processed as per standard procedures. Tumors were classified according to standard clinicopathological parameters and then the appropriate statistical analysis was performed to see if c-MAF (MAF) protein expression in these tumors correlates with bone metastasis events.

Statistical analyses in this second cohort were based on the following premises:

i) Diagnostic Performance

Figure 9:
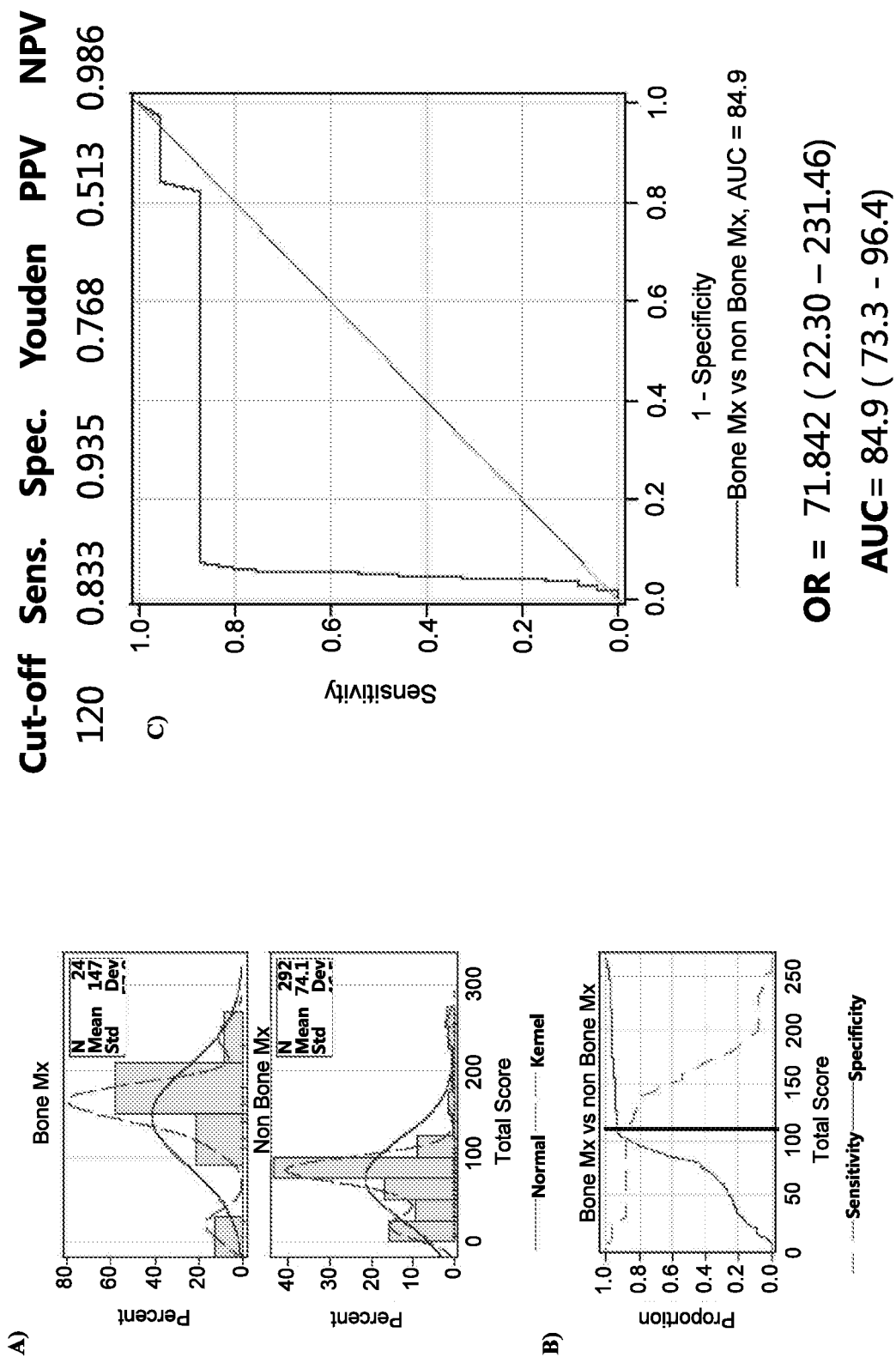
FIG. 9. A) IHC Score. Model evaluation: Histogram Plot. B) Sensitivity and Specificity plot. C) Receiving operating curve (ROC).

Diagnostic performance was evaluated by comparing the AUG of the ROC curves. Sensitivity (Se), specificity (Sp), positive predictive value (PPV) and negative predictive value (NPV) were computed for each of the classification categories based on the most predictive variables (MAF IHC levels) (FIG. 9). The cut off for selecting MAF positive and negative tumors was established based on the receiving operating curve parameters (ROC)

ii) Comparison of Baseline Characteristics (FIG. 10).

Figure 11:
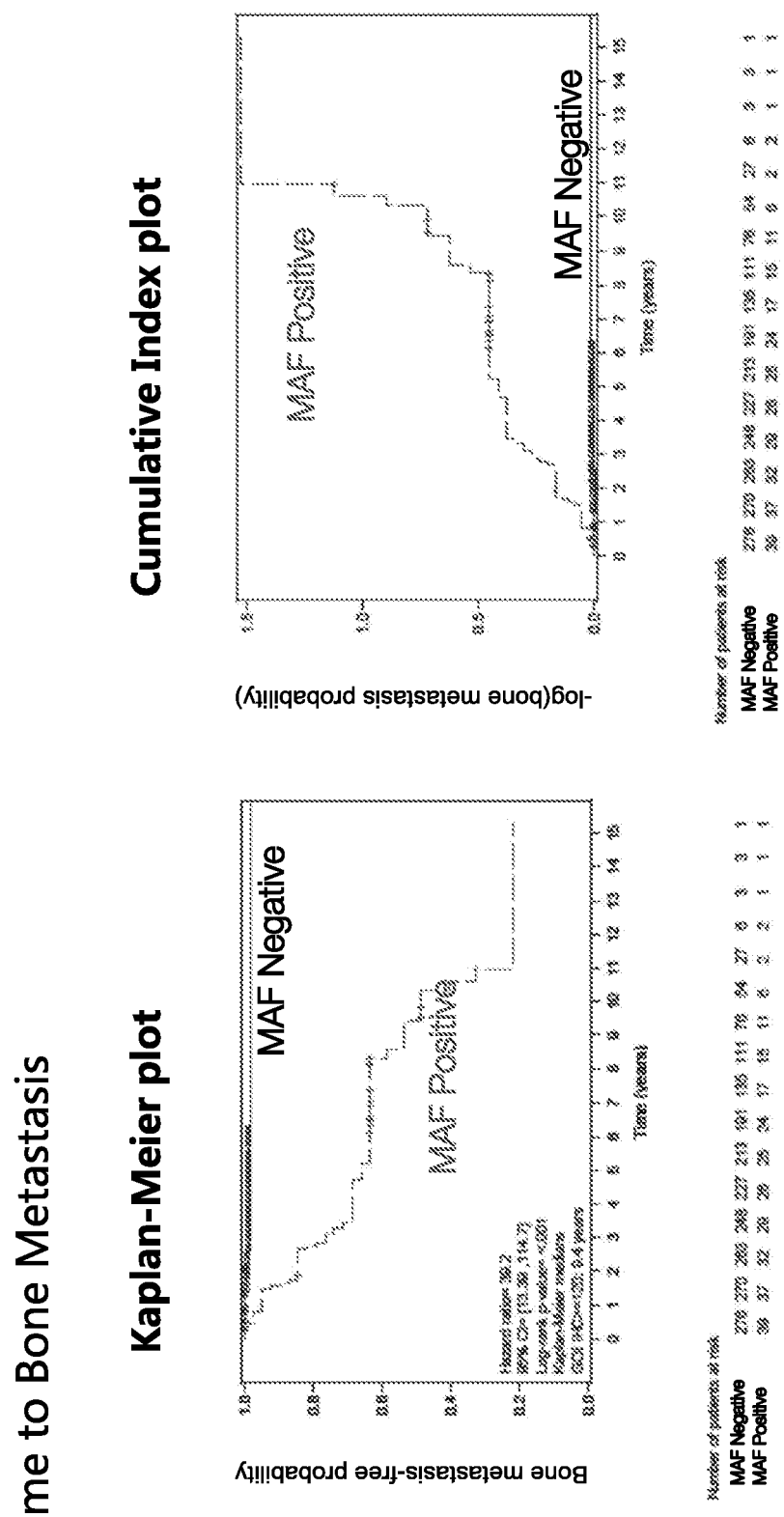
FIG. 11. A) Kaplan-Meier curve depicting bone metastasis-free probability; B) cumulative bone metastasis incidence plot.

The differences in the mean of age were tested with Kruskal-Wallis test. Categorical variables were compared with a chi-square test when applicable.

iii) Prognostic Role—Cox Regression Modeling and Hazard Ratio of the Outcome Time to Bone Metastasis was Calculated (FIG. 11).

It is understood that the examples and embodiments described herein are for illustrative purposes only and that various modifications or changes in light thereof will be suggested to persons skilled in the art and are to be included with the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The invention claimed is:

1. A binding member that specifically binds to human c-MAF, wherein the binding member comprises a heavy chain CDR1 comprising the amino acid sequence of SEQ ID NO: 38, a heavy chain CDR2 comprising the amino acid sequence of SEQ ID NO: 40, a heavy chain CDR3 comprising the amino acid sequence of SEQ ID NO: 42, a light chain CDR1 comprising the amino acid sequence of SEQ ID NO: 26, a light chain CDR2 comprising the amino acid sequence of SEQ ID NO: 28 and a light chain CDR3 comprising the amino acid sequence of SEQ ID NO: 30.

2. The binding member of claim 1, wherein said binding member is an antibody.

3. The binding member of claim 2, wherein the antibody is a rabbit antibody, a chimeric antibody or a humanized antibody.

4. The binding member of claim 1, wherein said binding member comprises a VH domain with a sequence that is at least about 80%, at least about 85%, at least about 90%, at least about 99%, or 100% identical to the amino acid sequence of SEQ ID NO: 17.

5. The binding member of claim 1, wherein the binding member comprises a $V_L$ domain with a sequence that is at least about 80%, at least about 85%, at least about 90%, at least about 99%, or 100% identical to the amino acid sequence of SEQ ID NO: 21.

6. The binding member of claim 1, wherein the binding member comprises a heavy chain sequence that is at least about 80%, at least about 85%, at least about 90%, at least about 99%, or 100% identical to the amino acid sequence of SEQ ID NO: 16.

7. The binding member of claim 1, wherein the binding member comprises a light chain sequence that is at least about 80%, at least about 85%, at least about 90%, at least about 99%, or 100% identical to the amino acid sequence of SEQ ID NO: 20.

8. A polynucleotide encoding the binding member of claim 1.

9. The polynucleotide of claim 8, wherein the polynucleotide encodes an antigen binding molecule.

10. The polynucleotide of claim 8, wherein the binding member is an antibody.

11. The polynucleotide of claim 8, wherein the polynucleotide comprises a VH domain with a sequence that is at least about 80%, at least about 85%, at least about 90%, at least about 99%, or 100% identical to the nucleotide sequence of SEQ ID NO: 15.

12. The polynucleotide of claim 8, wherein the polynucleotide encodes a $V_L$ domain with a sequence that is at least about 80%, at least about 85%, at least about 90%, at least about 99%, or 100% identical to the nucleotide sequence of SEQ ID NO: 20.

13. The polynucleotide of claim 8, wherein the polynucleotide encodes a heavy chain with a sequence that is at least about 80%, at least about 85%, at least about 90%, at least about 99%, or 100% identical to the nucleotide sequence of SEQ ID NO: 14.

14. The polynucleotide of claim 8, wherein the polynucleotide encodes a light chain with a sequence that is at least about 80%, at least about 85%, at least about 90%, at least about 99%, or 100% identical to the nucleotide sequence of SEQ ID NO: 18.

15. The binding member of claim 1, wherein the binding member binds to the epitope encoded by SEQ ID NO: 22.

16. The binding member of claim 1, wherein the binding member binds to human c-MAF with an affinity (KD) of at least about 1.5 nM or less, at least about 1.2 nM or less, or at least about 1.1 nM or less.

17. A vector comprising the polynucleotide of claim 8.

18. A host cell expressing the binding member of claim 1.

19. A method of producing an antigen binding member comprising culturing the host cell of claim 18.

20. A method of using an antigen binding member produced by the host cell of claim 18 to detect c-MAF.

21. An in vitro method for the diagnosis of metastasis in a subject with cancer or for the prognosis of the tendency to develop metastasis in a subject with cancer, said method comprising:
(i) quantifying the c-MAF gene expression level in a tumor sample of said subject using the binding member of claim 1, and
(ii) comparing the expression level obtained in (i) with the expression level of the c-MAF gene in a control sample,
wherein if the expression level of the c-MAF gene in said tumor sample is increased with respect to the expression level of the c-MAF gene in the control sample, then said subject has a positive diagnosis for metastasis or a greater tendency to develop metastasis.

22. An in vitro method for designing a customized therapy for a subject with cancer and an increased c-MAF expression level, said method comprising:
(i) quantifying the c-MAF gene expression level in a tumor sample of said subject using the binding member of claim 1, and
(ii) comparing the expression level obtained in (i) with the expression level of the c-MAF gene in a control sample,
wherein if the expression level of the c-MAF gene in said tumor sample is increased with respect to the expression level of the c-MAF gene in the control sample, then said subject is susceptible to receive a therapy aiming to prevent, inhibit, and/or treat metastasis or a therapy to prevent, inhibit, and/or treat bone degradation.

* * * * *

UNITED STATES PATENT AND TRADEMARK OFFICE
CERTIFICATE OF CORRECTION

| | |
|---|---|
| PATENT NO. | : 10,793,642 B2 |
| APPLICATION NO. | : 15/534893 |
| DATED | : October 6, 2020 |
| INVENTOR(S) | : Gomis et al. |

It is certified that error appears in the above-identified patent and that said Letters Patent is hereby corrected as shown below:

In the Claims

In Claim 4, at Column 113, Line 18, change "VH" to -- $V_H$ --.

In Claim 11, at Column 113, Line 44, change "VH" to -- $V_H$ --.

Signed and Sealed this
Fifth Day of January, 2021

Andrei Iancu
*Director of the United States Patent and Trademark Office*